US012780941B2

(12) United States Patent
Lazarus et al.

(10) Patent No.: US 12,780,941 B2
(45) Date of Patent: Nov. 3, 2026

(54) METHODS FOR TREATING INFLAMMATORY DISEASE WITH RBC-SPECIFIC ANTIBODIES

(71) Applicants: CSL LIMITED, Melbourne (AU); Canadian Blood Services, Ottawa (CA)

(72) Inventors: Alan Lazarus, Toronto (CA); Fabian Kaesermann, Burgdorf (CH); Sandra Koernig, Monee Ponds (CA); Andrew Crow, Ottawa (CA)

(73) Assignees: CSL LTD., Victoria (AU); Canadian Blood Services, Ottawa (CA)

( * ) Notice: Subject to any disclaimer, the term of this patent is extended or adjusted under 35 U.S.C. 154(b) by 0 days.

(21) Appl. No.: 16/757,053

(22) PCT Filed: Oct. 19, 2018

(86) PCT No.: PCT/AU2018/051136

§ 371 (c)(1),
(2) Date: Apr. 17, 2020

(87) PCT Pub. No.: WO2019/075523

PCT Pub. Date: Apr. 25, 2019

(65) Prior Publication Data

US 2020/0247903 A1 Aug. 6, 2020

(30) Foreign Application Priority Data

Oct. 20, 2017 (EP) .................................... 17197541
Sep. 14, 2018 (EP) .................................... 18194394

(51) Int. Cl.

| | |
|---|---|
| ***C07K 16/34*** | (2006.01) |
| ***C07K 16/28*** | (2006.01) |
| ***C07K 16/42*** | (2006.01) |
| *A61K 39/00* | (2006.01) |

(52) U.S. Cl.

CPC .......... *C07K 16/34* (2013.01); *C07K 16/2896* (2013.01); *C07K 16/42* (2013.01); *A61K 2039/505* (2013.01); *C07K 2317/52* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 5,892,019 | A | 4/1999 | Schlom et al. |
| 2014/0356384 | A1 | 12/2014 | Hubbell et al. |

FOREIGN PATENT DOCUMENTS

| | | | | |
|---|---|---|---|---|
| JP | H09509572 A | 9/1997 | | |
| JP | 2013541504 A | 11/2013 | | |
| WO | WO-9324630 A1 * | 3/1993 | | C12N 15/13 |
| WO | 199324630 A1 | 12/1993 | | |
| WO | 9407921 A1 | 4/1994 | | |
| WO | 1995022977 A1 | 8/1995 | | |
| WO | 199749809 A1 | 12/1997 | | |
| WO | WO-9749809 A1 * | 12/1997 | | A61K 39/395 |
| WO | 2009086552 A1 | 7/2009 | | |
| WO | WO-2010057626 A1 * | 5/2010 | | A61P 29/00 |
| WO | 2011051346 A1 | 5/2011 | | |
| WO | WO-2011137354 A2 * | 11/2011 | | A61P 37/00 |
| WO | 2012021512 A2 | 2/2012 | | |
| WO | 2013121296 A1 | 8/2013 | | |
| WO | WO-2016073917 A1 * | 5/2016 | | C07K 16/2887 |
| WO | 2017015141 A1 | 1/2017 | | |

OTHER PUBLICATIONS

Van Roon, Joel AG. "Activating and inhibitory Fcγ receptors in rheumatoid arthritis: from treatment to targeted therapies." (2007): 1-2 (Year: 2007).*

Crow, Andrew R., et al. "Treating murine inflammatory diseases with an anti-erythrocyte antibody." Science translational medicine 11.506 (2019). (Year: 2019).*

Cush, John J., et al. "Elevated interleukin-10 levels in patients with rheumatoid arthritis." Arthritis & Rheumatism: Official Journal of the American College of Rheumatology 38.1 (1995): 96-104.. (Year: 1995).*

Ludwig, Ralf J., et al. "Mechanisms of autoantibody-induced pathology." Frontiers in immunology 8 (2017): 603. (Year: 2017).*

Villa, Carlos H., et al. "Delivery of drugs bound to erythrocytes: new avenues for an old intravascular carrier." Therapeutic delivery 6.7 (2015): 795-826. (Year: 2015).*

De Taeye, Steven W., Theo Rispens, and Gestur Vidarsson. "The ligands for human IgG and their effector functions." Antibodies 8.2 (2019): 30. (Year: 2019).*

Jefferis, Royston. Biotechnology progress 21.1 (2005): 11-16 (Year: 2005).*

Janeway, Charles A. "Immunobiology: The Immune System in Health and Disease." 2001 (Year: 2001).*

Song, Seng et al. Blood vol. 105,4 (2005): 1546-8. doi:10.1182/blood-2004-05-1886 (Year: 2005).*

(Continued)

*Primary Examiner* — Misook Yu

*Assistant Examiner* — Lia E Taylor

(74) *Attorney, Agent, or Firm* — McNeill PLLC

(57) ABSTRACT

The invention relates to an antibody to a red blood cell for use in treating or preventing an inflammatory disorder, and to methods of treating or preventing an inflammatory disorder comprising administering to a subject in need thereof a therapeutically effective amount of an antibody to a red blood cell.

14 Claims, 13 Drawing Sheets

Figure 1:
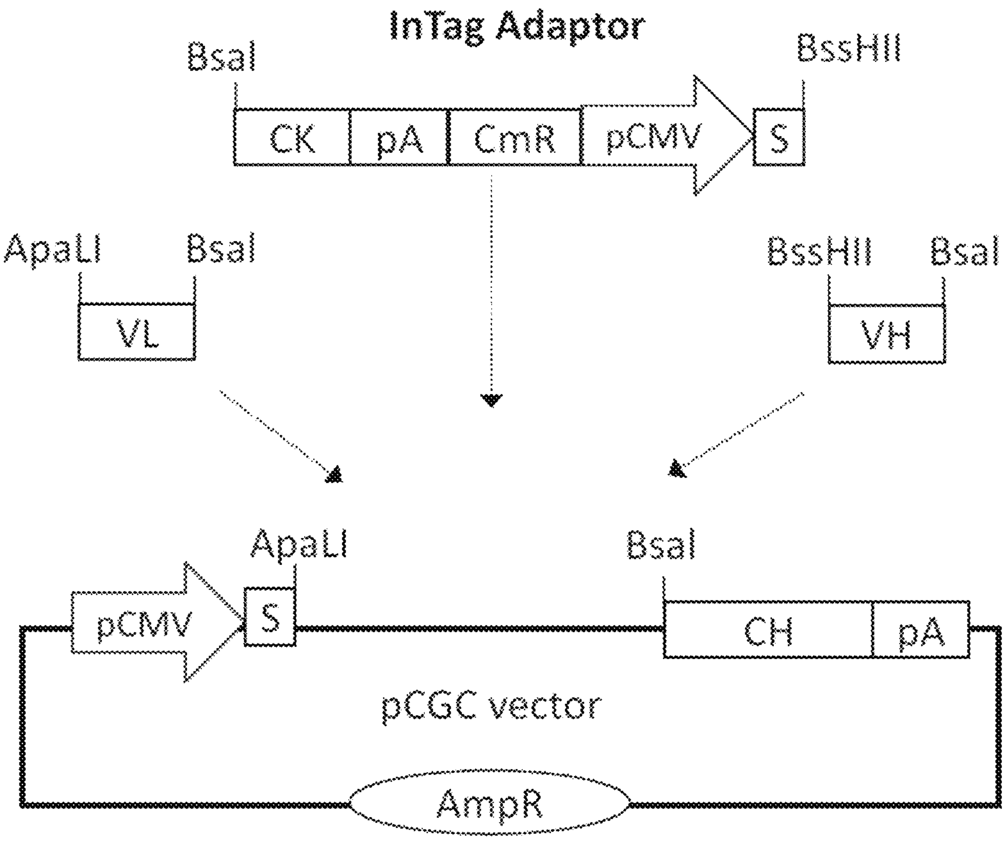

Specification includes a Sequence Listing.

(56) References Cited

OTHER PUBLICATIONS

Gorman, S D, and M R Clark. Seminars in immunology vol. 2,6 (1990): 457-66 (Year: 1990).*
De Taeye, et al.Antibodies 8.2 (2019): 30 (Year: 2019).*
Cush, John J., et al. Arthritis & Rheumatism: Official Journal of the American College of Rheumatology 38.1 (1995): 96-104 (Year: 1996).*
Hwang, William Ying Khee, and Jefferson Foote. "Immunogenicity of engineered antibodies." Methods 36.1 (2005): 3-10. (Year: 2005).*
Janeway CA Jr, Travers P, Walport M, et al. Immunobiology: The Immune System in Health and Disease. 5th Edition. New York: Garland Science; 2001 (Year: 2001).*
Kinne, Raimund W., Bruno Stuhlmüller, and Gerd-R. Burmester. "Cells of the synovium in rheumatoid arthritis. Macrophages." Arthritis research & therapy 9 (2007): 1-16. (Year: 2007).*
Feketeová, Lucia et al. "Effect of methotrexate on inflammatory cells redistribution in experimental adjuvant arthritis." Rheumatology international vol. 32, 11 (2012): 3517-23. doi: 10.1007/s00296-011-2177-3 (Year: 2012).*
Schöneberg, T. (2008). Tolerance and Desensitization. In: Offermanns, S., Rosenthal, W. (eds) Encyclopedia of Molecular Pharmacology. Springer, Berlin, Heidelberg. https://doi.org/10.1007/978-3-540-38918-7_140 (Year: 2008).*
Villa, C. H., Pan, D. C., Zaitsev, S., Cines, D. B., Siegel, D. L., & Muzykantov, V. R. (2015). Delivery of drugs bound to erythrocytes: new avenues for an old intravascular carrier. Therapeutic delivery, 6(7), 795-826 (Year: 2015).*
De Sá Oliveira, G G et al. "Diverse antigen specificity of erythrocyte-reactive monoclonal autoantibodies from NZB mice." Clinical and experimental immunology vol. 105,2 (1996): 313-20. doi: 10.1046/j.1365-2249.1996.d01-772.x (Year: 1996).*
Smith, Patrick, et al. "Mouse model recapitulating human Fcγ receptor structural and functional diversity." Proceedings of the National Academy of Sciences 109.16 (2012): 6181-6186 (Year: 2012).*
Shekhar, Sudhanshu et al. "Mouse IgG2a Antibodies Specific for the Commensal *Streptococcus mitis* Show Stronger Cross-Reactivity with *Streptococcus pneumoniae* than IgG1 Antibodies." Journal of immunology research vol. 2019 7906724. Sep. 10, 2019, doi: 10.1155/2019/7906724 (Year: 2019).*
Aglas, Lorenz, et al. "In vivo induction of functional inhibitory IgG antibodies by a hypoallergenic Bet v 1 variant." Frontiers in immunology 11 (2020): 2118 (Year: 2020).*
Vukovic, Natasa, et al. "Mouse IgG2a Isotype Therapeutic Antibodies Elicit Superior Tumor Growth Control Compared with mIgG1 or mIgE." Cancer research communications 3.1 (2023): 109-118 (Year: 2023).*
Crow et al., "Treating murine inflammatory diseases with an anti-erythrocyte antibody", Sci. Transl. Med., 11(21), pp. 1-13 (2019).
Extended European Search Report issued in EP 18868425.2, dated Aug. 2, 2021 (9 pages).
Nagelkerke et al., "Inhibition of FcgR-mediated phagocytosis by IVIg is independent of IgG-Fc sialylation and FcgRIIb in human macrophages", BLOOD, 124(25), pp. 3709-3718 (Dec. 11, 2014).
Kapur et al., "C-reactive protein enhances murine antibody-mediated transfusion-related acute lung injury", BLOOD, 126(25), pp. 2747-2751 (Dec. 17, 2015).
Campbell et al., "Therapeutic Targeting of the G-CSR Receptor Reduces Neutrophil Trafficking and Joint Inflammation in Antibody-Mediated Inflammatory Arthritis", J Immunol, 197, pp. 4396-4402 (Nov. 2, 2016).
Tong et al., "Optimal conditions for the performance of a monocyte monolayer assay", Transfusion, 56, pp. 2680-2690 (Nov. 2016).
Tong et al., "Use of a Monocyte Monolayer Assay to Evaluate Fcy Receptor-mediated Phagocytosis", J. Vis. Exp. (119), e55039, 7 pages (Jan. 2017).
Spirig et al., "rIgG1 Fc Hexamer Inhibits Antibody-Mediated Autoimmune Disease via Effects on Complement and Fc (gamma)Rs", J Immunol, 200, pp. 2542-2553 (Mar. 2018).
Fung et al., "Recipient T lymphocytes modulate the severity of antibody-mediated transfusion-related acute lung Injury", BLOOD, 116(16), pp. 3073-3079 (Oct. 21, 2010).
Crow et al., "Amelioration of murine immune thrombocytopenia by CD44 antibodies: a potential therapy for ITP?", Blood, 117(3), pp. 971-974 (Jan. 20, 2011).
Colmegna et al., "Current Understanding of Rheumatoid Arthritis Therapy", Clinical pharmacology & Therapeutics, 91(4), pp. 607-620 (Apr. 2012).
Mott et al., "CD44 Antibodies and Immune Thrombocytopenia in the Amelioration of Murine Inflammatory Arthritis", PLOS ONE, 8(6), e65805, 11 pages (Jun. 2013).
Campbell et al., "Therapeutic Effect of IVIG on Inflammatory Arthritis in Mice Is Dependent on the Fc Portion and Independent of Sialylation or Basophils", J Immunol, 192, pp. 5031-5038 (Apr. 2014).
Misharin et al., "Nonclassical Ly6Cminus Monocytes Drive the Development of Inflammatory Arthritis in Mice", Cell Reports 9, pp. 591-604 (Oct. 23, 2014).
Coopamah et al., "Anti-D initially stimulates an Fc-dependent leukocyte oxidative burst and subsequently suppresses erythrophagocytosis via interleukin-1 receptor antagonist", BLOOD, 102(8), pp. 2862-2867 (Oct. 15, 2003).
Kagari et al., "Essential Role of Fc(gamma) Receptors in Anti-Type II Collagen Antibody-Induced Arthritis", J Immunol, 170, pp. 4318-4324 (2003).
Song et al., "Monoclonal IgG can ameliorate immune thrombocytopenia in a murine model of ITP: an alternative to IVIG", Blood, 101(9), pp. 3708-3713 (May 1, 2003).
Kakhniashvill et al., "The Human Erythrocyte Proteome", Molecular & Cellular Proteomics 3.5, pp. 501-509 (2004).
Lazar et al., "Engineered antibody Fc variants with enhanced effector function", PNAS, 103(11), pp. 4005-4010 (Mar. 14, 2006).
Looney et al., "Neutrophils and their Fc*gamma* receptors are essential in a mouse model of transfusion related acute lung injury", J Clin Invest., 116(6), pp. 1615-1623 (2006).
Nandakumar et al., "Antibody-induced arthritis: disease mechanisms and genes involved at the effector phase of arthritis", Arthritis Research & Therapy, 8(6), 11 pages (Jan. 11, 2007).
Chapman et al., "Ten years of hemovigilance reports of transfusion-related acute lung injury in the United Kingdom and the impact of preferential use of male donor plasma", TRANSFUSION, 49, pp. 440-452 (Mar. 2009).
Hartung et al., "Clinical applications of intravenous immunoglobulins (IVIg)—beyond immunodeficiences and neurology", Clinical and Experimental Immunology, 158(Suppl. 1), pp. 23-33 (2009).
Oksenhendler et al., "Anti-RH Immunoglobulin Therapy for Human Immunodeficiency Virus-Related Immune Thrombocytopeniarpura", Blood, 71(5), pp. 1499-1502 (1988).
Leddy et al., "Erythrocyte membrane proteins reactive with human (warm-reacting) anti-red cell autoantibodies", J Clin Invest., 91(4), pp. 1672-1680 (1993).
Godeau et al., "Treatment of chronic autoimmune thrombocytopenia purpura with monoclonal anti-D", TRANSFUSION, 36, pp. 328-330 (1996).
Kouskoff et al., "Organ-Specific Disease Provoked by Systemic Autoimmunity", Cell, 87, pp. 811-822 (Nov. 29, 1996).
Tippett et al., "The Rh Antigen D: Partial D Antigens and Associated Low Incidence Antigens", Vox Sang, 70, pp. 123-131 (1996).
Campbell et al., "The colony-stimulating factors and collagen-induced arthritis: exacerbation of disease by M-CSF and G-CSF and requirement for endogenous M-CSF", Journal of Leukocyte Biology, 68, pp. 144-150 (Jul. 2000).
Kina et al., "The monoclonal antibody TER-119 recognizes a molecule associated with glycophorin A and specifically marks the late stages of murine erythroid lineage", British Journal of Haematology, 109, pp. 280-287 (2000).
Miescher et al., "CHO expression of a novel human recombinant IgG1 anti-RhD antibody isolated by phage display". British Journal of Haematology, 111, pp. 157-166 (2000).
Wu et al., "Experimental Autoimmune Myasthenia Gravis in the Mouse", Current Protocols in Immunology, 15.8.1-15.8.19 (1997).

(56) References Cited

OTHER PUBLICATIONS

Ambriz-Fernandez et al., "Fc Receptor Blockade in Patients with Refractory Chronic Immune Thrombocytopenia Purpura with Anti-D IgG", Archives of Medical Research, 33, pp. 536-540 (2002).
Tridandapani et al., "Regulated Expression and Inhibitory Function of Fc*gamma*RIIb in Human Monocytic Cells", The Journal of Biological Chemistry, 277(7), pp. 5085-5089 (Feb. 15, 2002).
Cooper et al., "Intravenous (IV) anti-D and IV immunoglobulin achieve acute platelet increases by different mechanisms: modulation of cytokine and platelet responses to IV anti-D by Fc*gamma*RIIa and Fc*gamma*RIIIa polymorphisms", British Journal of Haematology, 124, pp. 511-518 (2003).
Song et al., "Monoclonal antibodies that mimic the action of anti-D in the amelioration of murine ITP act by a mechanism distinct from that of IVIg", BLOOD, 105(4), pp. 1546-1548 (Feb. 15, 2005).
Kumar et al., "Cell-derived anaphylatoxins as key mediators of antibody-dependent type II autoimmunity in mice", J. Clin. Invest., 116(2), pp. 512-520 (2006).
Mannino et al., "The paradoxical role of IL-10 in immunity and cancer", Cancer Letters 367, pp. 103-107 (2015).
Gerenova et al., "IL-12B and IL-10 gene polymorphisms in the development of Hashimoto's thyroiditis", International Journal of Immunogenetics, 43, pp. 397-403 (2016).
Mingomataj et al., "Regulator Versus Effector Paradigm: Interleukin-10 as Indicator of the Switching Response", Clinic Rev Allerg Immunol, 50, pp. 97-113 (2016).
Yu et al., "Monovalent Fc receptor blockade by an anti-Fc*gamma* receptor/albumin fusion protein ameliorates murine ITP with abrogated toxicity", BLOOD, 127(1), pp. 132-138 (Jan. 7, 2016).
Hernandez-Bello et al., "Aberrant expression of interleukin-10 in rheumatoid arthritis: Relationship with IL 10 haplotypes and autoantibodies", Cytokine 95, pp. 88-96 (2017).
Lyu et al., "Upregulation of CD72 expression on CD19+CD27+ memory B cells by CD40L in primary immune thrombocytopenia", British Journal of Haematology, pp. 1-11 (2016).
Zhang et al., "Research on the negative immune regulation of NK cells in patients with primary immune thrombocytopenia", Chin J Hematol, 38(5), pp. 399-403 (May 2017).
Vermeulen et al., "Anti-D immunoglobulin treatment in chronic inflammatory demyelinating polyneuropathy", J. Neurol, 58(3), pp. 383-384 (1995).
Crow et al., "Erythrocyte-Specific Antibodies as a Potential New Therapeutic Modality in Autoimmune and Inflammatory Disorders Beyond Immune Thrombocytopenia (ITP)", Ash 59th Annual Meeting & Exposition Paper 102788, 2 pages (Dec. 9-12, 2017).
Khan et al., "Anti-D: A Type of IVIg", Antibody Therapy, 5, pp. 61-71 (2018).
Notification of Transmittal of the International Search Report and Written Opinion of the International Searching Authority, or the Declaration, International Search Report and Written Opinion in International Application No. PCT/AU2018/051136, mailed Nov. 8, 2018 (11 pages).

* cited by examiner

A

B

C

D

E

F

G

H

Mice per group
1. Ter119 (n=5)
2. Degly-Ter119 (n=5)
3. M1/69 (n=2)
4. Isotype control (n=4)

A

B

METHODS FOR TREATING INFLAMMATORY DISEASE WITH RBC-SPECIFIC ANTIBODIES

TECHNICAL FIELD

The invention relates to an antibody to a red blood cell for use in treating or preventing an inflammatory disorder, and to methods of treating or preventing an inflammatory disorder comprising administering to a subject in need thereof a therapeutically effective amount of an antibody to a red blood cell.

BACKGROUND OF THE INVENTION

Inflammatory disorders include a vast array of diseases and conditions that are characterized by inflammation. Examples include allergy, asthma, autoimmune diseases, coeliac disease, glomerulonephritis, hepatitis and inflammatory bowel disease, amongst others.

Current treatments for inflammatory disorders are as wide ranging as the diseases themselves, however one approach is the use of intravenous immunoglobulin (IVIg) to treat these diseases. IVIg preparations, which are therapeutic preparations of pooled polyspecific IgG that is commonly obtained from the plasma of healthy individuals, have been available since the early 1980s and have been used for the treatment of primary or secondary immunodeficiencies. Due to its multiple anti-inflammatory and immunomodulatory properties, IVIg is used successfully in a wide range of autoimmune and inflammatory conditions. Recognized autoimmune indications include idiopathic thrombocytopenic purpura (ITP), Kawasaki disease, Guillain-Barré syndrome and other autoimmune neuropathies, myasthenia gravis, dermatomyositis and several rare diseases (Hartung H P et al Clin Exp Immunol. 2009;158(Suppl 1):23-33).

Other treatments also involve antibodies. For example, monoclonal antibodies (mAbs) are also used in the treatment of inflammatory diseases. Many of these mAbs target molecules that have a role in inflammation, e.g. anti-tumor necrosis factor (anti-TNF), anti-interleukin-1 (anti-IL-1) receptor, anti-IL-6 receptor, anti-$\alpha 4$ integrin subunit, and anti-CD20 agents, which have been approved for the therapy of several inflammatory and immune diseases, including rheumatoid arthritis, Crohn's disease, ulcerative colitis, spondyloarthropathies, juvenile arthritis, psoriasis, psoriatic arthritis, and others.

Antibodies that bind to red blood cells (RBCs) have been used therapeutically for only 2 purposes, as a first-line therapy for patients with immune thrombocytopenia (ITP), and for Rh isoimmunization in mothers who are Rh negative.

The use in the treatment of ITP was originally brought into practice based on the ability of anti-RBC antibodies such as "anti-D" (a mixture of anti-D immunoglobulins purified from human plasma) to competitively inhibit opsonized platelet clearance by phagocytic cells in the mononuclear phagocytic system (MPS, formerly known as the reticuloendothelial system (RES)), since ITP is an autoimmune disease with antibodies detectable against several platelet surface antigens and one of the defining characteristics of ITP is a low platelet count. This arises at least in part as a result of the coating of platelets with IgG autoantibodies, which in turn renders them susceptible to opsonization and phagocytosis by splenic macrophages, as well as by Kupffer cells in the liver. It has been proposed that the ITP treatment is effective because by introducing these antibodies, the RBC become coated with antibodies and are subsequently cleared by the mononuclear phagocytic system (MPS, formerly known as the RES). This competes with the clearance of opsonised platelets which occurs by the same pathway, and results in reduced clearance of autoantibody-opsonized platelets.

This theory is supported by the observation that ITP patients have minimal or no response to anti-D after splenectomy. Anti-D opsonized RBC can also prevent the in vitro phagocytosis of opsonized platelets.

Monoclonal antibodies against a number of different mouse RBC molecules (e.g. CD24 and the TER-119 antigen) have been shown to successfully ameliorate thrombocytopenia in mouse models (Song S. et al Blood. 2003;101 (9):3708-3713). In mice CD24 appears to be expressed by RBC, but it is not believed to be expressed on human RBCs. In a further study, ITP patients who did not express RhD but expressed Rhc were successfully treated with anti-Rhc (Oksenhendler E et al Blood. 1988;71:1499-1502).

It has, however, been observed by the inventors, surprisingly that the amelioration of ITP by an antibody to the TER-119 antigen occurs rapidly, and before the measurable onset of anemia (induced by RBC clearance). Based on this observation, the simple MPS blockade mechanism that has previously been proposed appears inadequate to explain the antibody's effects, and further indicates that there is a broad anti-inflammatory activity involved. This has been confirmed by the inventors' demonstration in mouse models that the antibody to the TER-119 antigen can ameliorate inflammatory diseases that do not involve classical MPS function, specifically inflammatory arthritis and transfusion related acute lung injury (TRALI). The-anti TER-119 antigen antibody tested both prevents the induction of arthritis and can also ameliorate established disease in mice. In addition, it was able to prevent hypothermia and reduce pulmonary edema in a murine model of TRALI. On this basis anti RBC antibodies have significant therapeutic potential in inflammatory disorders.

DISCLOSURE OF THE INVENTION

The invention thus provides an antibody to a red blood cell for use in a method of treating or preventing an inflammatory condition.

Also provided is a method of treating or preventing an inflammatory condition in a subject, comprising administering to a subject in need thereof a therapeutically effective amount of an antibody to a red blood cell.

Also provided is the use of an antibody to a red blood cell for the manufacture of a medicament for treating or preventing an inflammatory condition.

In some embodiments, the antibody to a RBC binds specifically to a RBC molecule, preferably a RBC transmembrane molecule.

In some embodiments the antibody to a RBC is polyclonal, or monoclonal. The antibody may be monospecific or multispecific (e.g. monospecific). In some embodiments the antibody is isolated, polyclonal, monoclonal, multispecific, monospecific, mouse, human, fully human, humanized, primatized or chimeric. In one specific embodiment, the antibody to a RBC antigen is a monoclonal human or humanized antibody or a minibody (antibody fragment that is missing the constant region in the Fab portion). In some embodiments, the antibody to a RBC is selected from a Fab, Fab', F(ab')2, Fd, Fv, a single-chain Fv (scFv) and a disulfide-linked Fv (sdFv), diabodies, triabodies, tetrabodies; preferably such a fragment is linked or fused to an Fc-comprising moiety.

In some embodiments the antibody to a RBC is of the type IgG or IgM, and may in particular be a rat, mouse, human or humanised IgG or IgM, of any of type, preferably a human or humanised IgG or IgM. Human or humanised IgG may e.g. be of type IgG1, IgG2, IgG3 or IgG4. Rat or mouse IgG may also be used (e.g. rat IgG1, IgG2a, IgG2b or IgG2c, or mouse IgG2a, IgG2b, IgG2c, IgG3 or IgG4). The antibody to a RBC antigen preferably comprises an Fc region and preferably binds to an Fc receptor, e.g. Fcγ receptor (FcγR), such as FcγRI (CD64), FcγRIIA (CD32), FcγRIIB (CD32), FcγRIIIA (CD16a), FcγRIIIB (CD16b).

In some embodiments the inflammatory condition is an autoimmune condition, e.g. an auto-antibody mediated autoimmune condition. The autoimmune condition may be a condition in which elevated IL-10 is present (e.g. as compared to a healthy subject). The autoimmune condition may be a neurological condition, which in some embodiments is not ITP. The autoimmune condition may be (i) selected from chronic inflammatory demyelinating polyneuropathy (CIDP), myasthenia gravis (MG), multiple sclerosis (MS) and neuromyelitis optica (NMO), or (ii) selected from rheumatoid arthritis and TRALI.

In some embodiments the RBC antibody binds to a peptide epitope. In some embodiments the RBC antibody binds to a RBC molecule that is selected from the RhD protein, GPA, the human orthologue of TER-119 antigen (Ly76), and Band 3. In some embodiments the RBC antibody binds to a RBC molecule that is found at a density of $10^2$-$10^5$ copies per RBC. The antibody may be administered by any route, e.g. parenteral or non-parenteral. Preferred parenteral routes include intravenous, intramuscular, intraperitoneal, intracerebrospinal, subcutaneous, intra-articular, intrasynovial, intrathecal, topical administration or by inhalation. Typically, the antibody to a RBC is administered by intravenous or subcutaneous administration.

In some embodiments, the antibody to a RBC is administered so that an amount of antibody of about 0.001 mg/kg to about 100 mg/kg of the subject's body weight is administered in a given time scale, e.g. in one day, or one week, two weeks or one month. In certain embodiments, such weight-based dosage is chosen from about 0.01 mg/kg body weight per day or week, two weeks or one month, about 0.3 mg/kg body weight, about 1 mg/kg body weight per day or week, two weeks or one month, about 3 mg/kg body weight per day or week, two weeks or one month, and about 10 mg/kg body weight per day or week, two weeks or one month.

In some embodiments, the antibody to a RBC is administered at a fixed dosage. In a specific embodiment, the antibody to a RBC is administered so that an amount of antibody at a fixed dosage from about 50 μg to about 2000 mg is administered in a given time scale, e.g. in one day, one week, two weeks or one month.

The dosage regimen is thus defined in terms of the amount of antibody that is administered to a subject in a given time scale. The frequency of administration during that time scale will determine the amount of antibody that is administered each time. For example, if the dosage is 10 mg/kg/week, this could be administered as a single 10 mg/kg dose or as multiple doses with appropriately reduced amounts of antibody (e.g. 25 mg/kg doses in one week). In some embodiments, the antibody to a RBC is administered as a single dose (e.g. daily, weekly once every two weeks or once every month), or as multiple doses more frequently if the amount of antibody is lower each time it is administered. In general administration by the subcutaneous route can be carried out more frequently (e.g. once a day) than intravenous administration (e.g. once every two weeks or once a month).

In some embodiments, methods of the invention comprise further administering to the subject a therapeutically effective amount of one or more other therapeutic agent(s), preferably at least one other anti-inflammatory agent, or agent that is used to treat an inflammatory condition or to alleviate the symptoms thereof, e.g. an anti-inflammatory agent, immunosuppressive agent or analgesic.

In some embodiments the antibody binds preferably to a RBC. For example, the RBC molecule to which the RBC antibody binds may be found at a higher density on a RBC than on one or more other blood cell and/or a cell that is associated with the vascular system.

In some embodiments the antibody causes MPS blockade in a human or in a suitable animal model in vivo, or causes haemolysis in vivo, e.g. in an animal model or in a human, or inhibits phagocytosis of opsonised platelets in an in vitro assay.

LIST OF FIGURES

FIG. 1. Antibody cloning strategy. Vector and fragments were digested using enzymes indicated and cloned together by T4 DNA ligase. The recombinant clones were selected using chloramphenicol resistance marker (CmR) located in the InTag adaptor. pCMV: CMV promoter, pA: BGH polyA, S: ER Signal sequence.

Figure 2:
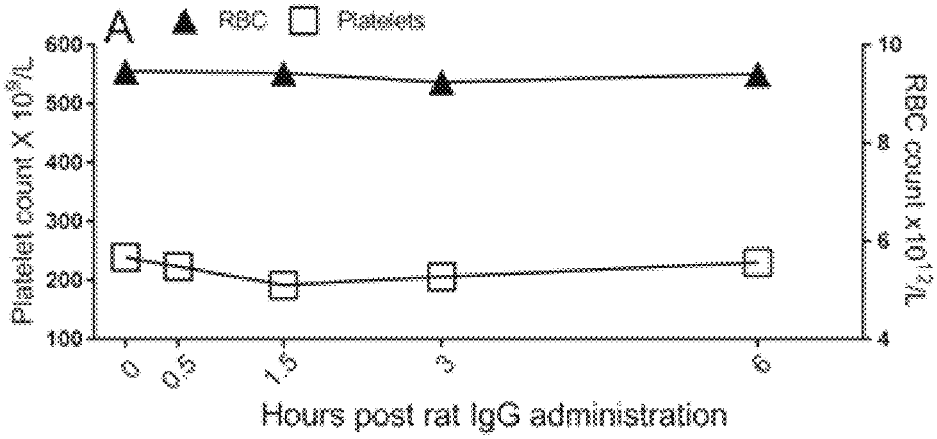
Figure 2:
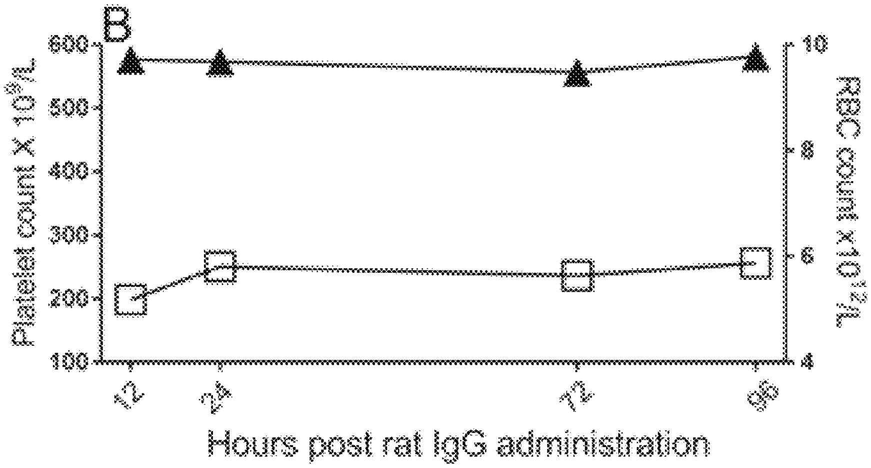
Figure 2:
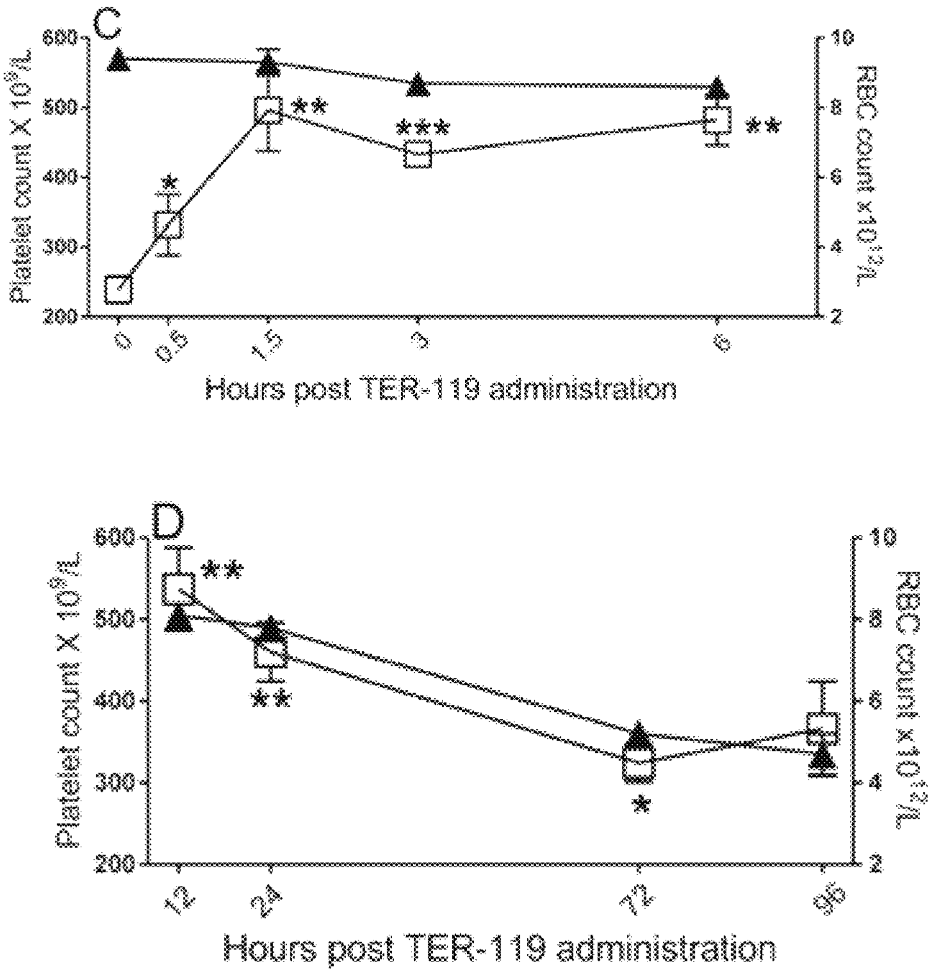

FIG. 2 shows that the amelioration of murine ITP can occur prior to detectable anemia. C57BL/6 mice were pretreated with 45 ug of rat IgG (A, B) or 45 ug of TER-119 antibody (C, D) and blood platelets as well as blood erythrocytes enumerated over the duration depicted on the x-axis. ITP was induced by 2 ug anti-platelet antibody (MWReg30) at the indicated time points on the x-axis. Platelets were enumerated 1 hour after MWReg30 injection. The left y-axis represents platelet enumeration (open square), the right y-axis represents RBC enumeration (closed triangle). Data are presented as mean±SEM from 5 separate experiments, 90 mice total. For thrombocytopenia, *P<0.05, P<0.001, *P<0.0001.

Figure 3:
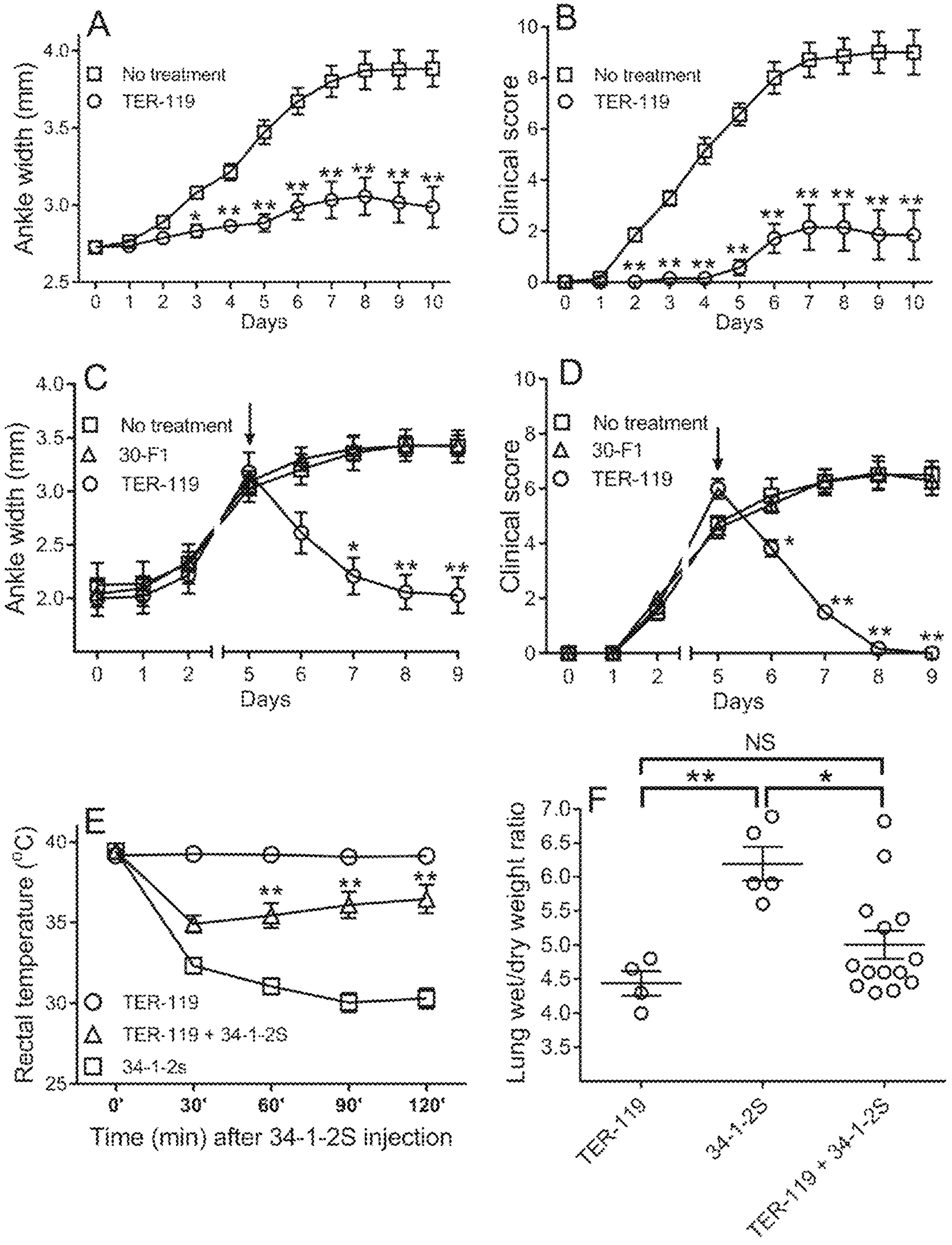

FIG. 3 shows that the monoclonal RBC specific antibody TER-119 inhibits inflammatory arthritis and transfusion related acute lung injury. On day 0, C57BL/6 mice were assessed for basal arthritis measurements (A, B). One group of mice received 45 ug TER-119 antibody (open circle) the other group (open square) received nothing. Two hours later, all mice received an injection of K/B×N serum. Ankle measurements (A) and clinical score (B) were taken every day for 10 days according to Mott P J et al PLoS One. 2013;8(6):e65805. Data are expressed as mean±S.E.M from 5 separate experiments. n=16 (K/B×N serum alone); n=13 (TER-119). P<0.005; **P<0.0001.

In independent experiments, mice received an injection of K/B×N serum with no pretreatment. On day 5, arthritic mice were treated (arrow) with nothing (open square), 50 ug 30F1 antibody (open triangle) or 45 ug TER-119 antibody (open circle). Ankle measurements (C) and clinical score (D) were measured on days 0, 1, 2 and 5-9 according to Mott P J et al PLoS One. 2013;8(6):e65805. Data are expressed as mean±S.E.M from 4 separate experiments. n=5 (K/B×N serum alone); n=6 (TER-119); n=7 (30-F1). *P<0.01; **P<0.0001.

For TRALI experiments, SCID mice were injected with 40 ug of TER-119 antibody (open circle, open triangle) or left untreated (open square) for 24 hrs. Mice were then injected with 50 ug of 34-1-2s (open triangle, open square) or nothing (open circle). Rectal temperatures were measured every 30 min for 2 hr (E). Mice were subsequently sacrificed at 2 hr to assess pulmonary edema (F). Data are expressed as mean±S.E.M from 4 separate experiments. n=4 (TER-119); n=5 (34-1-2S); n=14 (TER-119+34-1-2S). *P=0.006; **P=0.001.

Figure 4:
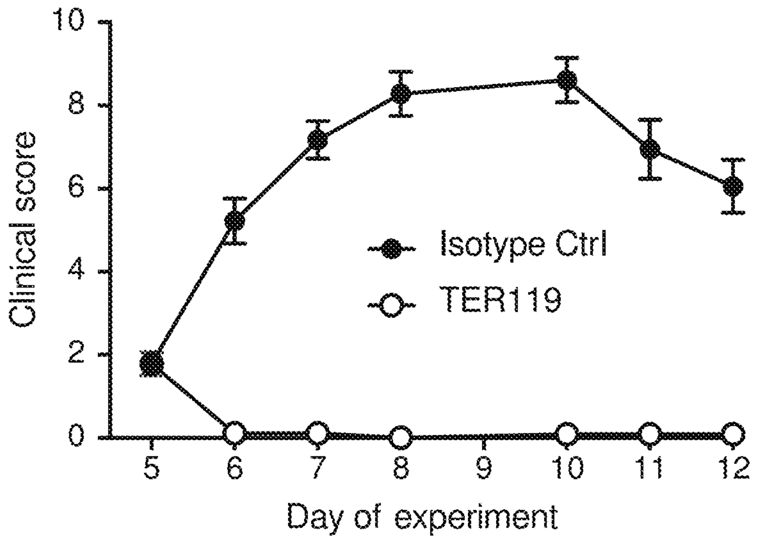
Figure 4:
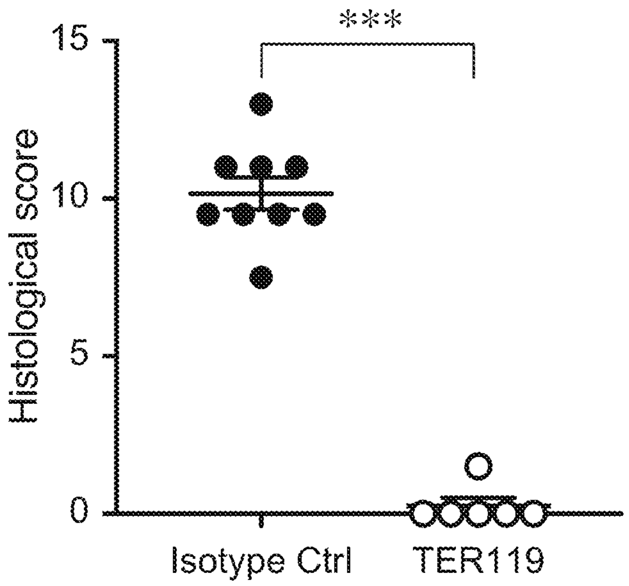
Figure 4:
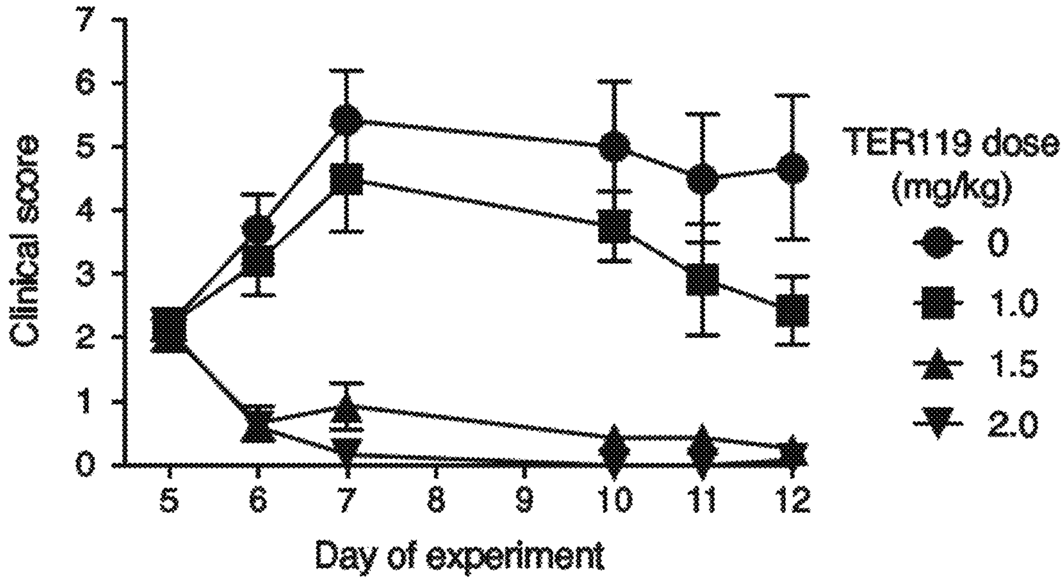
Figure 4:
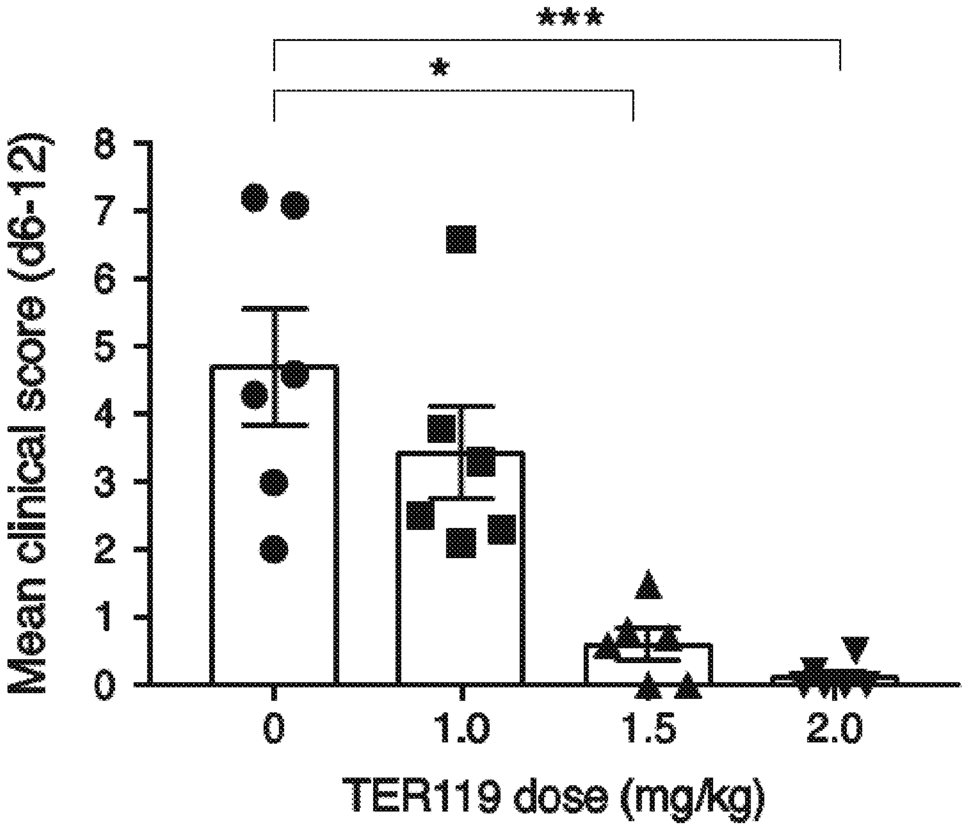
Figure 4:
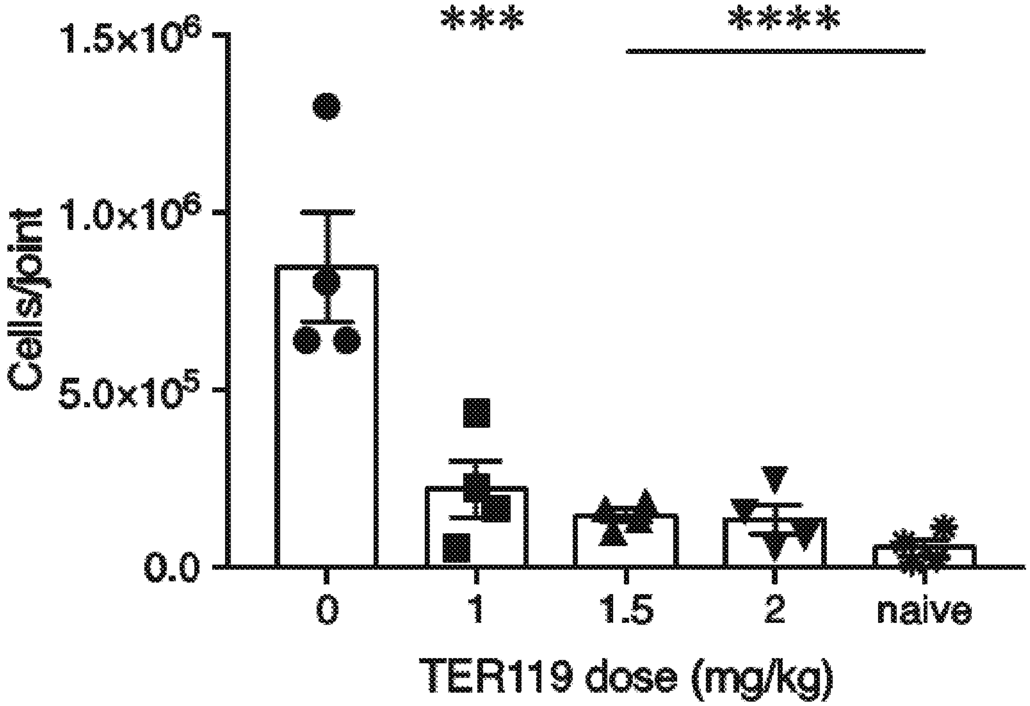
Figure 4:
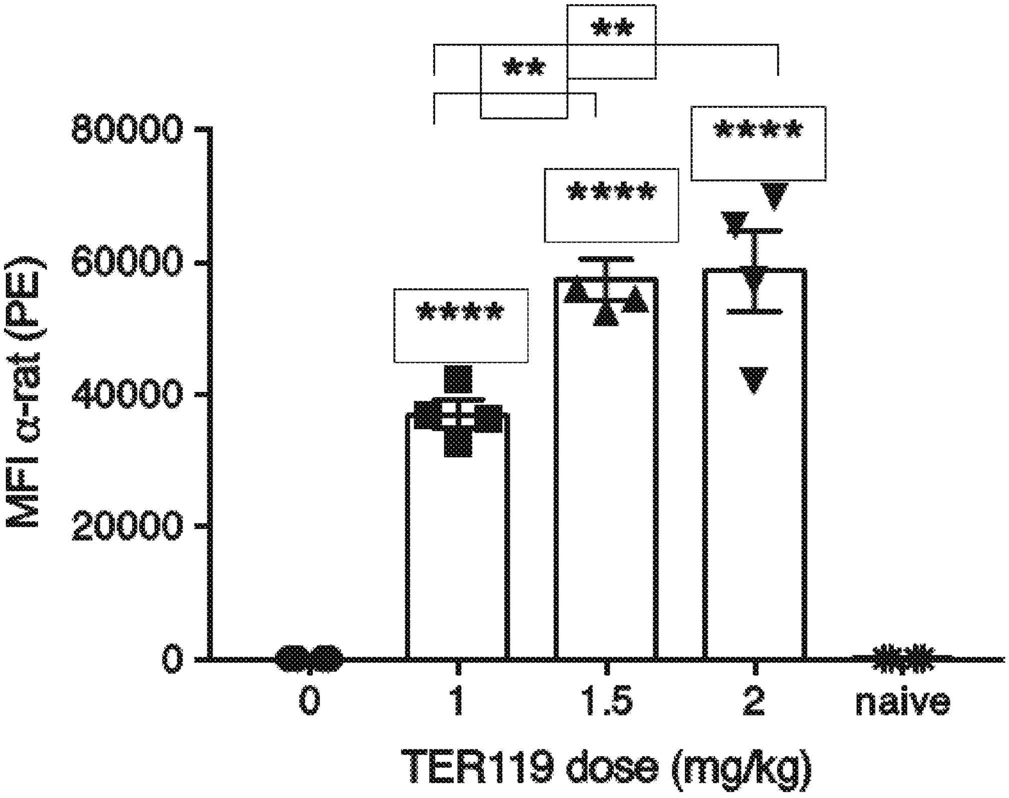
Figure 4:
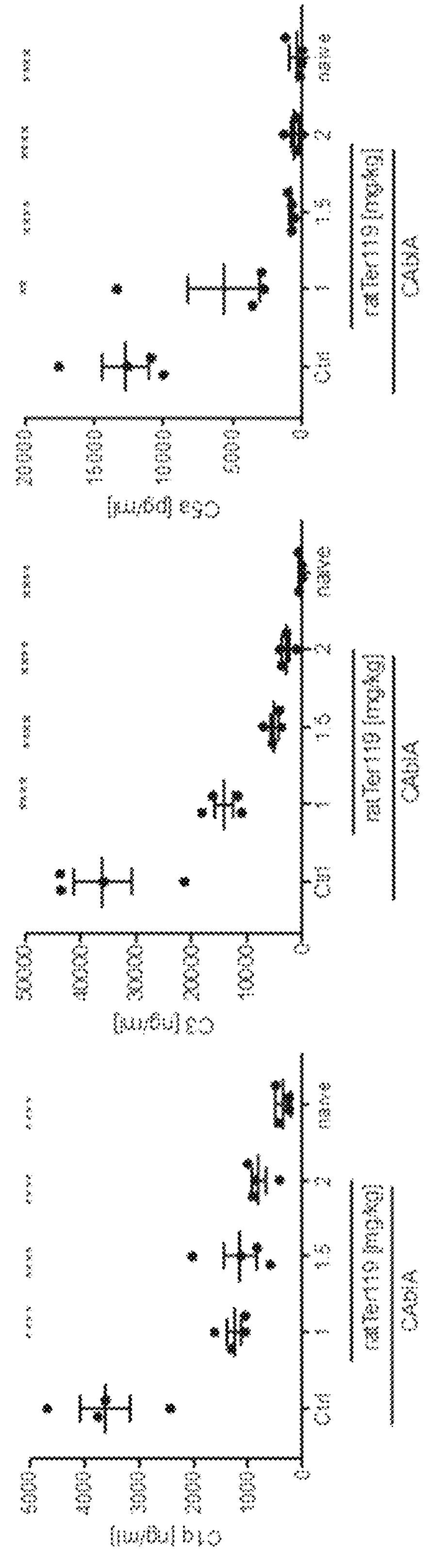
Figure 4:
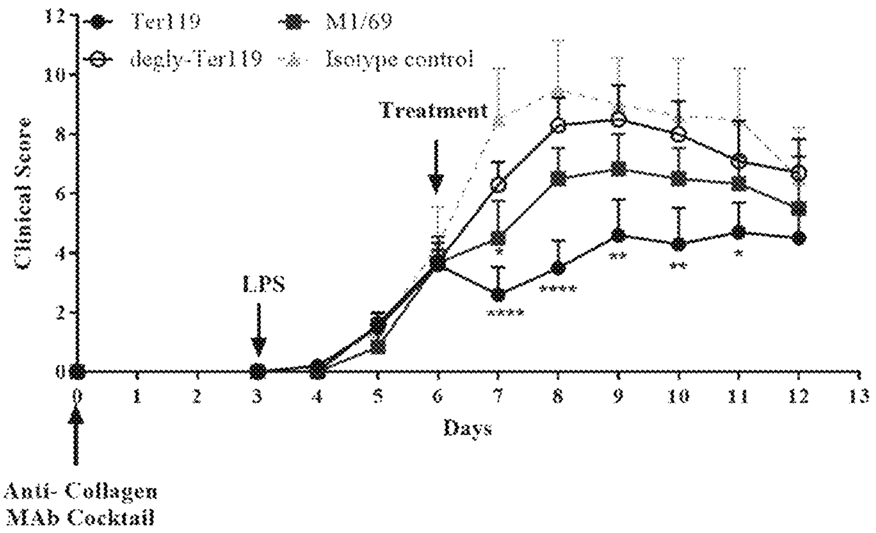
Figure 4:
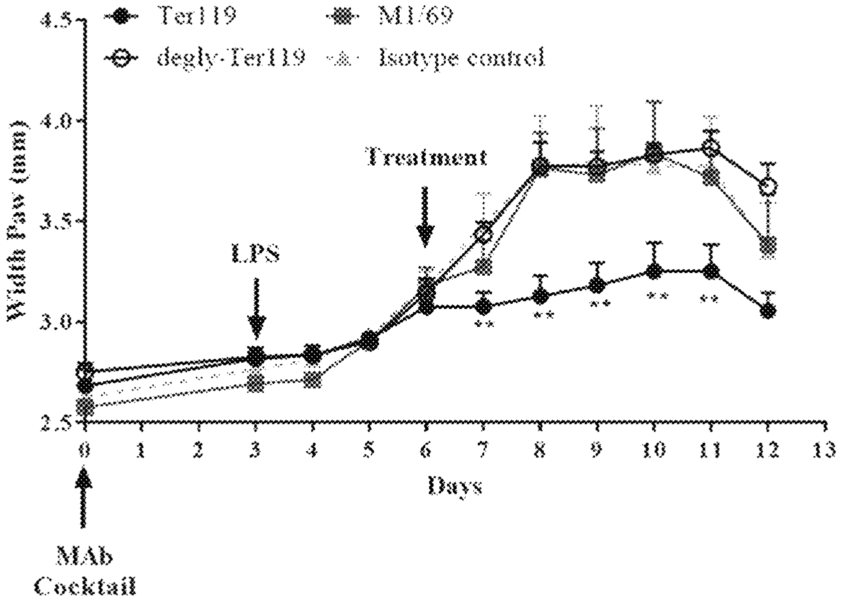
Figure 4:
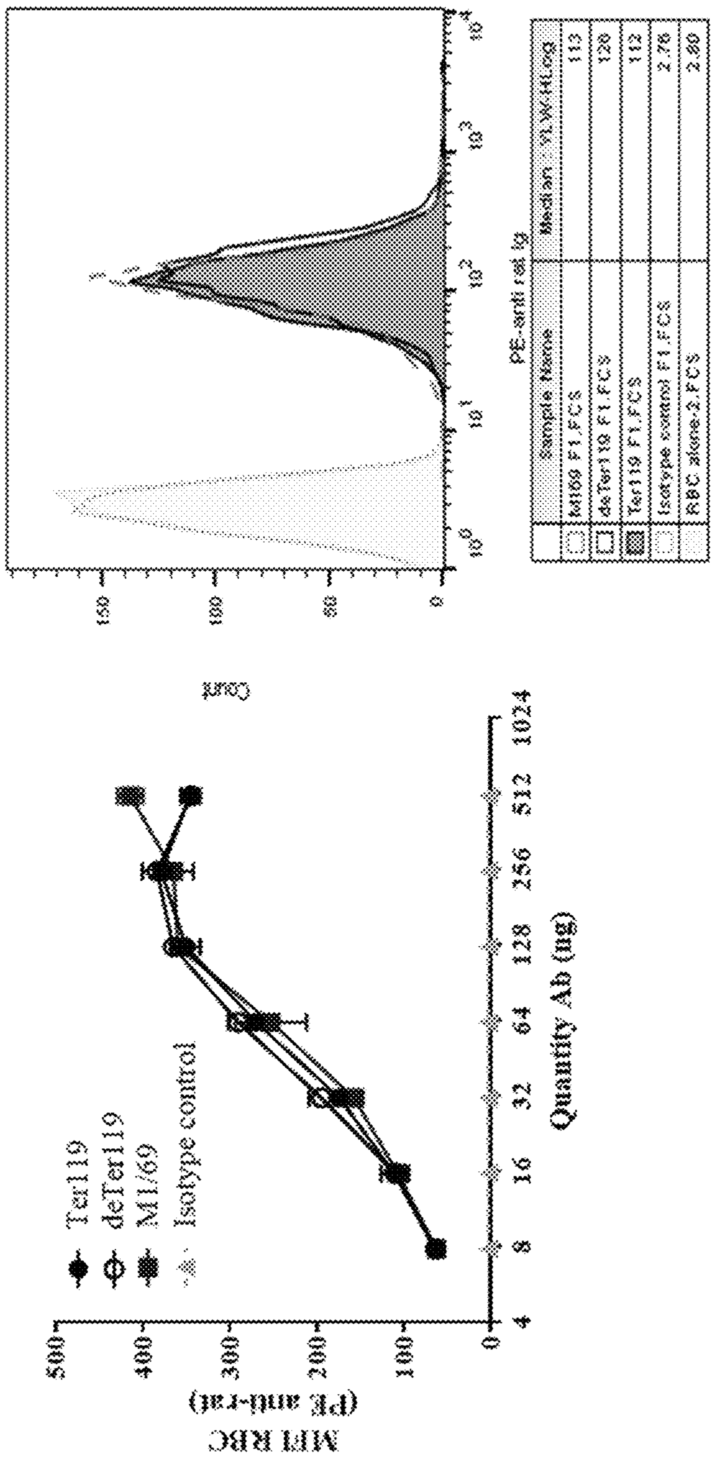

FIG. 4. Therapeutic effect of TER-119 on collagen Ab-induced arthritis (CAbIA).

(A) Mice with established CAbIA were treated on day 5 with a single i.v. injection of 2 mg/kg TER-119 or isotype control mAb (rat IgG2b). Clinical scores were assessed according to Campbell I K et al J Immunol. 2014;192:5031-5038). Data are means±SEM (n=9).

(B) Total histological scores of mice at day 12 of the experiment. Dots represent individual mice; bars show the means±SEM.***P<0.001, compared to isotype control, Mann-Whitney test (2-tailed).

(C) and (D) show effects of different doses of TER119 on clinical score in collagen Ab-induced arthritis (CAbIA).

(E) To assess the number of infiltrating cells in the joints, the patellas from each mouse were collected, digested and infiltrating leukocytes enumerated by visual count.

(F) TER119 at the 1 mg/kg dose results in significantly lower bound antibody on the surface of RBC compared to 1.5 and 2 mg/kg dose, which correlates to the clinical score.

(G) All doses of TER119 antibody reduce C1q, C3, C5a levels in the joint of arthritic mice. Complement components C1q (A), C3 (B), and C5a (C) assessed from the joint fluid by ELISA. Data were analysed by a one-way ANOVA test with Holm-Sidak's multiple comparison to the control group. *P<0.05; P<0.01; *P<0.001; ****P<0.0001.

(H) Mice with established CAbIA were treated on day 6 with TER-119, isotype control mAb, deglycosylated TER119 or M1/69. Clinical scores and paw width were assessed. The statistical comparisons were calculated using Two-way ANOVA with Dunnett's multiple comparisons test (all groups against isotype control).

Figure 5:
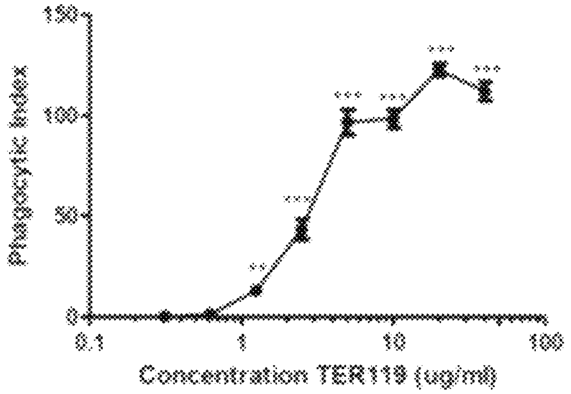

(I) Shows binding of the antibodies (0-512 ng of the primary antibody) with erythrocytes 25 from C57BL/6 mice, as assessed by flow cytometry FIG. 5. Dose dependent phagocytic index of TER-119 opsonized RBCs. Erythrocytes were acquired from C57B/6 mice and non-opsonized (control) or opsonized with various concentrations of TER-119 then incubated with RAW264.7 macrophages for 30 minutes. Phagocytic index was calculated by counting the total number of ingested RBCs and diving this by the total number of macrophages in a field and multiplying by 100 (n=5 per group). P<0.01, *P<0.001.

Figure 6:
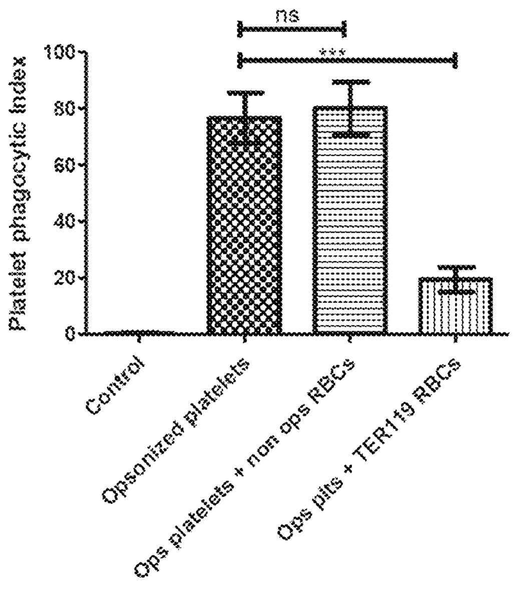

FIG. 6. Phagocytic index of platelets incubated with TER-119 opsonized erythrocytes. RAW 264.7 cells were cultured overnight, then platelets labelled with CMFDA and opsonized with Mwreg30 were either added to RAW cells with or without TER-119 opsonized RBCs for 30 minutes at 37° C. Platelet phagocytic index was calculated. ***P<0.05. (n=5 per group).

Figure 7:
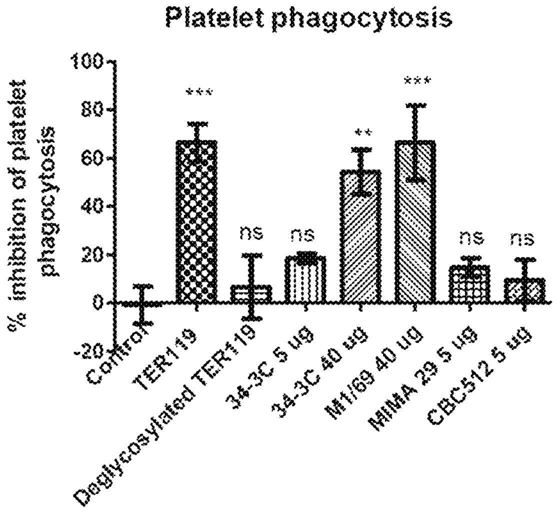

FIG. 7. Anti-erythrocyte antibody coated RBCs' ability to inhibit platelet phagocytosis. Erythrocytes were either non-opsonized or opsonized with antibody TER-119, deglycosylated TER-119, 34-3C (5 or 40 ug) and M1/69 for 1 hour then incubated with RAW 264.7 cells and MWReg30 opsonized CFMDA labelled platelets for 30 minutes. Cells were visualized by confocal microscopy and internalized platelets were counted by Imaris software version 8.0.2. (P<0.05). (n=4-6 per group).

Figure 8:
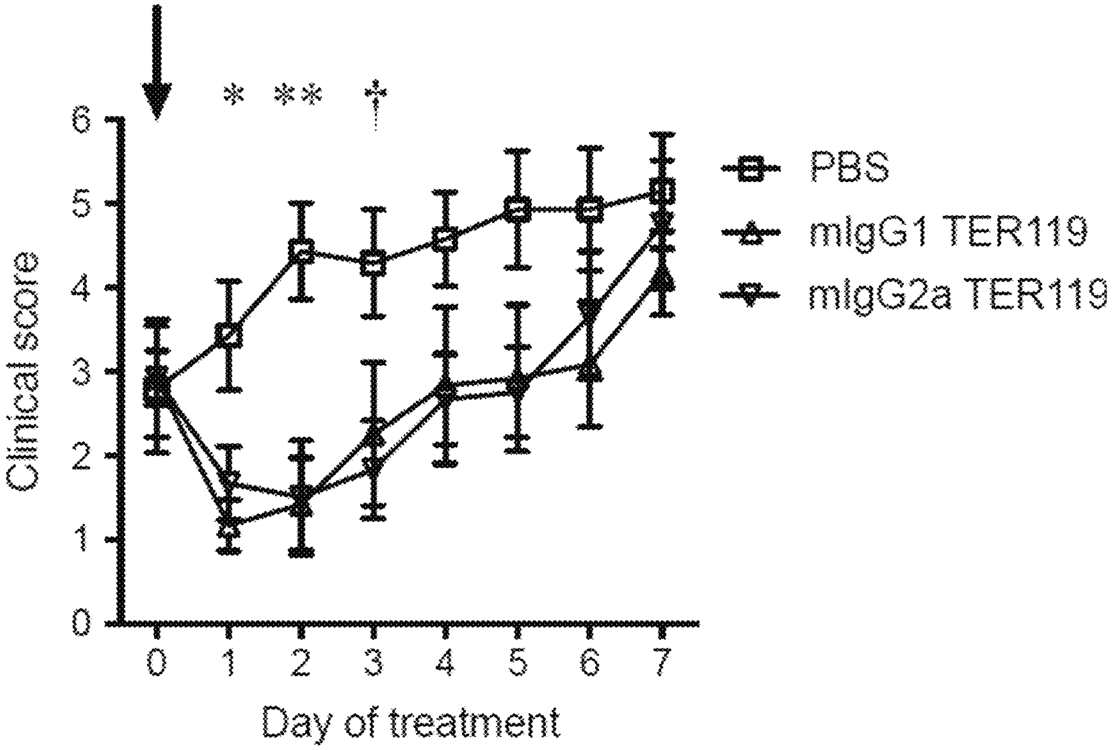

FIG. 8. 6 TER-119 expressed as murine IgG switch variants can treat a chronic model of collagen-induced arthritis (CIA) independent upon passive-antibody transfer. DBA-1 mice immunized against type II collagen were allowed to develop arthritis and then treated (timing as denoted by the arrow) with PBS (squares, n=7 mice), 2 mg/kg of TER-119 expressed as a murine IgG1subtype (triangles, n=6 mice) or expressed as a murine IgG2a subtype (downward triangles, n=6 mice) and arthritis clinical score evaluated over the course of the experiment.

Figure 9:
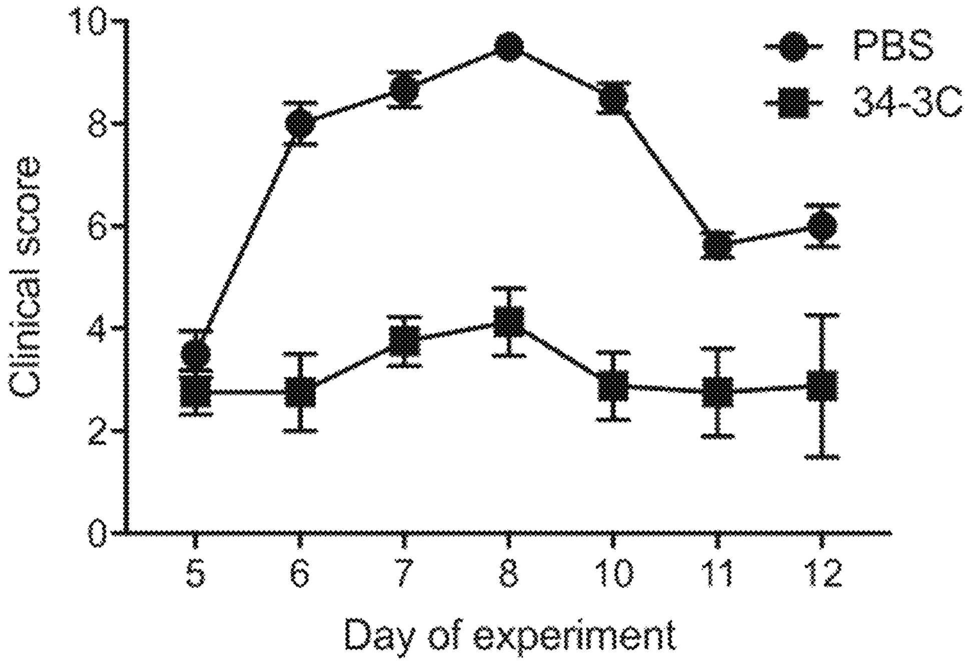
Figure 9:
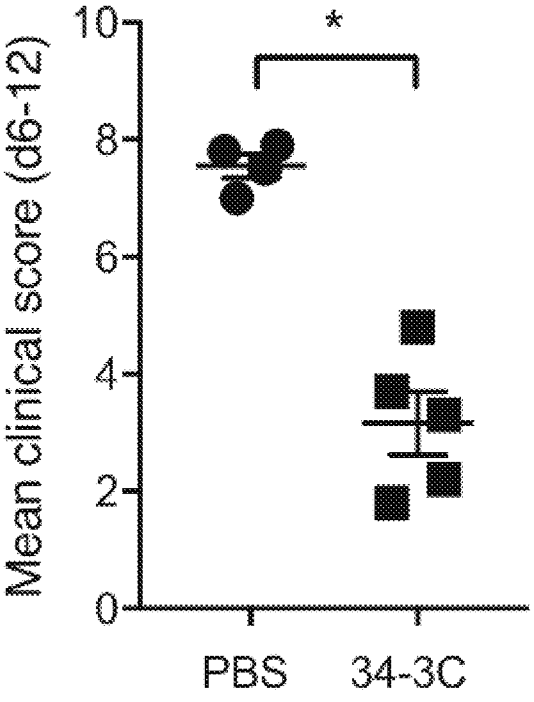

FIG. 9: Therapeutic effect of 34-3C (anti-Band 3 antibody) on collagen Ab-induced arthritis (CAbIA).

(A) Mice with established CAbIA were treated on day 5 with a single i.v. injection of 2 mg/kg anti-Band 3 mAb (clone 34-3C, mouse IgG2a) or PBS. Clinical scores were assessed according to Campbell I K et al J Immunol. 2014;192:5031-5038). Data are means±SEM (n=4/5).

(B) Average of clinical scores of mice between day 6 and 12 of the experiment. Dots represent individual mice; bars show the means±SEM. Data were analysed by Mann-Whitney test (2-tailed). *P<0.05.

DETAILED DESCRIPTION OF THE INVENTION

The present invention relates to the use of an antibody to a RBC in the treatment of inflammatory conditions, and is based on the inventors' surprising observation that an antibody to the RBC TER-119 antigen has an effect on the inflammatory condition immune thrombocytopenia (ITP) that occurs before the haemolytic effect of this antibody. It had previously been considered that the effect of this antibody and other RBC depleting antibodies on ITP occurred as a result of opsonised RBC clearance by the mononuclear phagocytic system (MPS), which competitively inhibits the depletion of platelets by the same pathway. However, this difference in timing between the effect on RBCs and the amelioration of ITP, as assessed by platelet enumeration, is supportive of the conclusion that the anti-RBC antibody has a broad anti-inflammatory activity, and hence that there is a utility for such antibodies that extends beyond ITP therapy to other diseases involving inflammation.

This existence of this broad anti-inflammatory activity is supported by the anti-RBC antibody's ability to ameliorate three separate inflammatory diseases that do not involve classical MPS function. Firstly, the anti-RBC antibody was able to prevent the induction of rheumatoid arthritis in the well-known and well-characterised K/B×N mouse model of rheumatoid arthritis, in which induction of arthritis occurs after serum transfer from a K/B×N mouse. This was shown by treating mice prophylactically with the anti-RBC antibody, prior to induction of the disease with K/B×N serum. There was a clear reduction in clinical arthritic score and in ankle width, two standard parameters for assessing RA in this mouse model (Mott P J, Lazarus A H (2013) PLoS ONE 8(6):e65805) in mice that had been prophylactically treated with the anti-RBC antibody, when compared to those who had not. In addition to this, the anti-RBC antibody was also able to ameliorate established arthritic disease, again based on the parameters of clinical arthritic score and ankle width. Treatment with the anti-RBC antibody 5 days after induction of disease with K/B×N serum reversed clinical scores and ankle widths to normal levels 3 days later.

The anti-RBC antibody was also capable of ameliorating inflammatory arthritis in the well-known and well characterised Collagen antibody induced arthritis (CAbIA) model in mice (the most commonly studied autoimmune model of rheumatoid arthritis) (Campbell IK et al J Immunol. 2014; 192:5031-5038. Campbell I K et al J Immunol. 2016;197: 4392-4402). Disease development in the CAbIA model is dependent on both FcγR engagement and activation of the complement system (Kagari T D et al J Immunol. 203;170 (8):4318-4324. Nandakumar K S et al Arthritis Res Ther. 2006;8(6):223). Induction of arthritis occurs after injection of an anti-collagen mAb cocktail and injection with LPS. This was shown by treating mice with the anti- RBC antibody, after induction of the disease. There was a clear difference between the treatment groups; the treated mice were completely protected from arthritis within 24 h of injection, and a reduction in histological score was observed in mice that had been treated with the anti-RBC antibody, when compared to those who had not.

In a further mouse model for an inflammatory disease, the anti-RBC antibody was able to prevent the induction of hypothermia that is observed following infusion of an MHC Class I antibody (34-1-2S) into SCID mice, as well as ameliorating pulmonary edema. This is a mouse model for human transfusion related acute lung injury (TRALI), which is one of the most serious complications of blood transfusion. The ability of the anti-RBC antibody to prevent systemic shock, as determined by the prevention of induction of hypothermia, and to ameliorate pulmonary edema in this inflammatory disease with symptoms disparate from those in ITP and arthritis provides additional support for a broad anti-inflammatory effect of the anti-RBC antibody.

Although IVIG has been used to treat ITP for over 30 years, and polyclonal anti-D can reverse thrombocytopenia in patients with ITP who express the D antigen (e.g. being sold as Rhophylac® for this treatment), the broad anti-inflammatory effect of anti-RBC antibodies has not previously been recognised. Work has been carried out to identify monoclonal antibodies to RBC that can be used in the treatment of ITP, and certain anti-RBC monoclonal antibodies such as the anti-TER-119 referred to above and an additional anti-CD24 antibody have been shown to be effective in mouse models (Song S et al Blood. 2003;101 (9):3708-3713), however, a small study in which a monoclonal anti-D antibody was tested in humans with ITP was not successful (Godeau, B. et al (1996) Transfusion;36(4): 328-330).

Much of the previous work on antibodies for the treatment of ITP thus focussed on the ability of such antibodies to opsonise RBC to prevent platelet destruction, specifically by providing competition for the MPS pathway. This new work by the inventors, however, opens up a new therapeutic area for antibodies to RBCs, in the treatment of inflammation more generally. The inventors have recognized that these insights offer novel opportunities for therapeutic intervention using an antibody which binds to a RBC, and which aims at reducing inflammation, increasing cure rates, prolongation of survival and/or progression-free survival in inflammatory disorders.

The invention thus provides an antibody to a RBC for use in a method of preventing or treating an inflammatory condition, as well as a method of preventing and treating an inflammatory condition in a subject, comprising administering to a subject in need thereof a therapeutically effective amount of an antibody to a RBC. It has been shown that a similar effect can be achieved with erythrocytes sensitized with anti-D antibodies in vitro and then introduced into the patient (Ambriz-Fernandez, R., et al. (2002) "Fc receptor blockade in patients with refractory chronic immune thrombocytopenic purpura with anti-D IgG" Arch Med Res 33(6): 536-540); therefore, the invention also provides administration of RBC sensitized with an antibody to a RBC for use in a method of preventing or treating an inflammatory condition, as well as a method of preventing and treating an inflammatory condition in a subject.

Inflammatory Conditions

The invention is concerned with the treatment and/or prevention of inflammatory conditions. By "inflammatory condition" it is meant any condition characterized by destructive inflammation which may be recurrent or chronic and is not associated with normal tissue repair. The inflammation may be chronic inflammation. In chronic inflammatory conditions, neutrophils and other leukocytes are constitutively recruited by cytokines and chemokines, leading to tissue damage.

Examples of inflammatory conditions are autoimmune conditions, i.e. diseases in which the immune system attacks the body's own tissues. Such diseases particularly include "autoinflammatory diseases" in which the body's immune system causes inflammation. Such conditions may be antibody mediated, and/or T-cell mediated, and/or mediated by the body's innate immune system. In one embodiment, antibodies of the present invention are used to treat an auto-antibody mediated autoimmune condition.

Inflammatory conditions may also be complement mediated (e.g. complement mediated inflammation in reperfusion injury, or spinal cord injury).

The inflammatory condition may be an autoimmune condition in which elevated IL-10 is present, such as a condition selected from arthritis, in particular rheumatoid arthritis, Kawasaki's disease, type I diabetes, multiple sclerosis, systemic lupus erythematosus (SLE).

Alternatively, the inflammatory condition may be an autoimmune condition in which elevated IL-10 is not present, e.g. in which there are normal levels of IL-10, or in which IL-10 is reduced. ITP patients and autoimmune thyroiditis patients have lower levels of IL-10 than controls.

The disease can be, for example, inflammation associated with changes in temperature, autoimmune cytopenia (e.g. autoimmune haemolytic anaemia (AIHA), autoimmune neutropenia (AIN), autoimmune thrombocytopenia (ITP)), primary antiphospholipid syndrome, arthritis (e.g. rheumatoid arthritis, juvenile arthritis), bowel disease (e.g. ulcerative colitis, Crohn's disease, coeliac disease), Kawasaki disease, SLE, immune thrombocytopenia purpura, ischemia/reperfusion injury, Type I diabetes, inflammatory skin disorders (e.g. acne, psoriasis, lichen planus, pemphigus, pemphigoid), autoimmune thyroid disease (e.g. Graves' disease, Hashimoto' s thyroiditis), Sjogren's syndrome, pulmonary inflammation (e.g. asthma, chronic obstructive pulmonary disease (COPD), pulmonary sarcoidosis, lymphocytic alveolitis), transplant rejection, spinal cord injury, brain injury (e.g., stroke, traumatic brain injury), neurodegenerative diseases (e.g. Alzheimer's disease, Parkinson's disease, Lewy body disease), other neurological conditions (progressive multifocal leukoencephalopathy, ALS, chronic inflammatory demyelinating polyneuropathy (CIDP), inflammatory neuropathy, Guillain-Barre syndrome (GBS), motor neuron diseases (MND), multiple sclerosis, myasthenia gravis, neuromyelitis optica (NMO), other autoimmune channelopathies), gingivitis, gene therapy-induced inflammation, diseases of angiogenesis, inflammatory kidney disease (e.g., IgA nephropathy, membranoproliferative glomerulonephritis, rapidly progressive glomerulonephritis), Stevens-Johnson syndrome, autoimmune epilepsy, muscle inflammation (e.g. dermatomyositis and polymyositis), scleroderma, and atherosclerosis.

Of particular interest are lung injuries (such as acute lung injury, transfusion related acute lung injury (TRALI)), autoimmune cytopenia, idiopathic thrombocytopenic purpura/immune cytopenia (ITP), rheumatoid arthritis, systemic lupus erythematosus, asthma, Kawasaki disease, Guillain-Barre syndrome, Stevens-Johnson syndrome, Crohn's disease, colitis, diabetes (e.g. type 1 or type 2 diabetes), chronic inflammatory demyelinating polyneuropathy (CIDP), inflammatory neuropathy, neuromyelitis optica (NMO), other autoimmune channelopathies, autoimmune epilepsy, myasthenia gravis, dermatomyositis, polymyositis, scleroderma, vasculitis, uveitis, pemphigus, pemphigoid, spinal cord injury or Alzheimer's disease.

In some embodiments the inflammatory condition is a neurological condition, e.g. a neurological autoimmune disease. Examples of such conditions include chronic inflammatory demyelinating polyneuropathy (CIDP), myasthenia gravis (MG), multiple sclerosis (MS), neuromyelitis optica (NMO), or autoimmune epilepsy.

In some embodiments the inflammatory condition is selected from arthritis (e.g. rheumatoid arthritis) and TRALI.

In some embodiments the inflammatory condition is not ITP, or is not ITP or autoimmune thyroiditis. In other embodiments the inflammatory condition is not a disease where IL-10 is decreased, or is not a disease in which there are normal levels of IL-10.

IL-10 levels may be measured using standard immunoassay (e.g. ELISA) kits that are known in the art. The levels may be measured in any appropriate sample e.g. blood, serum, plasma, urine, cerebrospinal fluid and therefore where the levels of IL-10 are referred to herein it is the level in that sample that is relevant. Comparisons can be made with normal, e.g. healthy subjects.

Biological Readout/Effects of Treatment

Without being bound by any particular theory, the inventors believe that the use of an anti-RBC antibody according to the invention is useful to: (i) reduce inflammation in inflammatory conditions (ii) reduce and/or delay the clinical manifestation of the condition (which may be effects of inflammation in inflammatory conditions), (iii) extend survival of a subject with an inflammatory condition, (iv) enhance quality of life of a patient suffering from such a condition, (v) enhance the convenience of therapy for the patient, and/or (vi) enhance the efficacy of other drugs used to treat an inflammatory condition.

A method of treating an inflammatory condition is provided, said method comprising administering to the subject an effective amount of an antibody to a RBC. In some embodiments the method of the invention can be described as a method of reducing inflammation in an inflammatory condition, a method of reducing and/or delaying the clinical manifestation of the condition (e.g. the effects of inflammation in an inflammatory condition), a method of extending survival of a subject with an inflammatory condition, a method of enhancing quality of life of a patient suffering from such a condition, enhancing the convenience of therapy for the patient, and/or a method of enhancing the efficacy of one or more other drug used to treat an inflammatory condition, wherein in each case said method comprises administering to the subject in need thereof an effective amount of an antibody to a RBC.

The method of the invention may also be described as a method of treating or preventing one or more of the symptoms of an inflammatory condition, optionally treating one or more of the symptoms of an inflammatory condition, said method comprising administering to a subject in need thereof an effective amount of an antibody to a RBC.

Likewise an antibody to a RBC for use in these methods is provided, as is the use of antibody to a RBC in the manufacture of a medicament for carrying out such methods.

(i) Reduction of Inflammation in Inflammatory Conditions

The method of the invention can be described as a method of reducing inflammation in an inflammatory condition. In some embodiments, inflammation, and its effects in inflammatory conditions are assessed by standard clinical tests known in the art.

For example, disease markers are known for inflammatory conditions. The marker or markers that are used to assess the status of the disease may be a marker or a group of markers specific for the relevant disease (referred to her as a "disease marker") or may be a marker of inflammation (referred to here as an "inflammatory marker"). Examples of suitable samples for assessment include tissue, blood and urine.

Levels of one or more inflammatory markers can be assessed in a subject to provide information about the status of the inflammatory disease and about the effect of any treatment on the disease. A reduction in inflammatory markers is in general an indication of a reduction in inflammation. A biological sample can be taken from a subject at various time points (e.g. before treatment is commenced and at suitable time points after administration of the antibody of the invention) and the levels of one or more inflammatory markers can be assessed to determine the effect of the treatment on inflammation in the subject. Examples of inflammatory markers that are well known for such purposes include CRP, IL-6 and TNF-α. In one embodiment one or more inflammatory marker is reduced in the subject after administration of the antibody of the invention compared to the level of the marker before administration of the antibody of the invention. In another embodiment of the invention the method further comprises the step of determining the level of one or more inflammatory marker in the subject, and this may be before and/or after treatment.

Any reduction is preferably statistically significant. Reduction in one or more of the above markers may be by at least 5, 10, 15, 20, 25, 30, 35, 40, 45, 50% compared to the level before treatment.

(ii) Reduction and/or Delay to the Clinical Manifestation of the Inflammatory Condition (e.g. Effects of Inflammation in Inflammatory Conditions)

The method of the invention can be described as a method of reducing of the clinical manifestation of the inflammatory condition (e.g. effects of inflammation in inflammatory conditions). In some embodiments, levels of one or more disease markers can be assessed in a subject to provide information about the status of the disease and about the effect of any treatment on the disease. In many conditions the clinical manifestations of the disease arise as a result of inflammation and the associated tissue damage, but other mechanisms are also known.

Certain disease markers are known and are used by clinicians to diagnose and monitor inflammatory conditions. In general, a reduction in the level of a disease marker may be an indication of a reduction in severity of the disease (although in certain circumstances an increase in one or more disease markers may be an indication of a reduction in severity of the disease). A biological sample can be taken from a subject at various time points (e.g. before treatment is commenced and at suitable time points after administration of the antibody of the invention) and the levels of one or more disease markers can be assessed to determine the effect of the treatment on inflammation in the subject. Examples of disease markers that are known for such purposes are set out in Table 1 below. In one embodiment one or more disease marker is reduced (or increased) in the subject after administration of the antibody of the invention compared to the level of the marker before administration of the antibody of the invention. In certain embodiments the reduction (for example, inflammatory cytokines or chemokines) or increase (for example anti-inflammatory cytokines or anti-inflammatory chemokines) is associated with a decrease in severity of the disease. In another embodiment of the invention the method further comprises the step of determining the level of one or more disease marker in the subject, and this may be before and/or after treatment.

TABLE 1

| Disease | Blood disease markers |
|---|---|
| Rheumatoid arthritis (RA) | Rheumatoid Factor (RF) (auto-antibody directed against the Fc portion of immunoglobulin found in the blood of about 80 percent of people with rheumatoid arthritis). |
| | Anti-cyclic citrullinated peptide antibody (anti-CCP) |
| | Protein biomarker 14-3-3eta |
| MG | Anti-acetylcholine receptor antibody (anti-AChR Ab) |
| | Anti-muscle-specific tyrosine kinase antibody (anti-MuSK Ab) |
| Systemic lupus erythematosus (SLE) | Anti-nuclear antibody |
| | anti-double stranded DNA (dsDNA) antibodies |
| | anti-U1 RNP (U1 spliceosomal RNA) |
| | anti-histone antibodies |

Any reduction or increase in such markers is preferably statistically significant. Reduction or increase in one or more of the above markers may be by at least 5, 10, 15, 20, 25, 30, 35, 40, 45, 50% e.g. compared to the level before treatment.

The effects of inflammation can also be assessed by standard clinical tests that are known in the art. Clinical tests may involve scoring which is carried out on the basis of the clinical manifestation of the disease or disorder that is to be treated. The treatment in one embodiment results in an improvement in the clinical score of the disease compared to the clinical score of the disease before administration of the antibody of the invention. This is analogous with the improvements seen in appropriate animal models, such as improvements in clinical score and a reduction in ankle size that is observed in the K/B×N mice in Examples 3 and 4 following treatment with the antibody of the invention, with the prevention of 34-1-2S induced hypothermia in Example 6, and with the improvements in clinical and histological score that is observed in the CAbIA mice in Example 5.

The improvement may be manifest in a reduction in the clinical manifestation or severity of the inflammatory condition, or a delay in the clinical manifestation of the inflammatory condition, so that the treatment affects the time course of the disease progression.

(iii) Extending Survival of a Subject with an Inflammatory Condition

The method of the invention can be described as a method of extending survival of a subject with an inflammatory condition. Many inflammatory conditions, and particularly autoimmune conditions have no cure and result in a subject having a decreased life expectancy when compared to subject who does not have such a condition. The treatment can therefore extend the survival of a subject with an inflammatory condition, e.g. by at least 1, 2, 5, 10 months or years.

(iv) Enhancing the Efficacy of Other Drugs Used to Treat an Inflammatory Condition The method of the invention can be described as a method of enhancing the efficacy one or more other drug used to treat an inflammatory condition. Known methods of treating inflammatory conditions include three general approaches, immunosuppressive, anti-inflammatory, or palliative treatments. Examples of anti-inflammatories include anti-inflammatory pain reliever drugs (NSAIDs, e.g. aspirin, ibuprofen). Corticosteroids (such as prednisone and prednisolone), aminosalicylates, immunosuppressant drugs such as azathioprine, mercaptopurine, and methotrexate are also used. Biologic therapies with targets including cytokines, B cells, and co-stimulation molecules are now being used. Cytokine targets include tumor necrosis factor (TNF)-alpha (e.g. infliximab, adalimumab and golimumab), interleukin (IL)-1, anti-IL-6 molecules. B-cell depletion includes use of anti-CD20 antibodies (e.g. Rituximab) and B cell receptor (BCR) modulation by the B-lymphocyte stimulator (BLyS) (Belimumab).

The antibody of the invention can thus be used in combination with one or more other anti-inflammatory drug to enhance the efficacy of the other anti-inflammatory drug. Likewise, the other anti-inflammatory drug may enhance the efficacy of the antibody of the invention.

Red Blood Cell Antibody

A red blood cell (RBC) antibody binds to a RBC. The molecule to which the RBC antibody binds is referred to herein as a RBC molecule. This is therefore a RBC surface molecule, i.e. a molecule that is found on or associated with the outer surface of a RBC, so that the antibody to the RBC binds to an intact RBC. A list of proteins that have been identified in the erythrocyte membrane fraction is shown below; the RBC molecule suitable for use in the present invention may be selected from this list (Table 2).

TABLE 2

(from Kakhniashvili, DG et al Mol Cell Proteomics. 2004; 3(5): 501-509)
Proteins identified in RBC membrane fractions

| No. | Protein description | Molecular mass (Da) | GI Number | Sequence coverage (%) | No. of identified peptides |
|---|---|---|---|---|---|
| 1 | Spectrin α chain, erythrocyte | 279,916.5 | 1174412 | 48.0 | 77* |
| 2 | Spectrin β chain, erythrocyte | 246,468.1 | 17476999 | 48.0 | 76* |
| 3 | Ankyrin 1, splice form 2 | 208,067.9 | 105397 | 45.0 | 55 |
| 4 | Ankyrin 1, isoform 4, erythrocytic | 209,416.6 | 10947036 | 45.0 | 50 |
| 5 | Ankyrin 1, isoform 2, erythrocytic | 189,011.2 | 10947042 | 46.0 | 48 |
| 6 | Similar to ankyrin 1 | 206,254.8 | 13645508 | 51.0 | 48 |
| 7 | Protein band 4.2, erythrocytic | 70,946.5 | 107446 | 33.0 | 21 |
| 8 | Protein band 4.1 (elliptocytosis 1, RH-linked) | 66,398.5 | 4758274 | 45.0 | 17 |
| 9 | Protein band 3, erythrocytic | 101,792.3 | 4507021 | 28.0 | 17 |
| 10 | Protein band 4.1, erythrocytic | 97,016.9 | 14916044 | 32.0 | 16 |
| 11 | Actin β chain | 41,812.8 | 461515 | 47.0 | 12* |
| 12 | Flotillin 1, erythrocytic | 47,355.3 | 5031699 | 47.0 | 12 |
| 13 | Membrane protein p55, erythrocytic, (palmitoylated) | 52,296.5 | 4505237 | 35.0 | 11 |
| 14 | Flotillin 2 | 47,142.3 | 13567629 | 29.0 | 11 |
| 15 | Protein band 4.0 (dematin), erythrocytic | 45,514.4 | 13623437 | 40.0 | 10 |
| 16 | Protein band 7.2b, stomatin | 32,598.8 | 1103842 | 47.0 | 10 |
| 17 | Glyceraldehyde-3-phosphate dehydrogenase | 38,054.2 | 31645 | 51.0 | 10 |
| 18 | Tropomyosin 3, cytoskeletal | 29,032.7 | 136096 | 55.0 | 10 |
| 19 | Solute carrier family 2 (facilitated glucose transporter), member 1 | 54,117.8 | 5730051 | 13.0 | 6 |
| 20 | Similar to flotillin 2 | 42,565.0 | 13277550 | 15.0 | 6 |
| 21 | Tropomyosin isoform | 28,420.1 | 1062876 | 36.0 | 6 |
| 22 | Glucose transporter glycoprotein | 37,879.6 | 3387905 | 17.0 | 5 |
| 23 | Tropomyosin α chain (smooth muscle) | 26,576.7 | 136100 | 37.0 | 5 |
| 24 | Actin α 2, aortic smooth muscle | 42,108.1 | 1070613 | 20.0 | 5 |
| 25 | Adducin α subunit, erythrocyte | 80,955.1 | 12644231 | 10.0 | 5* |
| 26 | Rabphilin-3 A-integrating protein | 80,858.2 | 1082757 | 8.0 | 5* |
| 27 | C-1-tetrahydrofolate synthase, cytoplasmic | 101,559.2 | 115206 | 6.0 | 4 |
| 28 | Translation initiation factor 2C, 2 | 66,252.2 | 18570004 | 10.0 | 4 |
| 29 | Aldolase A | 39,288.8 | 229674 | 17.0 | 4 |
| 30 | Tropomodulin | 40,569.2 | 4507553 | 16.0 | 3* |
| 31 | RAP2B, member of RAS oncogene family | 20,504.4 | 11433346 | 43.0 | 3 |
| 32 | Arginase type 1 erythroid variant | 35,664.1 | 18535612 | 12.0 | 3 |
| 33 | Arginase type 1 | 34,734.9 | 10947139 | 12.0 | 3 |
| 34 | Creatine kinase, muscle | 43,101.1 | 14763181 | 21.0 | 3 |
| 35 | B-CAM protein | 63,566.7 | 2134796 | 8.0 | 3 |
| 36 | ATP-binding cassette half-transporter | 99,712.3 | 11245444 | 5.0 | 2 |
| 37 | RAP1A, member of RAS oncogene family or | 20,997.1 | 4506413 | 14.1 | 2 |
| | RAP1B | 20,824.7 | 7661678 | 14.1 | 2 |
| 38 | Calcium tansporting ATPase 4 | 137,920.2 | 14286105 | 2.5 | 2 |
| 39 | Rh blood D group antigen polypeptide | 45,136.5 | 10800054 | 4.0 | 2 |
| 40 | Channel-like integral membrane protein | 16,239.5 | 1314306 | 15.0 | 2 |
| 41 | Glycophorin A precursor | 16,429.6 | 1070638 | 21.0 | 2 |
| 42 | Solute carrier family 29 (nucleoside transporter), member 1 | 50,219.4 | 4826716 | 3.5 | 2 |
| 43 | Glycophorin A | 14,784.8 | 106140 | 23.0 | 2 |
| 44 | Glutathione transferase | 27,053.4 | 809436 | 19.0 | 2 |
| 45 | Glyphorin C, Isoform 1 | 13,810.6 | 4504229 | 20.0 | 1 |
| 46 | Aquaporin 1 | 28,526.0 | 4502177 | 7.0 | 1 |
| 47 | Erythroblast membrane-associated protein | 52,604.8 | 17480129 | 3.0 | 1 |
| 48 | Similar to glycophorin A | 16,371.6 | 13529077 | 20.0 | 1 |
| 49 | Cell surface glycoprotein CD44 | 39,433.8 | 7512338 | 4.0 | 1 |
| 50 | Vesicle-associated membrane protein 2 (synaptobrevin 2) | 12,648.7 | 7657675 | 15.0 | 1 |
| 51 | Similar to adhesive plaque matrix protein precursor | 106,879.1 | 17481669 | 1.0 | 1 |
| 52 | Poly (A)-specific ribonuclease | 73,451.0 | 4505611 | 3.0 | 1 |
| 53 | Similar to RAS-related protein RAL-A | 23,566.8 | 14740792 | 7.0 | 1 |
| 54 | Presenilin-associated protein | 39,862.4 | 6409316 | 6.0 | 1 |
| 55 | Duodenal cytochrome b | 31,611.2 | 13376257 | 3.5 | 1 |
| 56 | bA421H8.2 (novel protein) | 16,743.7 | 17402228 | 9.0 | 1 |
| 57 | Similar to RAS-related protein RAB-15 | 23,517.9 | 18596861 | 5.0 | 1 |
| 58 | CD59antigenp18-20 | 17,067.4 | 17473237 | 5.0 | 1 |
| 59 | Rhesus D category VI type III protein | 45,247.7 | 2765839 | 1.9 | 1 |
| 60 | RAB 35, RAS oncogene family | 23,025.2 | 5803135 | 6.0 | 1 |
| 61 | Ral A binding protein | 75,063.4 | 5803145 | 2.1 | 1 |
| 62 | Hypothetical protein XP_100510 | 8,049.3 | 18577723 | 16.0 | 1 |
| 63 | ATP-binding cassette, subfamily C, member 6 | 164,904.4 | 6715561 | 0.9 | 1 |
| 64 | Phosphoribosyl pyrophosphate synthetase | 34,834.2 | 4506127 | 7.0 | 1 |
| 65 | Unknown protein | 46,884.2 | 18089137 | 3.6 | 1 |
| 66 | Similar to Lutheran blood group | 59,287.7 | 18589892 | 3.1 | 1 |
| 67 | Phosphatidylinositol-4-phosphate 5 kinase, type III | 46,078.6 | 1730569 | 4.4 | 1 |
| 68 | Hypothetical protein XP_100685 | 35,877.6 | 18604339 | 7.0 | 1 |
| 69 | Hypothetical protein XP_100619 | 18,587.6 | 18604359 | 15.0 | 1 |

TABLE 2-continued (from Kakhniashvili, DG et al Mol Cell Proteomics. 2004; 3(5): 501-509)
Proteins identified in RBC membrane fractions

| No. | Protein description | Molecular mass (Da) | GI Number | Sequence coverage (%) | No. of identified peptides |
|---|---|---|---|---|---|
| 70 | Block of proliferation 1 | 83,629.5 | 23830903 | 1.5 | 1 |
| 71 | Similar to tropomyosin | 10,804.3 | 18590249 | 13.0 | 1 |
| 72 | Hypothetical protein XP_061743 or | 48,719.0 | 17472555 | 2.5 | 1 |
| | XP_089854 | 31,487.0 | 18577194 | 4.0 | 1 |
| 73 | Hypothetical protein XP_106269 | 12,703.8 | 18558481 | 22.0 | 1 |
| 74 | Hypothetical protein XP_100925 | 22,863.4 | 18601384 | 8.0 | 1 |
| 75 | Zone pellucida binding protein | 40,169.8 | 5002116 | 3.4 | 1 |
| 76 | 2',3'-cyclic-nucleotide 3'-phosphodiesterase | 4,242.9 | 7435185 | 60.0 | 1 |
| 77 | Lyn B protein | 58,033.3 | 2117805 | 4.3 | 1 |
| 78 | KIAA0340 | 117,819.0 | 2224621 | 2.1 | 1 |
| 79 | Hypothetical protein XP_091724 | 144,900.8 | 18588504 | 1.1 | 1 |
| 80 | Hypothetical protein XP_091430 | 27,641.2 | 18588504 | 5.0 | 1* |
| 81 | Similar to tropomyosin 4 | 18,426.8 | 14729747 | 6.0 | 1* |
| 82 | HGTD-P | 17,342.4 | 9295192 | 10.0 | 1* |
| 83 | Hypothetical protein XP_095919 | 291,206.1 | 18572484 | 0.6 | 1* |
| 84 | Far upstream element binding protein | 87,534.4 | 1082624 | 2.5 | 1* |
| 85 | Hypothetical protein XP_103707 | 13,374.6 | 16551105 | 12.0 | 1* |
| 86 | Hypothetical protein XP_092517 | 41,409.4 | 18552304 | 2.6 | 1* |
| 87 | Enhancer protein | 41,289.8 | 1345400 | 4.6 | 1* |
| 88 | Hypothetical protein | 15,770.3 | 18551738 | 12.0 | 1* |
| 89 | KIAA1741 protein | 123,305.7 | 12698027 | 1.7 | 1* |
| 90 | Ig heavy chain V-V region | 10,995.4 | 87863 | 16.0 | 1* |
| 91 | DC 38 | 31,691.4 | 12005984 | 4.7 | 1* |

*The proteins found primarily in the low-ionic-strength spectrin extract from RBC membranes.

The RBC molecule may be attached directly or indirectly to the RBC membrane. Direct attachment of the molecule to the RBC membrane may occur as a result of the molecule being a transmembrane protein or a transmembrane glycoprotein, or directly attached to a lipid in the membrane. Indirect attachment of the molecule to the RBC may occur as a result of the molecule being bound to or associated with a molecule that is itself directly attached to the membrane (e.g. a membrane protein or glycoprotein or a protein or carbohydrate that is attached to one or more lipids in the membrane).

The RBC antibody thus binds to a RBC molecule, i.e. a RBC surface molecule, which may be a protein (e.g. a glycoprotein) or a carbohydrate, but is typically a protein (e.g. a glycoprotein). In some instances, the RBC molecule is not glycosylated.

The RBC surface molecule can also be described as a RBC antigen, however the RBC antibody need not distinguish between different isoforms of a RBC molecule such as the different isoforms of a RBC molecule that give rise to different blood groups. In other words, the RBC antibody may in some embodiments bind to more than one isoform (e.g. 2 or more, 3 or more, 4 or more isoforms) of the RBC molecule, e.g. wherein the RBC molecule has multiple isoforms that are associated with different blood groups. In such a case the antibody does not distinguish between different blood groups that arise as a result of polymorphisms in the RBC molecule. Alternatively, the RBC antibody may bind only to one isoform of the RBC molecule, so that it can distinguish between different blood groups that arise as a result of polymorphisms in the RBC molecule.

Certain RBC molecules may take different forms in different individuals, and these differences may be associated with different blood groups. For example, a protein or glycoprotein molecule may have multiple possible isoforms, wherein the different isoforms are associated with different blood groups. An example of a blood group that is based on different protein antigens is the Rhesus system. The Rhesus D protein is either present or absent, so that a given individual is RhD positive or negative, but the associated Rhesus CE protein may be present in several forms that arise as a result of amino acid polymorphisms at only five amino acid locations. The different forms of the Rhesus CE protein are associated with different Rhesus blood types and may be referred to as being different antigens. Thus, in the case of RBC molecules such as the Rhesus CE protein, where different isoforms of the protein exist, the RBC antibody may bind to all isoforms of the protein or may bind only to certain isoforms.

Likewise, different carbohydrate based blood group antigens exist. The "ABO" antigens are carbohydrate chains that are attached to numerous different proteins and lipids that lie in the RBC membrane. The ABO locus has three main allelic forms: A, B, and O. The A and B alleles each encode a glycosyltransferase that catalyses the final step in the synthesis of the A and B antigen, respectively. The A/B polymorphism arises from several SNPs in the ABO gene, which result in A and B transferases that differ by four amino acids. The O allele encodes an inactive glycosyltransferase that leaves the ABO antigen precursor (the H antigen) unmodified, whereas the A and the B antigens differ in the carbohydrate structure. The ABO antigens may be present on multiple RBC molecules. The different forms of the carbohydrate are associated with different blood types and may be referred to as being different antigens. Thus, in the case of RBC molecules that contain the ABO antigen, where different carbohydrate structures are associated with different blood types, the RBC antibody may bind only to certain carbohydrate structures or may bind to all forms of the RBC molecule (e.g. by binding to the protein portion of the RBC molecule).

In some embodiments the RBC molecule is not a molecule, the presence or absence of which or the presence of different isoforms of which gives rise to a blood type (e.g. the RBC antibody does not bind to the A or B antigen). In other embodiments the RBC molecule is a molecule, the presence or absence of which or the presence of different isoforms of which gives rise to a blood type. In such cases, the epitope to which the RBC antibody binds is typically not affected by the isoforms that give rise to the blood type, i.e. the antibody binds irrespective of the blood type.

The portion of the molecule to which the antibody binds is the epitope. Where the molecule is a glycoprotein the epitope may be on the carbohydrate portion or the protein portion of the glycoprotein, but is preferably on the protein portion, i.e. is a peptide epitope. The epitope to which the antibody binds may be a carbohydrate or a peptide epitope but is preferably a peptide epitope and is preferably not a carbohydrate epitope. A peptide epitope may be a linear or a conformational epitope.

A RBC molecule may be a protein or glycoprotein that is involved in transport. A RBC molecule that is involved in transport may e.g. be the Band 3 anion transporter (which has different isoforms that define the Diego Blood Group), the Aquaporin 1 water transporter (which defines the Colton Blood Group), Aquaporin 3, Glut1, the Kidd antigen protein, Rhesus associated glycoprotein (RhAG, CD241), the $Na^+/K^+$-ATPase, $Ca^{2+}$-ATPase, the $Na^+K^+2Cl^-$ cotransporter, the $Na^+$-$Cl^-$ cotransporter, the Na—H exchanger, the K—Cl cotransporter, the Gardos Channel. RBC transport proteins that are glycoproteins include but are not limited to: the Band 3 anion transporter, Aquaporin 1, Aquaporin 3, Glut1, Kidd antigen protein, RhAG (CD241), $Na^+/K^+$-ATPase, Na—H exchanger.

A RBC molecule may be a molecule involved in cell adhesion, e.g. ICAM-4 or BCAM (CD239). ICAM-4 and BCAM are both glycoproteins.

A RBC molecule may be a molecule that is believed to have a structural role in the RBC. A RBC molecule that has a structural role may establish linkages with skeletal proteins and may play an important role in regulating cohesion between the lipid bilayer and membrane skeleton, likely enabling the red blood cell to maintain its favourable membrane surface area by preventing the membrane from collapsing (vesiculating). Such molecules may be useful in accordance with the invention if they are on the surface of the erythrocyte. Cell surface molecules that have a structural role include Band 3 (this assembles various glycolytic enzymes, the presumptive $CO_2$ transporter, and carbonic anhydrase into a macromolecular complex termed a "metabolon", which may play a key role in regulating red cell metabolism and ion and gas transport function), RhAG (CD241), proteins that are members of the rht protein 4.11R based macromolecular complex (e.g. Glycophorin C (CD236) and D (which define the Gerbich Blood Group), 10 XK, RhD (CD240D)/RhCE (CD240E), Duffy protein (CD234)), and other glycophorins such as Glycophorin A (CD235a) and B (CD235b).

RBC structural proteins that are glycoproteins include, but are not limited to: Band 3, RhAG, Glycophorins A to D, XK, RhD/RhCE, Duffy protein.

Other RBC molecules include CR1, CD99, CD147, ERMAP, CD238, CD20, CD151, DAF (CD55), AChE, Dombrock (CD297, ART4), CD108 (JMH), Emm and the human orthologue to the mouse TER-119 antigen (Ly76, glycophorin A-associated protein).

The RBC molecule may be a protein, which may be a glycoprotein, or it may be a carbohydrate, but is preferably a protein (e.g. a glycoprotein). The epitope to which the antibody binds may be a carbohydrate or a peptide epitope but is preferably a peptide epitope, and is preferably not a carbohydrate epitope.

The RBC molecule may be defined on the basis of its structure, i.e. as being a type I single pass protein, a type II single pass protein, a type III single pass protein, a multipass protein, a GPI linked protein or combinations thereof.

Examples of type I single pass RBC molecules include glycophorin A (CD235a), glycophorin B (CD235b), glycophorin C (CD236), glycophorin D, CR1, BCAM (CD239), ICAM-4 (CD242), CD99, CD147 and ERMAP.

Examples of type II single pass proteins include CD238, XK, Band3, Aquaporin 1, Kidd, Aquaporin 3, CD151.

Examples of RBC GPI linked proteins are DAF (CD55), AChE, Dombrock (CD297, ART4), CD108 (JMH), Emm.

Examples of carbohydrate antigens, which may be attached to RBC proteins and/or lipids include P1, Pk, P, ABO s, Hh, Lewis or I antigen.

RhD Antigen

A preferred RBC molecule is the RhD molecule (e.g. the human RhD molecule). This is a protein that is found in around 85% of Caucasians in Europe, and which is involved in the "Rhesus blood group system". The frequency of the Rhesus factor may be higher in other populations.

The Rhesus D molecule is highly immunogenic, eliciting anti-Rhesus D antibodies during Rhesus incompatible pregnancies and following transfusion of Rhesus incompatible blood. Modelling studies suggest that the Rhesus D molecule has 12 transmembrane domains with only very short connecting regions extending outside the cell membrane or protruding into the cytoplasm. Those individuals who express the Rhesus D molecule are said to be Rhesus positive. Individuals lacking the D molecule are called Rhesus negative. The other gene involved in the Rhesus system is the RHCE gene, which encodes the RhCE protein which contains C, E, c and e antigens and variants.

It is known that there are multiple epitopes on the D molecule, which explains the "partial D phenotypes", people who carried D antigen on their red cells but who had an alloanti-D in their sera. With at least 9 different epitopes (epD1 to epD9), it is possible for some D variant people to lack certain epitopes so that antibodies are made to the missing D epitopes. Rhesus positive individuals that make antibodies against partial D antigens have been classified into six main different categories (D" to DVI I) each having a different abnormality in the D antigen. It has been shown that these D categories gave different patterns of reaction when tested against panels of human monoclonal anti-D antibodies (Tippett, P, et al Vox Sanguinis. 70(3):123;1996). The different reaction patterns identified the 9 epitopes and so define the different partial D categories. The number of epitopes present on the D antigen varies from one partial D category to another with the DVI category expressing the least, epD3, 4 and 9.

In one embodiment, the RBC molecule is a Rhesus D molecule. In a further embodiment the RBC molecule is a Rhesus D molecule having at least 3 of the 9 epitopes epD1 to epD9, e.g. at least 4, 5, 6, 7, 8 or all 9 of the epD1 to epD9 epitopes. In one embodiment the RBC molecule is a Rhesus D molecule having the sequence of UniProt entry Q02161.

Another Rh antigen is RhCE (UniProt entry P18577) with the C, E, c and e antigens (and variants).

Human Orthologue to the Mouse TER-119 Antigen (Ly-76)

In a preferred embodiment the RBC molecule is the human orthologue of the TER-119 antigen (Ly76). Antibodies to the TER-119 antigen have been used and found to be effective in the Examples, as set out below, in the treatment of three inflammatory conditions. A rat monoclonal antibody to TER-119 has been used in mouse models of ITP (Song S. et. al Blood. 2003;101(9):3708-3713) and has been shown alleviate ITP. The TER-119 antigen is a 52 kD glycophorin A-associated protein, also known as Ly76. It is a molecule associated with cell-surface glycophorin A.

Glycophorin A (GPA, CD135a) and B (GPB, CD235b) and Glycophorin C and D

In one embodiment the RBC molecule is glycophorin A (GPA). Glycophorin A and B are major sialoglycoproteins of the human erythrocyte membrane which bear the antigenic determinants for the MN and Ss blood groups. About 40 variant phenotypes have been identified, the UniProt entries are P02730 (GPA) and P06028 (GPB).

Band 3 (CD233)

In one embodiment the RBC molecule is Band 3 anion transport protein. Band 3 anion transport protein, also known as anion exchanger 1 (AE1) or band 3 or solute carrier family 4 member 1 (SLC4A1), is a protein that is encoded by the SLC4A1 gene in humans; the UniProt entry is P02730. It is a multi-pass membrane protein. CD233 is a phylogenetically preserved transport protein responsible for mediating the electroneutral anion exchange of chloride for bicarbonate across a plasma membrane. It is the major integral membrane glycoprotein of the erythrocyte membrane and is required for the normal flexibility and stability of the erythrocyte membrane as well as for the normal erythrocyte shape via the interactions of its cytoplasmic domain with cytoskeletal proteins, glycolytic enzymes, and haemoglobin.

Frequency of the RBC Molecule in a Population

Not all RBC molecules are found in all individuals. Indeed, it is well known that the differences between the molecules found on RBCs in different individuals are responsible for an individual's blood group. By way of example, in the ABO blood group system an individual in group A has the A antigen present on his or her RBCs and antibodies in their blood to the B antigen. An individual in group B has the B antigen present on his or her RBCs and antibodies in their blood to the A antigen. An individual in group AB has the A and the B antigen present on his or her RBCs and no antibodies to the A or B antigen in their blood. An individual in group O has the O antigen (H antigen) thus no A or B antigen present on his or her RBCs, but antibodies to both A and B antigens in their blood. From this it can be seen that using an anti-A antibody (i.e. an antibody that binds to the A carbohydrate antigen) in the method of the invention will only be effective in those patients who are in group A or group AB, and using an anti-B antibody (i.e. an antibody that binds to the B carbohydrate antigen) in the method of the invention will only be effective in those patients who are in group B or group AB. There are thus advantages associated with using an antibody to a RBC molecule that is found at high levels in all subjects, or in a given population of subjects, e.g. a given population of humans.

The molecule, or epitope may thus be found on at least 50%, 55%, 60%, 65%, 70%, 75%, 80%, 85%, 90%, 95%, 98%, 99% or 99.5% of humans, or on at least 50%, 55%, 60%, 65%, 70%, 75%, 80%, 85%, 90%, 95%, 98%, 99% or 99.5% of a human population of interest.

By way of example the RhD molecule is found in approximately 80% of humans, but may vary dependent on the population.

Molecule Density

The RBC molecule or epitope is preferably found at a density of $10^2$-$10^6$ copies per cell, e.g. $10^2$-$10^5$, $10^2$-$10^4$, $10^2$-$10^3$, $10^3$-$10^4$, $10^3$-$10^5$, $10^4$-$10^5$ copies per cell. It may be advantageous to select a molecule with a suitable density on the RBC so that excessive haemolysis, and the adverse effects that this would have on the subject, e.g. causing anemia, can be avoided. For example, the A and B blood group antigens have a very high density on RBCs (in the region of $10^6$ copies per cell), whereas the RhD molecule is found at around $10^3$-$10^4$ copies and the TER-119 antigen is around $10^5$ copies, and the density of the molecule or epitope is thus preferably $10^2$-$10^5$, $10^2$-$10^4$, $10^2$-$10^3$, $10^3$-$10^4$, $10^3$-$10^5$, $10^4$-$10^5$ copies per RBC.

In some cases the molecule is preferably the RhD molecule or GPA or the human orthologue to TER-119 antigen (GPA associated protein, Ly-76) or Band 3.

In certain other cases the antigen is preferably not the RhD molecule, the human orthologue to TER-119 antigen or the TER-119 antigen (Ly-76) or CD24, or is preferably not the RhD molecule or the TER-119 antigen (Ly-76) or the human homologue to the TER-119 antigen. Alternatively, the antigen is preferably not the RhD molecule, the TER-119 antigen (Ly-76), the human homologue to the TER-119 antigen, CD24 or the RhCE molecule, or is preferably not the RhD molecule or the TER-119 antigen (Ly-76) or the human homologue to the TER-119 antigen or the RhCE molecule.

The epitope is also in some embodiments not a carbohydrate epitope. It is in some embodiments not an ABO epitope, or not a P1, Pk, P, ABO s, Hh, Lewis or I epitope.

Distribution of the RBC Molecule Within the Body

The RBC molecule is preferably expressed selectively on RBCs, which can be advantageous as it means that the antibody will bind preferably to RBCs, so that off target effects may be avoided. For example, the molecule may be found at a higher density (expressed as copies of the molecule per cell) on RBCs than on one or more other cells, e.g. at a density that is at least 2, 3, 4, 5, 10, 20 or 50 fold higher than on one or more other cell. These other cells may be blood cells (e.g. white blood cells (lymphocytes, monocytes, and granulocytes) or platelets). These other cells may also be cells that are associated with the vascular system (e.g. endothelial cells or fibroblasts). It is preferred that the molecule is not expressed on white blood cells, platelets and/or cells that are associated with the vascular system, e.g. not expressed on one or more of white blood cells, platelets and cells that are associated with the vascular system. In certain embodiments the molecule is expressed at a density that is at least 2, 3, 4, 5, 10, 20 or 50 fold higher than on any other cell type, e.g. at least 2, 3, 4, 5, 10, 20, or 50 fold higher than on one or more of the cell types referred to above.

As a consequence, the antibody binds preferably to RBCs. The antibody thus binds preferably to RBCs compared to one or more other cell such as a blood cell (e.g. white blood cells (lymphocytes, monocytes, and granulocytes) or platelets) and/or to cells that are associated with the vascular system (e.g. endothelial cells or fibroblasts). It is preferred that the antibody does not bind to white blood cells, platelets and/or cells that are associated with the vascular system. In certain embodiments the antibody does not bind to any other cell type, e.g. does not bind to one or more of white blood cells, platelets and cells that are associated with the vascular system. Detection of antibody binding can be carried out using standard procedures known in the art (e.g. immunoassays detecting antibody binding to cells, such as by incubating antibody with cells and detecting bound antibody using an appropriately labelled second antibody, e.g. with flow cytometry).

Alternatively, or additionally the molecule may be expressed on RBCs and on other cell types, however in such cases these other cell types are found at a lower frequency in the body or in a region of the body which the antibody cannot access. This can be advantageous as it means that the antibody will bind preferably to RBCs, as it is statistically more likely to encounter such cells, so that off target effects may be avoided. For example, the molecule may be found on cells that are found at a lower frequency in the body or the vascular system than RBCs (e.g. there are at least 2, 3, 4, 5, 10, 20 or 50 fold fewer of these cells in the body or in the vascular system than RBCs). Additionally or alternatively these other cell types are found, for example, in the brain.

Expression of the molecule on different cell types can be assayed by standard in vitro methods known in the art (e.g. based on protein or encoding nucleic acid levels, such as immunoassays and PCR based methods), and the ability of an antibody to bind to different cell types can similarly be assayed using immunoassays in vitro. Enumeration of different cell types can also be assayed by standard methods known in the art.

Antibody

The antibody to be used is an antibody to a RBC molecule. In some embodiments it is specific for the RBC molecule. This means that the binding between the antibody and the RBC molecule is specific binding. As used herein, the term "specific binding" refers to a binding reaction between the antibody of the invention and the RBC molecule, in which the dissociation constant (KD) is $10^{-7}$M or less, in particular $10^{-8}$ M or less, $10^{-9}$ M or less or $10^{-10}$ M or less. The term "KD", as used herein, is intended to refer to the dissociation constant, which is obtained from the ratio of dissociation rate (Kd) to association rate (Ka) and is expressed as a molar concentration (M). KD values can be determined using methods well established in the art. One method for determining the association and disassociation dynamics of an antibody is by using surface plasmon resonance, e.g. by using a biosensor system such as a Biacore™ system.

In general, a smaller KD value is preferred. This corresponds to a higher affinity for the molecule.

The antibody of the invention typically binds to the RBC molecule with high affinity. As used herein, the term "high affinity" refers to an antibody that binds to the RBC molecule with a KD of $10^{-7}$M or less, $10^{-8}$ M or less, $10^{-9}$ M or less, or $10^{-10}$ M or less. However, "high affinity" binding can vary for different antibodies. For example, "high affinity" binding for an IgG antibody refers to a KD of $10^{-8}$ M or less, $10^{-9}$ M or less, or $10^{-19}$ M or less, whereas high affinity binding for an IgM antibody refers to an antibody having a KD of $10^{-7}$ M or less, or $10^{-8}$ M or less. In some embodiments, the antibody is a high affinity IgG antibody.

In some embodiments, the antibody for use in methods of the invention will bind to its RBC molecule with a KD value in the range of $10^{-7}$ M to $10^{-11}$ M, e.g. as determined by surface plasmon resonance (SPR) techniques (e.g. Biacore).

The affinity can also be calculated using other techniques (e.g. equilibrium binding assays). The affinity and concentration of the anti RBC antibody define how much binding to the RBCs is achieved. The binding can also be driven by the avidity of an antibody, especially when using a multivalent IgM antibody. "Avidity" refers to the accumulated strength of multiple affinities of non-covalent binding interactions.

Clone LD1/2-6-3 of the anti-RhD antibody in the IgG1 format (MDJ8s) shows an affinity to RBCs in the nanomolar range (KD=3 nM; with calculated 14'069 binding sites per cell) (Miescher S et al Br.J Haematol. 2000;111(1):157-166). TER-119 (rat IgG2b) shows an affinity of about 30 nM (calculated from FACS saturation experiments).

Functional Definitions of the Antibody

In some embodiments the antibody of the invention binds to RBCs in vitro and in vivo (e.g. to human RBCs). This can be assessed in vitro, e.g. by detecting binding of antibody to RBCs using immune based techniques. This can be carried out using standard procedures known in the art (e.g. detecting antibody binding to RBCs, such as by incubating antibody with RBCs and detecting bound antibody using an appropriately labelled second antibody, e.g. with flow cytometry, and for example as set out in Example 7). Antibody binding in vivo can also be detected, e.g. by administering antibody to a subject, and detecting antibody binding to RBCs in a sample from the subject, using an appropriately labelled second antibody, (e.g. with flow cytometry).

The antibody of the invention may additionally or alternatively cause MPS (also described as RES) blockade in a human or in a suitable animal (e.g. mouse) model in vivo. MPS blockade in mouse models can be assessed using assays that are known in the art, e.g. as described in (Song S. et. al Blood. 2003;101(9):3708-3713). Briefly, RBCs that have been taken from a suitable mouse model (e.g. SCID) are incubated with the antibody of the invention in vitro to cause opsonisation, and the opsonised RBC are labelled with a suitable marker and injected to a suitable mouse. Samples taken at time intervals after the injection are evaluated for RBC and labelled RBC number. A reduction in the number of circulating labelled RBCs over time following introduction is indicative of MPS blockade. The reduction may be e.g. to 30-80%, 40-75% or 50-65% of the circulating labelled RBCs compared to the number at the first time point assessed. MPS blockade in a human can be assessed by a surrogate assay to measure MPS function which is based on a phagocytosis assay. The clinically accepted assay has been known in the art as monocyte monolayer assay (MMA) (Tong T N & Branch D R J Vis Exp. 2017;119:55039. Tong T N et al Transfusion. 2016;56(11):2680-2690).

The antibody may additionally or alternatively cause haemolysis in vivo, e.g. in an animal model or in a human subject. This is measured e.g. by a reduction in RBC number after administration of the antibody. This can be determined by standard techniques such as obtaining a RBC count in a blood sample after antibody administration, or by measuring one or more markers of haemolysis in a blood sample (e.g. free haemoglobin). A reduction in the number of RBCs over time following introduction of the antibody is indicative of haemolysis in vivo.

Where a reduction in RBC numbers is evaluated in this method, there may be a reduction in RBC numbers to less than 99, 98, 97, 96, 95, 94, 93, 92, 91, 90, 80, 70, 60, 50% of the RBC numbers seen before administration of the antibody.

The antibody may additionally cause a reduction in platelet count or platelet concentration in vivo, e.g. in an animal model or in a human subject. This is measured e.g. by determining platelet number or concentration in a sample taken from the subject number after administration of the antibody. This can be determined by standard techniques.

The antibody may additionally or alternatively ameliorate murine ITP in a mouse ITP model, e.g. as described in Example 2. Amelioration of murine ITP in such a mouse model, as a result of administration of the antibody, is determined by e.g. comparing platelet numbers in a treated mouse compared to the level before treatment. An increase in platelet count of at least 1.25, 1.5, 1.75, 2, 2.5, 3 after 1.5 hours in treated mice, compared to the level before treatment may be indicative of amelioration of murine ITP in such a mouse model.

The antibody may additionally or alternatively ameliorate inflammatory arthritis in a mouse model of Rheumatoid arthritis, e.g. as described in Example 3. Pretreatment with the antibody of the invention 2 hours prior to injection with K/B×N serum may in some embodiments reduce arthritis scores and/or reduce ankle width in mice injected with K/B×N serum, compared to non-pretreated mice injected with K/B×N serum, as assessed in accordance with the standard procedure described in Mott et al (Mott P J et al PLoS One. 2013:8(6):e65805). The effects may be observed e.g. 7 days after treatment. Ankle width and/or clinical score is in some embodiments reduced by at least 5, 10, 15, 20, 30, 40, 50% compared to ankle width and/or clinical score without treatment. Clinical score may be reduced to 0 in some instances.

Likewise, the antibody may additionally or alternatively reverse established inflammatory arthritis in a mouse model of Rheumatoid arthritis, e.g. as described in Example 4. Administration of the antibody 5 days after injection of K/B×N serum may reduce clinical score and/or ankle width after treatment, e.g. 3 days after treatment. Ankle width and/or clinical score is in some embodiments reduced by at least 5, 10, 15, 20, 30, 40, 50% compared to ankle width and/or clinical score before treatment. Clinical score may be reduced to 0 in some instances.

The antibody may additionally or alternatively ameliorate inflammatory arthritis in the CAbIA model, e.g. as described in Example 5. Treatment with the antibody of the invention on day 5, after administration with anti-collagen mAb cocktail (day 0) and LPS (day 3) may in some embodiments protect from arthritis, measured e.g. by reduced clinical and histological arthritis scores compared to mice injected with collagen mAb cocktail (day 0) and LPS (day 3) but not treated with the antibody of the invention, as assessed in accordance with the procedure described in Example 5. The effects may be observed e.g. 1 day after treatment. Histological and/or clinical score is in some embodiments reduced to 0, or reduced by at least 50, 60, 70, 80% compared to histological and/or clinical score without treatment.

The antibody may additionally or alternatively prevent or reduce 34-1-2S induced hypothermia in a mouse model of TRALI. Injection of SCID mice with the antibody of the invention may reduce hypothermia induced by the injection 1 hour subsequently of the anti-MHC I antibody 34-1-2s (Fung Y L et al Blood. 2010;116(16):3073-3079), as assessed by rectal temperature measurement (e.g. as in Example 6). The rectal temperature measurement in mice treated with the antibody of the invention and the anti-MHC I antibody 34-1-2s may be at least 2, 3, 4, 5, 6, 7, 8, 9 or 10° C. higher than the rectal temperature measurement in mice treated with the anti-MHC I antibody 34-1-2s alone 2 hours after treatment.

The antibody may additionally or alternatively reduce or prevent 34-1-2S induced pulmonary edema in a mouse model of TRALI. Injection of SCID mice with the antibody of the invention may reduce pulmonary edema induced by the injection 1 hour subsequently of the anti-MHC I antibody 34-1-2S, as assessed by post-mortem determination of wet/dry (W/D) lung weight ratios, after sacrificing mice 2 hours after treatment. Mice that receive 34-1-2S after pre-treatment with the antibody may display lung W/D ratios significantly lower than mice injected with 34-1-2S.

The antibody may additionally or alternatively inhibit phagocytosis of opsonised platelet in an in vitro assay. The ability of an antibody to inhibit phagocytosis of opsonised platelets in an in vitro assay can be assessed e.g. by comparing the amount of platelet phagocytosis in the presence of RBCs to the amount of platelet phagocytosis in the presence of RBCs which have been opsonised with the antibody of the invention, e.g. using the method of example 7. A reduction in the amount of platelet phagocytosis in the presence of RBCs which have been opsonised with the antibody of the invention compared to the amount of platelet phagocytosis in the presence of RBCs which have not been opsonised with the antibody of the invention may be expressed as a reduction in the platelet phagocytic index, e.g. of at least 20, 30, 40, 50, 60, 70, 80, 90, 100%.

To account for the fact that human and mouse RBC molecules may have differences in their primary sequence, and hence may have different binding properties to the antibody being tested, the above assays are, where possible, carried out using human RBCs (for in vitro assays). Where any mouse models are used, the mouse models may be modified (e.g. genetically manipulated) so that the appropriate human RBC molecule is expressed.

In some embodiments administration of the antibody does not lead to tolerance (e.g. immunological tolerance) of or to an antigen, e.g. an antigen involved in or which causes the autoimmune condition, such as tolerance of or to an antigen which may be a protein or peptide that is administered with the antibody. In some embodiments the antibody is not administered with another protein (e.g. a protein or peptide antigen).

Structural Antibody Definitions

The term "antibody" as used herein typically refers to both antibodies and antigen-binding fragments thereof. A naturally occurring "antibody" is a glycoprotein comprising at least two heavy (H) chains and two light (L) chains inter-connected by disulphide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Preferably the antibody is a molecule that consists of the above specified regions/domains. The antibody may comprise only two antibody heavy chains and two antibody light chains, interconnected by disulphide bonds, e.g. wherein each antibody heavy chain consists of an antibody heavy chain variable region and three constant region domains (CH1, CH2, CH3) and each antibody light chain consists of an antibody light chain variable region and a light chain constant region.

Preferably the antibody does not contain any non-immunoglobulin sequence, e.g. it consists of immunoglobulin sequence, and no additional sequence is present (e.g. fused to the N or C terminus). This immunoglobulin sequence may be a sequence that is or corresponds to a sequence present in an antibody, or immunoglobulin, especially an IgG. The skilled person is readily able to identify such sequences based on e.g. the conserved nature of the immunoglobulin fold.

Preferably the antibody is not a fusion protein with any additional protein or peptide, e.g. the antibody is not linked to or fused with any non-antibody protein or peptide, such as an antigen. "Linked to or fused with" includes a direct or indirect linkage, but can be a bond that is a chemical bond, such as a peptide bond between the antibody and the additional protein or peptide, e.g. may be a molecular fusion. Indirect linkage may e.g. be via a particle that is attached to the antibody (e.g. a microparticle, a nanoparticle, a liposome, a polymersome or a micelle). The additional protein or peptide may e.g. be a tolerogenic antigen (e.g. an antigen that is administered in order to generate tolerance to that antigen).

Antibodies include, but are not limited to, isolated, polyclonal, monoclonal, multispecific, monospecific, mouse, human, fully human, humanized, primatized or chimeric antibodies. In one embodiment, the antibody is isolated. Typically, the antibody of the invention is a chimeric, fully human, human or humanized antibody. In a further embodiment the antibody is a human or humanized monoclonal antibody. The term antibody includes antigen binding fragments, as set out in more detail below. Alternatively, the RBC antibody may be a polyclonal preparation, e.g. a polyclonal anti-RhD preparation.

An "isolated antibody", as used herein, refers to an antibody that is substantially free of other cellular material and/or chemicals and/or to an antibody that is substantially free of other antibodies having different antigenic specificities (e.g. that bind to other antigens). Compositions as discussed elsewhere herein may in particular comprise an isolated antibody, e.g. may consist of isolated antibody (e.g. an isolated antibody preparation) and a pharmaceutically acceptable carrier or diluent as defined in more detail below. The term "isolated" may additionally apply to a polyclonal preparation, e.g. where the polyclonal antibody preparation is substantially free of other cellular material and/or chemicals and/or to an antibody that is substantially free of other antibodies having different antigenic specificities (e.g. that bind to other antigens).

A "monoclonal antibody" or "monoclonal antibody composition" as used herein is a preparation of antibody molecules of single molecular composition. A monoclonal antibody composition displays a single binding specificity and affinity for a particular epitope.

A "human antibody" is intended to include antibodies having variable regions in which the framework, CDR regions and the constant region (if present) are derived from sequences of human origin, e.g., human germline sequences, or mutated versions of human germline sequences. The human antibodies may thus include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. Such human monoclonal antibodies may be produced by a hybridoma which includes a B cell obtained from a transgenic nonhuman animal, e.g., a transgenic mouse, having a genome comprising a human heavy chain transgene and a light chain transgene fused to an immortalized cell. Fully human sequence derived antibodies have no murine or other non-human sequence, and are largely produced via two sources: phage display technologies and transgenic mice.

"Humanized antibodies" contain murine or other non-human sequence derived CDR regions that have been engrafted, along with any necessary framework back-mutations, into human sequence-derived variable regions.

Antigen binding fragments, variants and derivatives may also be used and include but are not limited to, a Fab, Fab' and F(ab')2, Fd, Fv, single-chain Fv (scFv), disulfide-linked Fv (sdFv), or minibodies (antibody fragments that are missing the constant region in the Fab portion). ScFv molecules are known in the art and are described, in, for example, U.S. Pat. No. 5,892,019. In some embodiments, the antibody is selected from the group consisting of IgG, IgM. In other embodiments a fragment such as F(ab')2, F(ab)2, Fab', Fab, ScFvs, diabodies, triabodies, tetrabodies and minibodies may be used. Should a fragment be used, it is preferably fused or linked to an appropriate Fc-comprising moiety. The antibody is preferably not an scFv or preferably does not comprise an scFv.

In some embodiments the antibody is of the type IgG or IgM. In particular, the antibody may be an IgG of any of type. In particular it may be a rat, mouse, human or humanised IgG or IgM, of any of type, preferably a human or humanised IgG or IgM. Human or humanised IgG may e.g. be of type IgG1, IgG2, IgG3 or IgG4. Rat or mouse IgG may also be used (e.g. rat IgG1, IgG2a, IgG2b or IgG2c, or mouse IgG2a, IgG2b, IgG2c, IgG3 or IgG4).

The antibody preferably comprises an Fc domain or portion thereof. As a non-limiting example, a suitable Fc domain may be derived from an immunoglobulin subclass such as IgG. In some embodiments, a suitable Fc domain or portion thereof is derived from IgG1, IgG2 IgG3, or IgG4 (e.g. human), or derived from rat or mouse IgG (e.g. rat IgG1, IgG2a, IgG2b or IgG2c, or mouse IgG2a, IgG2b, IgG2c, IgG3 or IgG4). Particularly suitable Fc domains include those derived from human or humanized antibodies.

The antibody preferably binds to an Fc receptor. This may be an Fcy receptor (e.g. FcγRl (CD64), FcγRIIA (CD32), FcγRIIB (CD32), FcγRIIIA (CD16a), FcγRIIIB (CD16b)). The ability to bind to an Fc receptor may in some cases depend on glycosylation of the Fc domain and as such the Fc domain or portion thereof is preferably glycosylated (or preferably not deglycosylated).

The antibody preferably has low complement activation activity. By "low complement activation activity" is meant that the antibody, when surface-bound or immune complexed, activates complement less than surface bound or immune-complexed human IgG3. The antibody preferably activates complement less than 90% than human IgG3, preferably less than 80%, 75%, 70%, 60%, 50%, 40% than human IgG3, more preferably less than 30%, 25% or 20% than human IgG3, even more preferably less than 15% or even less than 10% than human IgG3.

The antibody may be modified in the Fc region in order to reduce complement activation activity. Preferably the complement activation activity is reduced by at least 10%, 20%, 30% or 40% compared to the unmodified antibody; more preferably the complement activation activity is reduced by at least 50%, 60% or 70%, even more preferably the complement activation activity is reduced by at least 80 or even 90% when compared to the unmodified antibody.

The complement activation is determined by monitoring the generation of soluble terminal complex (sC5b-C9) during incubation of surface bound or immune-complexed antibody with a complement source; the terminal complex can be measured by a standard ELISA.

Methods for the generation and characterization of antibodies to certain RBC molecules are known in the art and have been described previously. For example, W09749809 describes anti Rhesus D antibodies, the TER-119 antibody (Kina T et al Br J Haematol. 2000;109: 280-287) has been widely used in mouse models and anti CD24 (which is a mouse RBC molecule) has also been tested in mouse models (Song S. et. al Blood. 2003; 101(9):3708-3713).

In some embodiments the RBC antibody is a polyclonal preparation of anti-D. Such anti-D polyclonal preparations are available commercially (e.g. Rhophylac®); alternatively, a cocktail of several monoclonal anti-D antibodies may be used.

In some embodiments, antibodies for use in methods of the invention are produced recombinantly.

In some embodiments, the RBC antibody comprises one or more complementarity determining regions (CDRs) as found in the TER-119 antibody as referred to in the examples (e.g. one, two, three, four, five or six, or at least one, two, three, four, five or six of these CDRs). The RBC antibody may have the sequences of the light and/or heavy chain as found in the TER-119 antibody as referred to in the examples.

In some embodiments, the RBC antibody comprises one or more complementarity determining regions (CDRs) as found in the anti-human RhD antibody as referred to in the examples (e.g. one, two, three, four, five or six, or at least one, two, three, four, five or six of these CDRs). The RBC antibody may have the sequences of the light and/or heavy chain as found in the anti-human RhD antibody as referred to in the examples.

In some embodiments, the RBC antibody comprises one or more complementarity determining regions (CDRs) as found in the anti-human GPA antibody as referred to in the examples (e.g. one, two, three, four, five or six, or at least one, two, three, four, five or six of these CDRs). The RBC antibody may have the sequences of the light and/or heavy chain as found in the anti-human GPA antibody as referred to in the examples.

Methods of Treatment

The invention provides an antibody to a RBC for use in a method of treating or preventing an inflammatory condition and a method of treating or preventing an inflammatory condition in a subject, comprising administering to a subject in need thereof a therapeutically effective amount of an antibody to a RBC.

The invention also provides a method of treating or preventing an inflammatory condition in a subject comprising administering to a subject in need thereof a therapeutically effective amount of the subject's own or (alternatively or additionally) donated human erythrocytes sensitized with an antibody to a RBC.

As used herein, the terms "subject" or "individual" or "patient" refers to someone in need of therapy. As used herein, the term "subject" includes any human or nonhuman animal. The term "nonhuman animal" includes all vertebrates, e.g. mammals and non-mammals, such as mice, rats, nonhuman primates, sheep, dogs, cats, horses and cows. Typically, however, the term "subject" refers to a human.

The terms "effective amount" or "amount effective to" or "therapeutically effective amount" includes reference to a dosage of a therapeutic agent sufficient to produce a desired result, in particular the prevention of disease progression and/or the amelioration of symptoms associated with the disease for which the subject is being treated.

As used herein, the terms "treat", "treating" or "treatment" refer to therapeutic measures, wherein the object is to reduce or slow down (lessen) an existing undesired physiological change or disorder, such as inflammation. Beneficial or desired clinical results include, but are not limited to, alleviation of symptoms, diminishment of extent of disease (including extent of inflammation), stabilized (i.e., not worsening) state of disease, delay or slowing of disease progression, amelioration or palliation of the disease state, and remission (whether partial or total). "Treatment" can also mean prolonging survival as compared to expected survival if not receiving treatment. A subject in need of treatment typically refers to a subject who is already suffering from the disease, condition or disorder for which treatment is provided, but may include a subject at risk of suffering from the disease, condition or disorder for which treatment is provided. In some embodiments the subject who is being treated has one or more symptoms of the autoimmune disease.

In the context of a disease state related to chronic inflammation, the term "treating" includes any or all of inhibiting replication or stimulation of pro-inflammatory immune cells, inhibiting or decreasing the chronic inflammatory state of a dysregulated immune system or decreasing the frequency and/or intensity of flares experienced by subjects having an autoimmune condition or disease.

As used herein "prevention" is used to mean that the disease state is not already established, and the method of the invention may therefore prevent the disease state from establishing, or may reduce or slow down (lessen) the undesired physiological change or disorder, such as the inflammation. In the context of prevention, treatment may start before the disease state is already established.

The antibody is preferably administered to the subject in a composition as defined elsewhere herein. In certain preferred embodiments the composition does not comprise any cells and/or no cells are co-administered with the composition. In other preferred embodiments the antibody is the only proteinaceous active ingredient in the composition and/or no proteinaceous active ingredient is co-administered with the composition. An active ingredient may e.g. be an ingredient in a composition that is intended to exert an effect on the subject and/or that exerts an effect on the subject. "Active ingredient" thus may exclude e.g. carriers and/or excipients.

In certain preferred embodiments the antibody is present in a composition, and the antibody in said composition that is to be administered is not bound to any antigen (e.g. is not bound to any antigen via the antibody CDRs). Alternatively stated, the antibody binds to antigen in the subject after it has been administered to the subject, e.g. only after administration of the antibody e.g. wherein antibody-RBC complexes are formed e.g. in the blood of the subject after administration of the antibody and/or wherein any antibody/RBC complexes present in the subject are formed after administration of the antibody to the subject.

In certain preferred embodiments the antibody is present in a composition, and the CDRs of said antibody in said composition that is to be administered are available for binding to antigen.

Combinations

In some embodiments, the antibody of the invention is administered in combination with one or more other therapeutic agent(s). For example, the combination therapy can include an antibody of the invention combined with at least one other anti-inflammatory agent, or agent that is used to treat an inflammatory condition or to alleviate the symptoms thereof. For example, in a specific embodiment, the method of treating or preventing an inflammatory condition includes administering to a subject in need thereof an effective amount of an antibody to a RBC in combination with one or more therapeutic agents selected from an anti-inflammatory, an immunosuppressant and/or an analgesic. Examples include NSAIDs, e.g. such as aspirin, ibuprofen), corticosteroids (such as prednisone and prednisolone), aminosalicylates, azathioprine, mercaptopurine, methotrexate and biologic therapies (e.g. other antibodies).

The multiple agents may be formulated for simultaneous or sequential use.

Dosage Regimens

Dosage regimens are typically adjusted to provide the optimum desired response (e.g. a therapeutic response). For example, a single bolus of the antibody may be administered. In other embodiments, several divided doses may be administered over time or the dose may be proportionally reduced or increased as indicated by the needs of the therapeutic situation. The antibody may be administered by any route, e.g. parenteral or enteral, or generated in vivo using DNA vaccine technology. Preferred parenteral routes include intravenous, intramuscular, intraperitoneal, intracerebrospinal, intracerebral, subcutaneous, intra-articular, intrasynovial, intrathecal, intrapulmonary (e.g nebulized), intranasal, intradermal topical administration or by inhalation. Combination of two or more recited routes may be used. In a specific embodiment, the antibody to a RBC is administered by intravenous or subcutaneous administration.

In some embodiments, the antibody can be administered intravenously (IV), e.g. as an intravenous infusion or as an intravenous bolus. The term "intravenous infusion" refers to introduction of a drug, e.g. an antibody into the vein of an animal or human patient over a period of time greater than approximately 5 minutes, for example, between approximately 30 to 90 minutes, although, according to the disclosure, intravenous infusion is alternatively administered for 10 hours or less, e.g. 5 hours or less or 2 hours or less. In one particular embodiment, the duration of the infusion is at least 60 minutes. The term "intravenous bolus" or "intravenous push" refers to drug administration, e.g. of an antibody into a vein of an animal or human such that the body receives the drug in approximately 15 minutes or less, for example, 5 minutes or less. By way of example the antibody of the invention is administered intravenously at doses of 1 mg/kg to 100 mg/kg in intervals of 1 week to 4 weeks.

In other embodiments, an antibody of the invention can be administered subcutaneously. The term "subcutaneous administration" refers to introduction of the antibody under the skin of a subject, for example, within a pocket between the skin and underlying tissue, by relatively slow, sustained delivery from a drug receptacle. The pocket can be created by pinching or drawing the skin up and away from underlying tissue. In some embodiments, a composition comprising an antibody is introduced under the surface of the skin of the patient with a hypodermic needle.

In some embodiments, the antibody is administered in a dosage dependent on the subject's body weight, for example the antibody is administered so that an amount of antibody of about 0.001 mg/kg to about 100 mg/kg of the subject's body weight is administered in a given time scale, e.g. in one day, or one week, two weeks or one month. In certain embodiments, such weight-based dosage is chosen from about 0.01 mg/kg body weight per day or week, two weeks or one month, about 0.3 mg/kg body weight, about 1 mg/kg body weight per day or week, two weeks or one month, about 3 mg/kg body weight per day or week, two weeks or one month, and about 10 mg/kg body weight per day or week, two weeks or one month.

In some embodiments, the antibody is administered at a fixed dosage. In a specific embodiment, the antibody is administered so that an amount of antibody at a fixed dosage from about 50 μg to about 2000 mg is administered in a given time scale, e.g. in one day, one week, two weeks or one month.

The dosage regimen is thus defined in terms of the amount of antibody that is administered to a subject in a given time scale. The frequency of administration during that time scale will determine the amount of antibody that is administered each time. For example, if the dosage is 10 mg/kg/week, this could be administered as a single 10 mg/kg dose or as multiple doses with appropriately reduced amounts of antibody (e.g. 25 mg/kg doses in one week). In some embodiments, the antibody is administered as a single dose (e.g. daily, weekly once every two weeks or once every month), or as multiple doses more frequently if the amount of antibody is lower each time it is administered. In general administration by the subcutaneous route can be carried out more frequently (e.g. once a day) than intravenous administration (e.g. once every two weeks or once a month). In some embodiments, the antibody to a RBC is administered as a single dose; in one or more doses per week, in two or more doses once per week; once every two weeks; once every three weeks; once every four weeks; once a month; once every 3 months; or once every six months.

In some embodiments the antibody to a RBC is administered in intervals of one day to six months. In a specific embodiment, the antibody to a RBC is administered in intervals of 1 week; 2 weeks; 3 weeks; 4 weeks; 1 month; 2 months; 3 months; 4 months; 5 months; or 6 months.

In some embodiments, the antibody is administered as a single dose or is administered in two or more doses once per week, once every two weeks, once every three weeks, once every four weeks, once a month, once every 3 months, once every six months, or at varying intervals.

In some embodiments, erythrocytes, either the patient's own erythrocytes or donated human erythrocytes, are combined with the antibody in vitro, and then these "sensitized" erythrocytes, i.e. erythrocytes coated with the antibody, are administered to the patient.

Pharmaceutical Compositions

The present invention also provides a composition, e.g. a pharmaceutical composition, comprising an antibody of the invention, e.g. an isolated antibody. Such compositions may include one or a combination of (e. g. two or more different) antibodies of the invention. For example, a pharmaceutical composition of the invention can comprise two antibodies that bind to different RBC molecules, antigens, or to different antigens or to different epitopes or that have otherwise complementary activities. The compositions as discussed herein may be used in the methods of the invention. The antibody as referred to herein is preferably administered in a composition as referred to herein.

In some embodiments, the disclosure provides a pharmaceutical composition comprising one or more antibody of the invention and a pharmaceutically acceptable carrier. The term "pharmaceutically acceptable carrier" includes any and all solvents, buffers, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e. g. by injection or infusion). For example, in some embodiments, a composition for intravenous administration typically is a solution in sterile isotonic aqueous buffer.

In certain preferred embodiments the composition, e.g. for use in the methods of the invention comprises an isolated antibody. The composition may be used in the methods of the invention wherein the active ingredient is an isolated antibody (e.g. where the only proteinaceous active ingredient (e.g. protein or peptide) is an isolated antibody, or where the only active ingredient is an isolated antibody). In certain embodiments the composition may consist of isolated antibody and a pharmaceutically acceptable carrier.

In certain embodiments the antibody is present in a composition which does not comprise any cells, e.g. any blood cells, such as red blood cells, and in particular does not comprise any red blood cells bound to the antibody. The antibody may thus be present in a composition which is substantially free of cells, e.g. any blood cells, such as red blood cells, and in particular does not contain red blood cells bound to the antibody.

In certain preferred embodiments the antibody is not encapsulated, e.g. not encapsulated in a cell, e.g. is not encapsulated in a blood cell such as a RBC.

Such pharmaceutical carriers and excipients as well as the preparation of suitable pharmaceutical formulations are well known in the art (see for example Pharmaceutical Formulation Development of Peptides and Proteins," Frokjaer et al., Taylor & Francis; Handbook of Pharmaceutical Excipients, 3rd edition, Kibbe et al., Pharmaceutical Press, 2000). In certain embodiments, a pharmaceutical composition can comprise at least one additive such as a bulking agent, buffer, or stabilizer. Standard pharmaceutical formulation techniques are well known to persons skilled in the art (see, e.g. 2005 Physicians' Desk Reference®, Thomson Healthcare: Monvale, N.J., 2004; Remington: The Science and Practice of Pharmacy, 20th ed., Gennaro et al., Eds. Lippincott Williams & Wilkins: Philadelphia, Pa., 2000). Suitable pharmaceutical additives include, e.g., sugars like mannitol, sorbitol, lactose, sucrose, trehalose, or others, amino acids like histidine, arginine, lysine, glycine, alanine, leucine, serine, threonine, glutamic acid, aspartic acid, glutamine, asparagine, phenylalanine, proline, or others, additives to achieve isotonic conditions like sodium chloride or other salts, stabilizers like Polysorbate 80, Polysorbate 20, Polyethylene glycol, propylene glycol, calcium chloride, or others, physiological pH buffering agents like Tris(hydroxymethylaminomethan), and the like. In certain embodiments, the pharmaceutical compositions may contain pH buffering reagents and wetting or emulsifying agents. In further embodiments, the compositions may contain preservatives or stabilizers.

Depending on the route of administration, the antibodies according to the invention may be coated in a material to protect the compound from the action of acids and other natural conditions that may inactivate the compound.

In some embodiments, a pharmaceutical composition of the invention comprises an antibody in the form of an injectable formulation. In other embodiments, a pharmaceutical composition of the invention comprises an antibody or antigen-binding fragment thereof, which may be formulated for parenteral administration, e.g. formulated for intravenous, subcutaneous, or intramuscular administration.

In some embodiments, pharmaceutically acceptable carriers include sterile aqueous solutions or dispersions and sterile powders for the extemporaneous preparation of sterile injectable solutions or dispersion. In certain embodiments, the disclosure provides a sterile powder of antibody of the invention for the preparation of sterile injectable solutions, e.g. in a container such as a vial.

General

The term "comprising" encompasses "including" as well as "consisting" e.g. a composition "comprising" X may consist exclusively of X or may include something additional e.g. X+Y.

The term "about" in relation to a numerical value x means, for example, x±10%. It will be understood that the invention has been described by way of example only and modifications may be made whilst remaining within the scope and spirit of the invention.

STATEMENTS OF INVENTION

1. An antibody to a red blood cell (RBC) for use in a method of treating or preventing an inflammatory condition.

2. A method of treating or preventing an inflammatory condition in a subject, comprising administering to a subject in need thereof a therapeutically effective amount of an antibody to a red blood cell (RBC).

3. Use of an antibody to a red blood cell (RBC) for the manufacture of a medicament for treating or preventing an inflammatory condition.

4. The antibody for use of clause 1 or the method of clause 2 or the use of clause 3, wherein the antibody binds specifically to a RBC molecule.

5. The antibody for use of clause 1 or 4, or the method of clause 2 or 4, or the use of clause 4, wherein the antibody is isolated, polyclonal, monoclonal, multispecific, monospecific, mouse, human, fully human, humanized, primatized or chimeric.

6. The antibody for use of any one of clauses 1 or 4 or 5 or the method of any one of clauses 2 or 4 or 5, or the use of any one of clauses 3 to 5, wherein the antibody is monoclonal and human or humanised, and is optionally isolated.

7. The antibody for use of clause 6 or the method of clause 6, or the use of clause 6 wherein the antibody is of type IgG.

8. The antibody for use of clause 6 or 7 or the method of clause 6 or 7, or the use of clause 6 or 7, wherein the antibody is of type IgG1.

9. The antibody for use of clause 6 or 7 or the method of clause 6 or 7, or the use of clause 6 or 7, wherein the antibody is of type IgG2.

10. The antibody for use of clause 6 or 7 or the method of clause 6 or 7, or the use of clause 6 or 7, wherein the antibody is of type IgG3.

11. The antibody for use of clause 6 or 7 or the method of clause 6 or 7, or the use of clause 6 or 7, wherein the antibody is of type IgG4.

12. The antibody for use of any one of clauses 1 or 4 to 11 or the method of any one of clauses 2 or 4 to 11, or the use of any one of clauses 3 to 11, wherein the antibody comprises an Fc region and preferably binds to an Fc receptor, e.g. Fcγ receptor (FcγR), such as FcγRI (CD64), FcγRIIA (CD32), FcγRIIB (CD32), FcγRIIIA (CD16a), FcγRIIIB (CD16b).

13. The antibody for use of any one of clauses 1 or 4 to 11, or the method of any one of clauses 2 or 4 to 11, or the use of any one of clauses 3 to 11, wherein the antibody has low complement activation activity.

14. The antibody for use, the method or the use of clause 13, wherein the Fc region has been modified to reduce complement activation.

15. The antibody for use of any one of clauses 1 or 4 to 14 or the method of any one of clauses 2 or 4 to 14, or the use of any one of clauses 4 to 14, wherein the inflammatory condition is an autoimmune condition.

16. The antibody for use of any one of clauses 1 or 4 to 15 or the method of any one of clauses 2 or 4 to 15, or the use of any one of clauses 3 to 15, wherein the autoimmune condition is an auto-antibody mediated autoimmune condition.

17. The antibody for use of any one of clauses 1 or 4 to 16 or the method of any one of clauses 2 or 4 to 16, or the use of any of clauses 4 to 16, wherein the autoimmune condition is a condition in which elevated IL-10 is present.

18. The antibody for use of any one of clauses 1 or 4 to 17 or the method of any one of clauses 2 or 4 to 17, or the use of any of clauses 4 to 17, wherein the autoimmune condition is a neurological condition.

19. The antibody for use of any one of clauses 1 or 4 to 18 or the method of any one of clauses 2 or 4 to 18, or the use of any of clauses 4 to 18, wherein the autoimmune condition is not ITP.

20. The antibody for use of any one of clauses 1 or 4 to 19 or the method of any one of clauses 2 or 4 to 19, or the use of any one of clauses 3 to 19, wherein the condition is:

(i) selected from chronic inflammatory demyelinating polyneuropathy (CIDP), myasthenia gravis (MG), multiple sclerosis (MS) and neuromyelitis optica (NMO), or (ii) selected from rheumatoid arthritis and TRALI.

21. The antibody for use of any one of clauses 1 or 4 to 20 or the method of any one of clauses 2 or 4 to 20, or the use of any one of clauses 3 to 20, wherein the condition is chronic inflammatory demyelinating polyneuropathy (CIDP).

22. The antibody for use of any one of clauses 1 or 4 to 20 or the method of any one of clauses 2 or 4 to 20, or the use of any one of clauses 3 to 20, wherein the condition is myasthenia gravis (MG).

23. The antibody for use of any one of clauses 1 or 4 to 20 or the method of any one of clauses 2 or 4 to 20, or the use of any one of clauses 3 to 20, wherein the condition is multiple sclerosis (MS).

24. The antibody for use of any one of clauses 1 or 4 to 20 or the method of any one of clauses 2 or 4 to 20, or the use of any one of clauses 3 to 20, wherein the condition is neuromyelitis optica (NMO).

25. The antibody for use of any one of clauses 1 or 4 to 20 or the method of any one of clauses 2 or 4 to 20, or the use of any one of clauses 3 to 20, wherein the condition is rheumatoid arthritis.

26. The antibody for use of any one of clauses 1 or 4 to 20 or the method of any one of clauses 2 or 4 to 20, or the use of any one of clauses 3 to 20, wherein the condition is TRALI.

27. The antibody for use of any one of clauses 1 or 4 to 26 or the method of any one of clauses 2 or 4 to 26, or the use of any one of clauses 3 to 26, wherein the RBC antibody binds to a peptide epitope.

28. The antibody for use of any one of clauses 1 or 4 to 27 or the method of any one of clauses 2 or 4 to 27, or the use of any one of clauses 3 to 27, wherein the RBC antibody binds to a RBC molecule that is selected from the RhD protein, GPA, the human orthologue of TER-119 antigen (Ly76), and Band 3.

29. The antibody for use of any one of clauses 1 or 4 to 28 or the method of any one of clauses 2 or 4 to 28, or the use of any one of clauses 3 to 28, wherein the RBC antibody binds to a RBC molecule that is found at a density of $10^2$-$10^5$ copies per RBC.

30. The antibody for use of any one of clauses 1 or 4 to 29 or the method of any one of clauses 2 or 4 to 29, or the use of any one of clauses 3 to 29, wherein the antibody is administered by intravenous, intramuscular, intraperitoneal, intracerebrospinal, intracerebral, subcutaneous, intra-articular, intrasynovial, intrathecal, intrapulmonary, intranasal, intradermal topical administration or by inhalation, preferably by intravenous or subcutaneous administration.

31. The antibody for use of any one of clauses 1 or 4 to 29 or the method of any one of clauses 2 or 4 to 29, or the use of any one of clauses 3 to 29, wherein the antibody is administered so that an amount of antibody of about 0.001 mg/kg to about 100 mg/kg of the subject's body weight is administered per week.

32. The antibody for use of any one of clauses 1 or 4 to 29 or the method of any one of clauses 2 or 4 to 29, or the use of any one of clauses 3 to 29, wherein the antibody is administered so that an amount of antibody of about 0.001 mg/kg to about 100 mg/kg of the subject's body weight is administered every two weeks.

33. The antibody for use of any one of clauses 1 or 4 to 29 or the method of any one of clauses 2 or 4 to 29, or the use of any one of clauses 3 to 29, wherein the antibody is administered so that an amount of antibody of about 0.001 mg/kg to about 100 mg/kg of the subject's body weight is administered per month.

34. The antibody for use of any one of clauses 1 or 4 to 29 or the method of any one of clauses 2 or 4 to 29, or the use of any one of clauses 3 to 29, wherein the antibody is administered so that a fixed dosage from about 50 μg to about 2000 mg is administered per week.

35. The antibody for use of any one of clauses 1 or 4 to 29 or the method of any one of clauses 2 or 4 to 29, or the use of any one of clauses 3 to 29, wherein the antibody is administered so that a fixed dosage from about 50 μg to about 2000 mg is administered per two weeks.

36. The antibody for use of any one of clauses 1 or 4 to 29 or the method of any one of clauses 2 or 4 to 29, or the use of any one of clauses 3 to 29, wherein the antibody is administered so that a fixed dosage from about 50 μg to about 2000 mg is administered per month.

37. The antibody for use of any one of clauses 1 or 4 to 36 or the method of any one of clauses 2 or 4 to 36, or the use of any one of clauses 3 to 36, wherein the antibody is administered in combination with one or more other therapeutic agent(s), preferably at least one other anti-inflammatory agent, or agent that is used to treat an inflammatory condition or to alleviate the symptoms thereof.

38. The antibody for use of clause 37 or the method of clause 37, or the use of clause 37 wherein the one or more other therapeutic agent includes an anti-inflammatory.

39. The antibody for use, the method or the use of clause 37 or 38, wherein the one or more other therapeutic agent includes an immunosuppressant.

40. The antibody for use, the method or the use of any one of clauses 35 to 39, wherein the one or more other therapeutic agents includes an analgesic.

41. The antibody for use of any one of clauses 1 or 4 to 40 or the method of any one of clauses 2 or 4 to 40, or the use of any one of clauses 3 to 40, wherein the antibody binds preferably to a RBC.

42. The antibody for use of any one of clauses 1 or 4 to 41 or the method of any one of clauses 2 or 4 to 41, or the use of any one of clauses 3 to 41, wherein the RBC molecule to which the RBC antibody binds is found at a higher density on a RBC than on one or more other blood cell and/or a cell that is associated with the vascular system.

43. The antibody for use of any one of clauses 1 or 4 to 42, or the method of any one of clauses 2 or 4 to 42, or the use of any one of clauses 3 to 42, wherein the RBC molecule to which the RBC antibody binds is found at a higher density on a RBC than on a platelet, a white blood cell, and/or a cell that is associated with the vascular system.

44. The antibody for use of any one of clauses 1 or 4 to 43 or the method of any one of clauses 2 or 4 to 43, or the use of any one of clauses 3 to 43, wherein the RBC molecule to which the RBC antibody binds is not found on a platelet.

45. The antibody for use of any one of clauses 1 or 4 to 44 or the method of any one of clauses 2 or 4 to 44, or the use of any one of clauses 3 to 44, wherein the antibody causes MPS blockade in a human or in a suitable animal model in vivo.

46. The antibody for use of any one of clauses 1 or 4 to 45 or the method of any one of clauses 2 or 4 to 45, or the use of any one of clauses 3 to 45, wherein the antibody causes haemolysis in vivo, e.g. in an animal model or in a human.

47. The antibody for use of any one of clauses 1 or 4 to 46 or the method of any one of clauses 2 or 4 to 46, or the use of any one of clauses 3 to 46, wherein the antibody inhibits phagocytosis of opsonised platelets in an in vitro assay.

48. The antibody for use of any of clauses 1 or 4 to 47 or the method of any of clauses 2 or 4 to 47 or the use of any one of clauses 3 to 47, wherein administration of the antibody does not lead to tolerance of or to an antigen.

49. The antibody for use, method or use of clause 48 wherein the antigen is a protein or peptide that is administered with the antibody which is involved in or which causes the autoimmune condition.

50. The antibody for use of any of clauses 1 or 4 to 49 or the method of any of clauses 2 or 4 to 49 or the use of any one of clauses 3 to 49, wherein the antibody does not contain any non-immunoglobulin sequence, preferably wherein the antibody consists of immunoglobulin sequence, and no additional sequence is present (e.g. fused to the N or C terminus).

51. The antibody for use of any of clauses 1 or 4 to 50 or the method of any of clauses 2 or 4 to 50 or the use of any one of clauses 3 to 50 wherein the antibody is not a fusion protein with any additional protein or peptide.

52. The antibody for use of any of clauses 1 or 4 to 51 or the method of any of clauses 2 or 4 to 51 or the use of any one of clauses 3 to 51 wherein the antibody is administered to the subject in a composition, optionally wherein the composition does not comprise any cells and/or no cells are co-administered with the composition.

53. A method of treating or preventing an inflammatory condition in a subject, comprising administering to a subject in need thereof a therapeutically effective amount of human erythrocytes sensitized with an antibody to a red blood cell (RBC).

EXAMPLES

Methods

Reagents

C57BL/6 mice and SCID mice were from Charles River Laboratories (Kingston, N.Y., USA). MWReg30 was from BD Biosciences (Mississauga, Ont., Canada). 30-F1 was from Biolegend (San Diego, Calif., USA). 30-1-2S and TER-119 were from Bio X Cell (West Lebanon, N.H., USA).

ITP/Anemia

ITP was induced and platelets enumerated as described (Crow A R et al Blood. 2011;117(3):971-974). Anemia was induced and RBC enumerated as described (Chen X et al Transfusion. 2014;54(3):655-664). Mice were injected with 45 ug control rat IgG or 45 ug TER-119 at specific time points, their RBC enumerated, after which each group received 2 ug MWReg30. One hr post MWReg30 injection, mice were bled for platelet enumeration.

The K/B×N Arthritis Model

K/B×N arthritis was induced and scored as described (Mott P J et al PLoS One.

2013:8(6):e65805). Mice were pretreated with nothing or 45 ug TER-119 before injection of K/B×N serum. Mice were monitored daily for arthritis progression. In separate experiments, mice were rendered arthritic and treated on day 5 with 45 ug TER-119 or 50 ug 30-F1.

TRALI

TRALI was induced as described (Kapur R et al Blood. 2015;126(25):2747-2751). Briefly, SCID mice were injected with 40 ug TER-119 24 hr prior to injection of 50 ug 34-1-2S. Rectal temperatures were recorded every 30 min for 2 hr, then mice were sacrificed to determine lung wet/dry weight ratios.

Example 1. Generation of Antibodies Targeting Erythrocytes (TER-119, IC3, LD1/2-6-3)

A series of expression vectors referred to as pCGC vectors was generated by introducing constant region of heavy chain (CH) of various antibody isotypes into pCMV/myc/ER vector (Invitrogen, ThermoFisher Scientific Mass., USA). DNA fragments encoding variable regions (VL and VH) of anti-TER-119 (WO2013121296A1), anti-Glycophorin A antibody IC3 (WO9324630A1) and anti-D antibody LD1/2-6-3 (WO9749809A1) were codon-optimised for CHO expression and synthesized by ThermoFisher Scientific (Mass., USA). The VL and VH fragments were then co-cloned with an appropriate InTag adaptor into a relevant pCGC vector using InTag positive selection method (Chen et al 2014 Nucleic Acids Res 42(4):e26.) as illustrated in FIG. 1. The final expression vector is a dual expression vector where the light chain's expression is driven by the first CMV promoter and where the heavy chain's expression is driven by the second CMV promoter.

TABLE 3

| Ab3 | LC | HC | Vector | InTag Adaptor |
|---|---|---|---|---|
| LD1263_hKG1 | hCK | hIgG1 | pCGC1_hG1 | hCK_pGBHpA_CmR_pCMV_SP |
| LD1263_hKG2 | hCK | hIgG2 | pCGC2_hG2 | hCK_pGBHpA_CmR_pCMV_SP |
| LD1263_hKG3 | hCK | hIgG3 | pCGC3_hG3 | hCK_pGBHpA_CmR_pCMV_SP |
| LD1263_hKG4 | hCK | hIgG4p | pCGC4_hG4 | hCK_pGBHpA_CmR_pCMV_SP |
| LD1263_hKG1xv90* | hCK | hIgG1xv90 | pCGC8_hG1xv90 | hCK_pGBHpA_CmR_pCMV_SP |
| LD1263_mKG1 | mCK | mIgG1 | pCGC6_mG1 | mCK_pGBHpA_CmR_pCMV_SP |
| LD1263_mKG2a | mCK | mIgG2a | pCGC7_mG2a | mCK_pGBHpA_CmR_pCMV_SP |

*human IgG1 constant region contains S239D/I332E mutations (Lazar et al Proc Natl Acad Sci USA. 2006; 103(11): 4005-4010.)

```
Amino acid sequences
LD1/2-6-3 VL (anti human RhD)
                                        (SEQ ID NO: 1)
VMTQSPSSLSASVGDRVTITCRASQSIIRYLNWYQHKPGKAPKLLIHTASS

LQSGVPSRFSGSVSGTDFTLTISSLQPEDFATYYCQQSYTTPYTFGQGTKL

QIKR

LD1/2-6-3 VH (anti-human RhD)
                                        (SEQ ID NO: 2)
QVKLLESGGGVVQPGGSLRVACVASGFTFRNFGMHWVRQAPGKGLEWVAFI

WFDASNKGYGDSVKGRFTVSRDNSKNTLYLQMNGLRAEDTAVYYCAREKAV

RGISRYNYYMDVWGKGTTVTVSS

IC3 VL (anti-human GPA)
                                        (SEQ ID NO: 3)
DIVMSQSPSSLAVSVGEKVSMSCKSSQSLFNSRTRKNYLTWYQQKPGQSPK

PLIYWASTRESGVPDRFTGSGSGTDFTLTISSVQAEDLADYYCKQSYNLRT

FGGGTKLEIKR

IC3 VH (anti-human GPA)
                                        (SEQ ID NO: 4)
EVRLLESGGGPVQPGGSLKLSCAASGFDFSRYWMNWVRRAPGKGLEWIGEI

NQQSSTINYSPPLKDKFIISRDNAKSTLYLQMNKVRSEDTALYYCARLSLT

AAGFAYWGQGTLVTVSA

Anti-TER-119 VL (anti-mouse GPA-associated protein,
anti-Ly76)
                                        (SEQ ID NO: 5)
DIQMTQSPSVLSASVGDRVTLNCKASQNINKYLNWYQQKLGEAPKVLIYNT

NNLQTGIPSRFSGSGSGTDFTLTISSLQPEDFATYFCFQHYTWPTFGGGTK

LEIKR

Anti-TER-119 VH (anti-mouse GPA-associated protein,
anti-Ly76)
                                        (SEQ ID NO: 6)
EVKLQESGGGLVQPGGSLKLSCVASGFTFRDHWMNWVRQAPGKTMEWIGDI

RPDGSDTNYAPSVRNRFTISRDNARSILYLQMSNMRSDYTATYYCVRDSPT

RAGLMDAWGQGTSVTVSS
```

Transient mAb Expression in ExpiCHO™ Cells

Transient transfection using the Max Titer protocol of the ExpiCHO™ Expression System (Gibco, Life Technologies, Carlsbad Calif., USA) was performed according to the manufacturer's instructions. Plasmid DNA (120 μg) was diluted in 8 mL OptiPro™ SFM and mixed gently. ExpiFectamine™ CHO Reagent (640 μL) was diluted in 7.4 mL OptiPro™ SFM, mixed gently and immediately combined with the diluted DNA, mixed gently and incubated at room temperature for 2 min to allow the DNA-ExpiFectamine™ CHO complexes to form. The DNA-Expifectamine™ CHO complexes were then added to a 1 L Erlenmeyer flask containing 200 mL of ExpiCHO-S™ cells ($1.2\times10^9$ cells) in ExpiCHO Expression™ medium. The cells were incubated in a 37° C. incubator with 8% $CO_2$ shaking at 140 rpm for approximately 20 h. A master mix consisting of 1200 μL ExpiCHO™ Enhancer and 32 mL ExpiCHO™ Feed was prepared and added to each flask. The cells were incubated for further 4 days in a 32° C. incubator with 5% $CO_2$ shaking at 140 rpm. An additional 32 mL of ExpiCHO™ Feed was added and the cells incubated for a further 9 days. Protein was harvested from supernatant centrifugation at 4000 rpm at 4° C. for 20 min and filtered into a clean vessel using a 0.45 μM filter before HPLC quantification and purification.

Transient mAb Expression in Expi293F™ Cells

The transient transfection using Expi293F™ Expression System (Life Technologies, Calif., USA) was performed according to the manufacturer's instructions. Plasmid DNA (1 mg) was diluted in 50 mL Opti-MEM™ I Medium and mixed gently. Expifectamine™ 293 transfection reagent (2.7 mL) was diluted in 50 mL Opti-MEM™ I Medium, mixed gently and incubated for 5 min at room temperature. The diluted Expifectamine™ 293 transfection reagent was then added to the diluted DNA, mixed gently and incubated at room temperature for 20-30 min to allow the DNA-Expifectamine™293 transfection reagent complexes to form. The DNA-Expifectamine™293 transfection reagent complexes were then added to the 3 L Erlenmeyer Flask containing 817 mL of Expi293F™ cells ($2.5\times10^9$ cells). The cells were incubated in a 37° C. incubator with 8% $CO_2$ shaking at 120 rpm for approximately 19 h. A master mix consisting of 5 mL Expifectamine™293 Transfection Enhancer 1 (Life Technologies, Calif., USA), 50 mL Expifectamine™293 Transfection Enhancer 2 (Thermo Fisher Scientific, Calif., USA) and 25 mL of Lupin Peptone (Solabia S.A.S, France) was prepared and added to each Erlenmeyer Flask. The cells were incubated for a further 5 days in a 37° C. incubator 20 with 8% $CO_2$ shaking at 120 rpm. Protein was harvested from supernatant centrifugation at 4000 rpm for 20 min and filtered into a clean tube using a 0.45 μM filter before HPLC quantification and purification.

Example 2. Time Course Experiment with Therapeutic Antibody TER-119

A time course experiment with TER-119 in the ITP model was performed. C57BLJ6 mice were pretreated with rat 45 ug IgG (FIG. 1 A, B) or 45 ug TER-119 (FIG. 2 C, D) and blood platelets as well as blood erythrocytes enumerated over the duration depicted on the x-axis of FIG. 2. ITP was induced by 2 ug anti-platelet antibody (MWReg30) at the indicated times on the x-axis. Platelets were enumerated 1 hour after MWReg30 injection.

Mice injected with control rat IgG exhibited no anemia or amelioration of anti-platelet antibody induced ITP after short term (FIG. 2A) or long term (FIG. 2B) exposure to rat IgG. In contrast, mice pretreated with TER-119 demonstrated measurable anemia commencing 3 hr after administration (FIG. 2C). Surprisingly, amelioration of ITP was seen before the measurable onset of anemia (FIG. 2C, 0.5 hr and 1.5 hr). Conversely, we did not observe significant amelioration of ITP when maximal anemia was reached (FIG. 2D, 96 hr). These data suggest that anemia is not a prerequisite for the amelioration of ITP by TER-119. This led us to speculate that TER-119's therapeutic activity in ITP might not be due solely to competitive inhibition of MPS function.

Example 3. TER-119 Can Ameliorate Inflammatory Arthritis in the K/B×N Model

Rheumatoid arthritis is a common autoimmune disorder that involves inflammation of the synovial joints (Colmegna I, Ohata B R, Menard H A. Clin Pharmacol Ther. 2012;91 (4):607-620). The K/B×N arthritis model captures many of the immunological mechanisms of human rheumatoid arthritis (Kouskoff V et al Cell. 1996;87(5):811-822), and is not known as an inflammatory disease requiring splenic-sequestration as splenectomized mice are as susceptible to the disease as normal mice (Misharin A V et al Cell Rep. 2014;9(2):591-604). Therefore, we used this model to test TER-119's potential broad anti-inflammatory activity.

On day 0, C57BL/6 mice were assessed for basal arthritis measurements (FIG. 3 A and B). One group of mice received 45 ug TER-119 (open circle) the other group (open square) received nothing. Two hr later, all mice received an injection of K/B×N serum. Ankle measurements (A) and clinical score (B) were taken every day for 10 days according to Mott PJ et al PLoS One. 2013;8(6):e65805.

Mice injected with K/B×N serum developed inflammatory arthritis by day 2 post injection based on their clinical arthritic score (FIG. 2B, open square) and by day 3 based on their ankle width (FIG. 3A, open square). Disease severity increased with time, reaching a maximum at day 7 (clinical score) and day 8 (ankle width). In comparison, mice prophylactically treated with TER-119 demonstrated significantly reduced arthritis scores (FIG. 3A, open circle) and (FIG. 3B, open circle). These data demonstrate that a monoclonal antibody to RBC can ameliorate inflammatory arthritis, suggesting that TER-119 might exert broad anti-inflammatory activity beyond the treatment of ITP.

Example 4. TER-119 Can Reverse Established Arthritis in the K/B×N Model

We also tested TER-119's ability to ameliorate established arthritic disease. In independent experiments, mice received an injection of K/B×N serum with no pretreatment. On day 5, arthritic mice were treated (FIG. 3C/D, arrow) with nothing (FIG. 3C, open square), 50 ug 30F1 (a non-therapeutic anti CD24 antibody, as used e.g. in Song S. et. al Blood. 2003;101(9):3708-3713, open triangle) or 45 ug TER-119 (open circle). Ankle measurements (C) and clinical score (D) were measured on days 0, 1, 2 and 5-9.

In this set of experiments, mice developed maximal arthritis at day 5 based on their ankle width (FIG. 3C) and clinical score (FIG. 3D). Mice that were treated with TER-119 on day 5 showed a remarkable reduction in arthritic inflammation 1 day post treatment, with ankle widths and clinical scores returning to normal 3 days post treatment. Although the decrease in ankle width was not significant at 1 day post treatment (day 6, P=0.06), there was a substantial reduction in swelling. Mice receiving the RBC antibody 30-F1 (a rat IgG2c antibody which does not bind to Fc receptors and does not ameliorate murine ITP (Song S, et al Blood. 2003;101(9):3708-3713)) showed no improvement in inflammation, similar to untreated mice. These data demonstrate that TER-119 can reverse established arthritis and that an IgG subtype must be selected that can bind activating Fc receptors. This was also confirmed by deglycosylating TER-119, a process known to greatly diminish Fc receptor binding activity, and showing that deglycosylated TER-119 did not significantly ameliorate K/B×N arthritis or ITP (data not shown).

Example 5. TER-119 Can Ameliorate Inflammatory Arthritis in the Collagen Antibody Induced Arthritis CAbIA Model Experimental Outline Erythrocyte targeting antibodies were examined for therapeutic efficacy in the collagen Ab-induced arthritis (CAbIA) model in mice (Campbell I K et al J Immunol. 2014, 192: 5031-5038. Campbell I K et al J Immunol. 2016,197:4392-4402).

Reagents

Anti-type II collagen mAb cocktail (CAb), Chondrex Cat# 53100, 10 mg/ml (lot#150211).

LPS (*E. coli* 0111:B4), Chondrex Cat# 53100, 0.5 mg/ml (lot#140243).

Rat IgG2b (Isotype Ctrl), 2.75 mg/ml, 4.5.17, WEHI Antibody Facility.

TER-119, 2.00 mg/ml, 4.5.17, WEHI Antibody Facility.

Mice 30 male C57BLJ6 mice (aged 7-8 wks) were obtained from the Bio21 Animal Facility, Melbourne, Australia. The mice were allowed to acclimatise in the CSL mouse rooms at Bio21 for one week before the experiment was commenced.

Procedure

On day 0, all mice were injected i.p. with 0.2 ml anti-collagen mAb cocktail (10 mg/ml). On day 3, all mice were injected i.p. with 0.1 ml LPS (0.5 mg/ml). At day 5, arthritic mice were randomly distributed into the treatment groups (Table 4) and given a single i.v. injection with the indicated reagents. The experiment was terminated at day 12.

Histology of Arthritic Joints

At day 12, mice were killed and the rear paws were fixed in 10% neutral buffered formalin, decalcified and embedded in paraffin. Sagittal tissue sections were stained with H&E and scored blinded to the treatment groups. The ankle joints were globally scored for three features (exudate—presence of inflammatory cells within the joint space; synovitis—the degree of synovial membrane thickening and inflammatory cell infiltration; tissue destruction—cartilage and bone erosion and invasion), each out of five (0—normal, 1—minimum, 2—mild, 3—moderate, 4 —marked, 5—severe), and these were tallied for a total score out of fifteen.

TABLE 4

| Group # | Drug | Dose | Route | n= |
|---|---|---|---|---|
| 1 | Isotype Ctrl | 2 mg/kg | i.v. | 9 |
| 2 | TER-119 | 2 mg/kg | i.v. | 9 |

Summary of Treatment Groups.

Results

The TER-119-treated mice were completely protected from arthritis within 24 h of injection and this was sustained until the end of the experiment at day 12 (FIG. 4*a*).

Blinded histological scoring of the rear right ankle joints of mice at day 12 (isotype control, n=9; TER-119, n=6) showed a clear difference between the two treatment groups (FIG. 4*b*). The TER-119-treated joints were normal in appearance with no signs of the inflammation and joint tissue destruction that was seen in the isotype-control mAb-treated arthritic mice. Note that 3 mice in the TER-119-treated group were euthanised prior to completion of the study due to excessive weight loss.

Effect of Different Doses of TER-119

The effect of different doses of TER-119 (1, 1.5 and 2 mg/kg) on clinical score (FIG. 4C and D) and accumulation of cells in the joint (FIG. 4E) was assessed. To assess the number of infiltrating cells in the joints the patellas from each mouse were collected, digested and infiltrating leukocytes enumerated by visual count.

1.5 and 2 mg/kg Ter119 are effective in reducing clinical score. All doses are significantly reducing joint infiltrating cell numbers. Ter119 at the 1 mg/kg dose results in significantly lower bound antibody on the surface of RBC compared to the 1.5 and 2 mg/kg dose which correlates to the clinical score (FIG. 4F).

CAbIA results in increases in C3, and C5a in the joints (Spirig R, et al J Immunol. 2018,200:2542-2553.) and these complement components as well as C1q were decreased by TER-119 in the joints (FIG. 4G) without differences observed in these complement components in the plasma (not shown).

Effect of Different Antibodies

C57BLJ6 mice injected with the collagen antibody cocktail (day 0) and LPS (day 3) were allowed to develop arthritis and then injected (day 6; treatment) with 2 mg/kg of either TER-119, deglycosylated TER-119 (a variant without the Fc glycan, which thus is impaired for Fc receptor and complement binding), M1/69 or an IgG2b isotype control antibody and the clinical scores and paw width were evaluated daily (FIG. 4H). Only two mice were tested with M1/69.

TER-119 is specific for the glycophorin A complex on erythrocytes while M1/69 reacts with mouse CD24, also known as Heat Stable Antigen (HSA), Ly-52, or Nectadrin and is a ~35-45 kDa glycoprotein anchored in the plasma membrane via a phosphatidylinositol linkage and is an antigen expressed on erythrocytes as well as lymphocytes, granulocytes, thymocytes, epithelial cells, neurons, and dendritic cells.

Both TER-119 and M1/69 can increase platelet counts in a murine model of ITP (Song S. et. al Blood. 2003;101(9):3708-3713). To verify the binding of these antibodies with murine erythrocytes the antibodies (0-512 ng of the primary antibody) were reacted with erythrocytes from C57BLJ6 mice followed by a secondary anti-rat Ig-phycoerythrin conjugate and assessed by flow cytometry (see FIG. 41). TER-119, deglycosylated TER-119 and M1/69 comparatively bound erythrocytes at all doses studied in comparison to the isotype control.

Clinical scores for all arthritis models and were assigned as follows: 0, normal; 0.5, swelling confined to digits; 1, mild paw swelling; 2, marked paw swelling; 3, severe paw swelling and/or ankylosis.

Conclusions

Intravenous TER-119 was therapeutically effective in blocking established CAbIA when assessed both clinically and histologically.

Example 6. TER-119 Treatment Can Significantly Prevent 34-1-2S Induced Hypothermia Transfusion related acute lung injury (TRALI) is one of the most serious complications of blood transfusion (Chapman C E et al Transfusion. 2009;49(3):440-452). Infusion of an MHC Class I antibody (34-1-2S) (Looney M R et al J Clin Invest. 2006;116(6):1615-1623) into SCID mice induces symptoms approximating human TRALI, an inflammatory disease with symptoms disparate from those observed in ITP and arthritis (Fung Y L et al Blood. 2010;116(16):3073-3079). As we have recently found that inflammation is a risk for murine TRALI (Kapur R et al Blood. 2015;126(25):2747-2751), we next explored the ability of TER-119 to inhibit the induction of this disease.

SCID mice were injected with 40 ug of TER-119 (FIG. 3E/F, open circle, open triangle) or left untreated (open square) for 24 hrs. Mice were then injected with 50 ug of 34-1-2S (open triangle, open square) or nothing (open circle). Rectal temperatures were measured every 30 min for 2 hr (FIG. 3E) and mice were subsequently sacrificed at 2 hr to assess pulmonary edema (FIG. 3F). Mouse rectal temperatures were monitored to evaluate systemic shock induced by 34-1-2S (Fung Y L et al Blood. 2010;116(16):3073-3079). Compared with mice injected with TER-119 alone, mice receiving 34-1-2S displayed a decrease in rectal temperature at 30 min post injection (FIG. 3E) which decreased until 90 min, staying stable until the end point of 120 min. In contrast, mice receiving a pretreatment of TER-119 prior to 34-1-2S injection displayed a less pronounced drop in body temperature at 30 min, which became significant at 60, 90 and 120 min (vs. 34-1-2S alone). These data demonstrate that TER-119 treatment can significantly prevent 34-1-2S induced hypothermia.

Post-mortem determination of pulmonary edema was measured by wet/dry (W/D) lung weight ratios. Mice that received 34-1-2S after pre-treatment with TER-119 displayed lung W/D ratios similar to those treated with TER-119 alone, but significantly lower than mice injected with 34-1-2S only, which experienced TRALI based on their increased W/D weight ratios. Thus TER-119 can prevent 34-1-2S induced systemic shock and ameliorate pulmonary edema. Since sensitized RBC are not known to transit to the lung (or the joints), this indicates that the anti-inflammatory effects of anti-RBC antibodies are not likely local.

Example 7. TER-119 Can Inhibit Phagocytosis in Vitro (Mouse System)

TER-119 binds RBC and TER-119 opsonized RBCs are phagocytosed in a concentration dependent manner.

Materials and Methods

Preparation of RAW264.7 Cells

Raw cells were harvested by scraping into fresh RPMI-1640 supplemented with 10% heat-inactivated FBS, and cells were enumerated using a Beckman Coulter Vi-Cell XR, Cell viability Analyzer (Serial No AT08066) and adjusted to $5x10^5$ cells/mL. Cells were cultured in 12 well plates with coverslips using 1 mL of the cell preparation per well. Cells were incubated overnight at 37° C.

Platelet and Erythrocyte Enumeration

Five to eight hundred μL of whole blood was acquired from each mouse using cardiac puncture. Blood was immediately mixed with 200 μL of a 1:1 (Anticoagulation buffer: BSGC buffer) and diluted to a final volume of 1.5 mL using BSCG buffer. Each diluted blood sample was centrifuged at 300 g for 3 min at room temperature and platelet rich plasma (PRP) was collected. Remaining sample was again resuspended to 1.5 mL in BSGC and centrifuged again. PRP was again collected and added to the previous PRP sample, this PRP mixture was then centrifuged at 1200 g for 10 min. The platelet pellet was resuspended in 1 mL BSGC and 5 μL of PRP was diluted 1:200 in BSGC buffer then platelets were counted on a MACSQuant analyzer 10 (MACS Miltenyi Biotec) flow cytometer to determine the concentration of platelets in the preparation.

RBCs were then resuspended in 1 mL PBS and each sample was diluted 1:3000 in PBS and then analyzed by flow cytometry (Guava EasyCyte flow cytometry system) to determine the concentration of erythrocytes in the blood.

Labeling of Platelets with CMFDA Cell Tracker Green

Platelets were counted using the MACSQuant analyzer 10 (MACS Miltenyi Biotec) flow cytometer by taking 5 μL of PRP and diluting in 995 μL of BSGC buffer. Platelets were adjusted to $5\times10^8$ platelets/mL. CM FDA was prepared at a concentration of 10 μg/m L. Then equal volumes of platelets and CMFDA (e.g. 1 mL of platelet and 1 mL of CMFDA) 10 were mixed together for a final CMFDA concentration of 5 μg/mL. Mixture was incubated for 30 mins at 37° C. with gentle mixing in the dark.

Opsonization of Platelets with Anti-CD41 (Mwreg30) Antibody and of RBCs with Anti-RBC Antibodies Following incubation with CM FDA platelets were centrifuged at 1200 g for 10 min and pellet was resuspended in 1 mL of HBSS. Mwreg30 antibody was added to platelet samples at a concentration of 10 μg/mL. Mixture was incubated for 30 min at room temperature with gentle mixing.

RBCs were counted using the Guava Easy Cyte Mini (Serial No 2800060170) and adjusted to $5\times10^8$ RBCs/mL. Anti-RBC antibodies of select concentrations, were added to one mL of RBCs. Mixture was incubated for 1 hr at room temperature with gentle mixing.

Incubation with RAW264.7 Cells

Following 1 hour incubation with antibodies, RBCs were washed with PBS and centrifuged for 300 g for 8 mins. RBCs were counted again and adjusted to $0.4\times10^8$ RBCs/mL using RPMI-1640 supplemented with 10% heat-inactivated FBS. Platelets were washed with HBSS and centrifuged at 1200g for 10 mins. Platelets were counted again and adjusted to $3\text{-}5\times10^8$ platelets/mL into RPMI-1640 supplemented with 10% heat-inactivated FBS. To add the RBCs and platelets, supernatant was removed from RAW 264.7 cells and 100 ul of the platelet preparation was added ($3\text{-}5\times10^7$ platelets; ratio 1 macrophage: 100 platelets) and 250 ul of the RBC preparation was added (10×106 RBCs; ratio ~1 macrophage: 20 platelets) per well. Cells were incubated at 37° C. for 30 min.

Post Phagocytosis Preparation

Phagocytosis was stopped by placing the cells on ice. RAW 264.7 cells were washed once with 500 μL HBSS (1 μg/mL carbacyclin) per well. Remaining RBCs were lysed by adding 0.9 mL of dH2O per well for 1.5 mins then 0.1 mL PBS 10× was added to stop the lysing process. Cells were washed 2 more times with 500 μL HBSS. Finally, 500 μL of a solution of PBS/0.5 mM EDTA /0.05% trypsin was added to wells for 5 mins at 37° C. to remove any remaining bound platelets. The trypsin/EDTA solution was removed and cells were place in 500 μL RPMI 1640 containing HEPES buffer.

Confocal Imaging and Calculation of the Phagocytic Index

Pictures were taken using the LSM 700 Zeiss Confocal microscope. Five pictures were taken per well (top, bottom, center, left and right). Internalized platelets were counted using IMARIS 8.0. The criteria of an internalized platelet in these experiments were: a minimum volume of 4.2 μM, green florescence and internalization of the platelet by the macrophage on the x, y and z planes. Macrophages were counted using Fiji (Fiji is Just Images) cell counting program. The Phagocytic Index (PI) was calculated using the following equation:

$$PI=(\text{Total number of engulfed platelets}/\text{Total number of counted macrophages})\times100$$

Immunofluorescence Detection of Opsonized Erythrocytes

Five to eight hundred μL of whole blood was acquired from each mouse using cardiac puncture and the blood immediately diluted in 200 μL of a 1:1 (Anticoagulation buffer: BSGC buffer) and further diluted to a total volume of 1.5 mL using BSCG buffer. Each diluted blood sample was centrifuged at 300 g for 3 min in room temperature and platelet rich plasma (PRP) was removed. RBCs were then resuspended in 1 mL PBS and each sample was diluted 1:3000 in PBS. RBCs were counted using the Guava EasyCyte Mini (Serial No 2800060170) and adjusted to $5\times10^8$ RBCs/mL. One mL of RBCs was used per antibody. Antibodies were added to RBC suspensions at the indicated concentrations. The mixtures were incubated for 1 hr at 37° C. with gentle mixing. Following incubation RBCs were washed and readjusted to $10^8$ RBCs/mL, 100 μL of the sample was added to 5 mL flow cytometry tubes and incubated in 100 μL of a preparation of the appropriate species specific R-PE-conjugated secondary antibody (1:200) for 30 min at room temperature. A final wash was performed to remove the unbound antibody. The samples were then analyzed by flow cytometry (Guava EasyCyte flow cytometry system) to determine the mean fluorescence intensity (MFI) of the antibody-opsonized erythrocytes.

Results

Mouse RBCs were incubated with various concentrations of the TER-119 antibody for 45 minutes at room temperature, washed and then added to RAW macrophages for 30 mins at 37° C. and 5% $CO_2$. Following incubation, the remaining RBCs were lysed with $H_2O$ for 2 mins and RAW cells were fixed with 4% PFA before being visualized on a phase contrast microscope. Macrophages and internalized RBCs were counted and the phagocytic index was calculated. TER-119 was able to opsonize RBCs for phagocytosis at concentrations as low as 1.25 μg/mL (FIG. 5). The maximal RBC phagocytosis (i.e. Plateau) was achieved 5 μg/mL (FIG. 5).

Furthermore, it was demonstrated that TER-119 opsonized RBCs prevent platelet phagocytosis in vitro by using a confocal microscopy approach (data not shown). RBC opsonized with TER-119 significantly inhibited the uptake of CMFDA labelled platelets by RAW 264.7 cells, whereas control RBCs did not influence the uptake (data not shown). Calculation of the phagocytic index confirmed that TER-119 opsonized RBCs were able to reduce platelet phagocytosis by approximately 75% (FIG. 6).

Different antibodies have different capacities in inhibiting phagocytosis. Erythrocytes from normal mice were either non-opsonized or opsonized with antibody TER-119, deglycosylated TER-119, 34-3C (5 or 40 ug), or M1/69 for 1 hour then incubated with RAW 264.7 cells and MWReg30 opsonized CFMDA labelled platelets for 30 minutes. The reactivity of the tested antibodies is shown in Table 5, below and FIG. 7. Cells were visualized by confocal microscopy and internalized platelets were counted by Imaris software version 8.0.2. Only TER-119, 34-3C and M1/69 were able to significantly inhibit platelet phagocytosis in vitro (P<0.05). (n=4-6 per group).

Anti-Erythrocyte Antibody Coated RBCs Ability to Inhibit Platelet Phagocytosis

TABLE 5

Summary of anti-erythrocyte antibody properties

| Antibody | Isotype | Reactivity | RBC binding[1] | RBC clearance [2] | Ameliorates ITP | Causes RBC Phagocytosis | Inhibits platelet Phagocytosis |
|---|---|---|---|---|---|---|---|
| TER-119 | RatIgG2$_b$ | mGPA | ++++ | ++++ | Yes | YES | YES |
| Deglycosylated TER-119 | RatIgG2$_b$ | mGPA | +++ | – | No | NO | NO |
| 34-3C | Mouse IgG2$_a$ | Band3 | ++++ | +++ | Yes | YES | YES |
| M1/69 | Rat IgG2$_b$ | CD24 | ++++ | ++++ | Yes | YES | YES |

[1]RBC binding denotes how well the antibody bound to RBCs which was measured by flow Cytometry (++++ = MFI > 500; +++ = MFI ≥ 250; ++ = MFI > 125; + = MFI > 62.5; – = MFI < 62.5)

[2] RBC clearance denotes how well an antibody was able to clear RBCs from circulation (++++ = >50% clearance; +++ = >25%; ++ = >12.5%; + = >6.25%; – = <6.25%)

Example 8. Testing the Ability of Erythrocyte Targeting Antibodies to Ameliorate MG Mice (057B1/6, 8-10 week old) are immunized with 20-40 micrograms of acetylcholine receptor extracted and purified from torpedo californica (T-AChR) in Complete Freund's Adjuvant (CFA) on days 0, 28 and 56. A CFA control group is also included. Immunizations are performed in four sites, subcutaneously. The first injections are performed in the two-hind foot-pads and over the scapula and subsequent injections in the scapula and thighs (Wu B et al Curr Protoc Immunol. 2001; Chapter 15:unit 8).

Mice are screened for the development of generalized muscle weakness by measuring grip strength (as an objective measurement of muscle weakness) or time during inverted hang. Muscle weakness can also be measured post-exercise. For this purpose, mice are placed on a flat platform and observed for muscle weakness. Then they are exercised by gently dragging them suspended by the base of the tail across a cage top grid repeatedly (20-30 minutes) as they attempt to grip the grid. They are placed on a flat platform for 2 min and again observed signs of muscle weakness. Clinical muscle weakness can be graded as follows: Grade 0, mouse with normal posture; Grade 1, normal at rest but with muscle weakness characteristically shown by a hunchback posture, restricted mobility and difficulty in raising the head after exercise; Grade 2, grade 1 symptoms without exercise during observation period; Grade 3, dehydrated and moribund with grade 2 weakness.

Antibodies (IgG2b) specific for T-AChR are determined when significant mice demonstrate grade 1-3 weakness.

Mice demonstrating grade 1-3 weakness and significantly positive T-AChR specific IgG2b antibodies are randomized into the following groups:

1. Treatment with isotype control
2. Treatment with anti-TER-119 antibodies
3. Treatment with anti-glycophorin A antibodies Mice are injected with either Ab at a single dose, for instance with 2 mg/kg, iv. Doses could also be between 0.1 mg/kg to 2 mg/kg. The antibodies could also be administered intraperitoneally or subcutaneously.

Clinical scores and muscle weakness are determined twice a week for a total period of one month after administration of antibodies. Sera, muscles (i.e. triceps) and carcass at the termination of the experiments are frozen from individual mice. The titers of T-AChR specific IgG2b antibodies are determined in sera, and tissues are analysed by immune histology for complement deposition (C3 and C5b-C9).

Example 9. Testing Erythrocyte Targeting Antibodies in NMO

Weight-matched female Sprague Dawley rats (250-300 g, age 9-12 weeks) are anesthetized using ketamine (100 mg/kg) and xylazine (10 mg/kg) and then mounted onto a stereotaxic frame. Following a midline scalp incision, a burr hole of 1 mm diameter is created 0.5 mm anterior and 3.5 mm lateral of bregma. A 40-μm diameter glass needle is inserted 5 mm deep to infuse 30 or 40 μg recombinant anti-AQP4-IgG intracerebral in a total volume of 3-6 μL over 10 minutes by pressure injection. On the same day, rats are treated with 1) anti-TER-119 antibodies or 2) isotype control at single dose of 0.1-2 mg/kg, ip. At day 5 rats are deeply anesthetized, followed by a transcardiac perfusion through the left ventricle with 200 ml of heparinized PBS and then 100 ml of 4% paraformaldehyde (PFA) in PBS. Brains are fixed in 4% PFA, left overnight at 4° C. in 30% sucrose and embedded in OCT. Fixed brains are frozen, sectioned (10-μm thickness) and incubated in blocking solution (PBS, 1% bovine serum albumin, 0.2% Triton X-100) for 1 h prior to overnight incubation (4° C.) with primary antibodies to: AQP4 (1:200, Santa Cruz Biotechnology, Santa Cruz, Calif.), GFAP (1:100, Millipore), myelin basic protein (MBP) (1:200, Santa Cruz Biotechnology), ionized calcium-binding adaptor molecule-1 (lba1; 1:1000; Wako, Richmond, Va.), C5b-9 (1:50, Hycult Biotech, Uden, The Netherlands) or CD45 (1:10, BD Biosciences, San Jose, Calif.), followed by the appropriate fluorescent secondary antibody (1:200, I nvitrogen, Carlsbad, Calif.). Sections are mounted with VECTASHIELD (Vector Laboratories, Burlingame, Calif.) for visualization on a Leica fluorescence microscope. NMO pathology is assessed by AQP4 and myelin loss and complement deposition.

Example 10. Testing the Ability of Erythrocyte Targeting Antibodies to Inhibit FcγR Function in Vitro Human System FcγR functions include FcγR mediated uptake of e.g. immunoglobulin coated particles. Immune complexes of anti-RBC antibodies and erythrocytes are expected to be more effective in blocking Fcγ-receptors than antibodies alone, which is expected to result in a general status of anti-inflammation/immunosuppression. This effect will probably depend on the density of the antigen on the RBC's surface and the isotype of the tested antibody. To investigate the effect of different anti-RBC antibodies, FcγR expressing cells like THP1 cells or human monocytes/macrophages are incubated with RBC-anti-RBC antibody complexes and subsequently the ability of the FcγR-expressing cells to phagocytose IgG-coated particles or bacteria is measured. If the RBC-antibody complexes block FcγRs on the surface of the cells, FcγR mediated uptake is reduced. (Experiments adapted from Tridandapani et al J Biol Chem. 2002;277(7): 5082-9; Nagelkerke S Q et al Blood. 2014; 124(25):3709-18; Coopamah M D et al Blood. 2003; 102(8):2862-7).

Immune complexes of anti-RBC antibodies and erythrocytes induce phagocytosis by themselves (similar to the mouse system) but also inhibit phagocytosis of other particles and bacteria by this mechanism.

Example 11. Testing the Ability of Erythrocyte Targeting Antibodies to Inhibit FcγR Surface Expression in Vitro in Human System In line with the above described mechanism of immune complexes of anti-RBC antibodies and erythrocytes binding to FcγR and thereby blocking FcγR function, such as FcγR mediated phagocytosis, FcγR expression itself are expected to also be influenced. To investigate the effect of RBC-anti-RBC antibody complexes on FcγR expression on the cell surface, THP1 cells or human monocytes/macrophages are incubated with the complexes and FcγR expression is assessed over time by FACS. Activating FcγRs including CD64, CD32a and CD16 are expected to get downregulated, whereas the inhibitory receptor CD32b might even get upregulated (experiments adapted from Song S. et. al Blood. 2003;101(9):3708-3713).

Example 12. The TER-119 Antibody Switched to Murine IgG Variants Ameliorated Collagen-Induced Arthritis (CIA)

To verify disease ameliorative activity in a B cell- and T cell-dependent chronic disease model independent of the infusion of disease inducing antibodies or sera therapeutic responses in CIA were assessed. In addition, to assess murine versions of TER-119, the rat IgG2b constant regions were replaced with murine IgG1 and IgG2a. 2 mg/kg of each of these antibodies were injected into different groups of DBA/1 mice pre-immunized with type II collagen for 28 days as described (Campbell I K et. al J Leuk Biol 2000; 68:144-50). Briefly, DBA-1 mice were injected with chicken collagen in complete Freud's adjuvant 21 days apart and treated 7 days later with 2 mg/kg of isotype switched (mouse IgG1, mouse IgG2a) TER-119 by the i.v. route and clinical scores assessed.

Both murine IgG subtypes could decrease clinical scores in arthritic mice within 1 day of injection and the ameliorative effects lasted for a full week followed by a return to arthritis (FIG. 8). Thus disease amelioration extends beyond just antibody-induced arthritis models. The CIA model was performed as described (Campbell I K et. al J Leuk Biol 2000;68:144-50).

Example 13: 34-3C Can Ameliorate Inflammatory Arthritis in the Collagen Antibody Induced Arthritis CAbIA Model We also tested the ability of the 34-3C mAb, which targets the Band 3 antigen on erythrocytes, to ameliorate established arthritic disease in the CAbIA model in mice. On day 0, all mice were injected i.p. with 0.2 ml anti-collagen mAb cocktail (10 mg/ml). On day 3, all mice were injected i.p. with 0.1 ml LPS (0.5 mg/ml). At day 5, arthritic mice were randomly distributed into the treatment groups and given a single i.v. injection of 2 mg/kg 34-3C (FIG. 9, filled square) or PBS (filled circle) as negative control. The experiment was terminated at day 12. Mice treated with PBS as control increased disease severity with time, reaching a maximum at day 8 (clinical score). In comparison, mice receiving the RBC antibody 34-3C (a mouse IgG2a, Leddy J P, J. Clin. Invest. 1993;91:1672-1680) showed significant reduction in clinical score. These data demonstrate that the 34-3C mAb can reverse established arthritis.

The invention claimed is:

1. A method of treating an inflammatory condition, comprising administering an antibody to a red blood cell (RBC) ("RBC antibody") to a subject having the inflammatory condition, wherein the RBC antibody is not linked to or fused with any additional protein or peptide and wherein the antibody does not comprise non-immunoglobulin amino acid residues at its N- or C-terminus;

wherein the antibody comprises an Fc region that is not deglycosylated and that is capable of binding to an activating Fc receptor, wherein the activating Fc receptor is one or more of FcγRI (CD64), FcγRIIA (CD32a), FcγRIIIA (CD16a), or FcγRIIIB (CD16b); and wherein the RBC antibody binds to Glycophorin A (GPA), and wherein the antibody comprises:

a light chain variable region comprising the amino acid sequence of SEQ ID NO: 3, and a heavy chain variable region comprising the amino acid sequence of SEQ ID NO: 4; and wherein the inflammatory condition is selected from chronic inflammatory demyelinating polyneuropathy (CIDP), myasthenia gravis (MG), multiple sclerosis (MS), neuromyelitis optica (NMO), rheumatoid arthritis, hypothermia, or transfusion related acute lung injury (TRALI).

2. The method according to claim 1, wherein the antibody is monoclonal.

3. The method according to claim 2, wherein the Fc region comprises a human IgG1 or lgG3 Fc region.

4. The method according to claim 1, wherein the inflammatory condition is selected from chronic inflammatory demyelinating polyneuropathy (CIDP), myasthenia gravis (MG), multiple sclerosis (MS) and neuromyelitis optica (NMO).

5. The method according to claim 1, wherein the inflammatory condition is selected from rheumatoid arthritis and transfusion related acute lung injury (TRALI).

6. The method according to claim 1, wherein the RBC antibody binds to a peptide epitope.

7. The method according to claim 1, wherein the RBC antibody binds to GPA that is found at a density of $10^2$-$10^5$ copies per cell.

8. The method according to claim 1, wherein the antibody is administered by intravenous or subcutaneous administration.

9. The method according to claim 1, wherein the antibody is administered in combination with one or more other therapeutic agent.

10. The method according to claim 9, wherein the one or more other therapeutic agent comprises at least one other anti-inflammatory agent, or agent that is used to treat an inflammatory condition or to alleviate the symptoms thereof.

11. The method according to claim 9, wherein the one or more other therapeutic agent is selected from an anti-inflammatory, an immunosuppressant and/or an analgesic.

12. The method according to claim 1, wherein:

administration of the antibody does not lead to tolerance of or to an antigen involved in or which causes the autoimmune condition.

13. The method according to claim 1, wherein the antibody is administered to the subject in a composition that does not comprise any cells and/or wherein no cells are co-administered with the antibody.

14. The method according to claim 1, wherein the inflammatory condition is selected from rheumatoid arthritis, transfusion related acute lung injury (TRALI), hypothermia, myasthenia gravis (MG), or neuromyelitis optica (NMO).

* * * * *

SEQUENCE LISTING

```
<160> NUMBER OF SEQ ID NOS: 6

<210> SEQ ID NO 1
<211> LENGTH: 106
<212> TYPE: PRT
<213> ORGANISM: Homo sapiens

<400> SEQUENCE: 1

Val Met Thr Gln Ser Pro Ser Ser Leu Ser Ala Ser Val Gly Asp Arg
1               5                   10                  15

Val Thr Ile Thr Cys Arg Ala Ser Gln Ser Ile Ile Arg Tyr Leu Asn
            20                  25                  30

Trp Tyr Gln His Lys Pro Gly Lys Ala Pro Lys Leu Leu Ile His Thr
        35                  40                  45

Ala Ser Ser Leu Gln Ser Gly Val Pro Ser Arg Phe Ser Gly Ser Val
    50                  55                  60
```

```
Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Thr Thr Pro Tyr Thr Phe
                85                  90                  95

Gly Gln Gly Thr Lys Leu Gln Ile Lys Arg
            100                 105


<210> SEQ ID NO 2
<211> LENGTH: 125
<212> TYPE: PRT
<213> ORGANISM: Homo sapiens

<400> SEQUENCE: 2

Gln Val Lys Leu Leu Glu Ser Gly Gly Gly Val Val Gln Pro Gly Gly
1               5                   10                  15

Ser Leu Arg Val Ala Cys Val Ala Ser Gly Phe Thr Phe Arg Asn Phe
            20                  25                  30

Gly Met His Trp Val Arg Gln Ala Pro Gly Lys Gly Leu Glu Trp Val
        35                  40                  45

Ala Phe Ile Trp Phe Asp Ala Ser Asn Lys Gly Tyr Gly Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Glu Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125


<210> SEQ ID NO 3
<211> LENGTH: 113
<212> TYPE: PRT
<213> ORGANISM: Mus musculus

<400> SEQUENCE: 3

Asp Ile Val Met Ser Gln Ser Pro Ser Ser Leu Ala Val Ser Val Gly
1               5                   10                  15

Glu Lys Val Ser Met Ser Cys Lys Ser Ser Gln Ser Leu Phe Asn Ser
            20                  25                  30

Arg Thr Arg Lys Asn Tyr Leu Thr Trp Tyr Gln Gln Lys Pro Gly Gln
        35                  40                  45

Ser Pro Lys Pro Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Asp Tyr Tyr Cys Lys Gln
                85                  90                  95

Ser Tyr Asn Leu Arg Thr Phe Gly Gly Gly Thr Lys Leu Glu Ile Lys
            100                 105                 110

Arg


<210> SEQ ID NO 4
<211> LENGTH: 119
<212> TYPE: PRT
<213> ORGANISM: Mus musculus
```

<400> SEQUENCE: 4

Glu Val Arg Leu Leu Glu Ser Gly Gly Gly Pro Val Gln Pro Gly Gly
1 5 10 15

Ser Leu Lys Leu Ser Cys Ala Ala Ser Gly Phe Asp Phe Ser Arg Tyr
20 25 30

Trp Met Asn Trp Val Arg Arg Ala Pro Gly Lys Gly Leu Glu Trp Ile
35 40 45

Gly Glu Ile Asn Gln Gln Ser Ser Thr Ile Asn Tyr Ser Pro Pro Leu
50 55 60

Lys Asp Lys Phe Ile Ile Ser Arg Asp Asn Ala Lys Ser Thr Leu Tyr
65 70 75 80

Leu Gln Met Asn Lys Val Arg Ser Glu Asp Thr Ala Leu Tyr Tyr Cys
85 90 95

Ala Arg Leu Ser Leu Thr Ala Ala Gly Phe Ala Tyr Trp Gly Gln Gly
100 105 110

Thr Leu Val Thr Val Ser Ala
115

<210> SEQ ID NO 5
<211> LENGTH: 107
<212> TYPE: PRT
<213> ORGANISM: Rattus norvegicus

<400> SEQUENCE: 5

Asp Ile Gln Met Thr Gln Ser Pro Ser Val Leu Ser Ala Ser Val Gly
1 5 10 15

Asp Arg Val Thr Leu Asn Cys Lys Ala Ser Gln Asn Ile Asn Lys Tyr
20 25 30

Leu Asn Trp Tyr Gln Gln Lys Leu Gly Glu Ala Pro Lys Val Leu Ile
35 40 45

Tyr Asn Thr Asn Asn Leu Gln Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Phe Gln His Tyr Thr Trp Pro Thr
85 90 95

Phe Gly Gly Gly Thr Lys Leu Glu Ile Lys Arg
100 105

<210> SEQ ID NO 6
<211> LENGTH: 120
<212> TYPE: PRT
<213> ORGANISM: Rattus norvegicus

<400> SEQUENCE: 6

Glu Val Lys Leu Gln Glu Ser Gly Gly Gly Leu Val Gln Pro Gly Gly
1 5 10 15

Ser Leu Lys Leu Ser Cys Val Ala Ser Gly Phe Thr Phe Arg Asp His
20 25 30

Trp Met Asn Trp Val Arg Gln Ala Pro Gly Lys Thr Met Glu Trp Ile
35 40 45

Gly Asp Ile Arg Pro Asp Gly Ser Asp Thr Asn Tyr Ala Pro Ser Val
50 55 60

Arg Asn Arg Phe Thr Ile Ser Arg Asp Asn Ala Arg Ser Ile Leu Tyr
65 70 75 80

Leu Gln Met Ser Asn Met Arg Ser Asp Tyr Thr Ala Thr Tyr Tyr Cys

-continued

```
              85                  90                  95

Val Arg Asp Ser Pro Thr Arg Ala Gly Leu Met Asp Ala Trp Gly Gln
            100                 105                 110

Gly Thr Ser Val Thr Val Ser Ser
        115                 120
```